(12) United States Patent
Li

(10) Patent No.: US 8,669,289 B2
(45) Date of Patent: Mar. 11, 2014

(54) METHODS AND COMPOSITIONS RELATING TO HEMATOLOGIC MALIGNANCIES

(75) Inventor: Shaoguang Li, Canton, MA (US)

(73) Assignee: The Jackson Laboratory, Bar Harbor, ME (US)

( * ) Notice: Subject to any disclaimer, the term of this patent is extended or adjusted under 35 U.S.C. 154(b) by 0 days.

(21) Appl. No.: 13/265,716

(22) PCT Filed: Apr. 26, 2010

(86) PCT No.: PCT/US2010/032416
§ 371 (c)(1),
(2), (4) Date: Oct. 21, 2011

(87) PCT Pub. No.: WO2010/124283
PCT Pub. Date: Oct. 28, 2010

(65) Prior Publication Data
US 2012/0114605 A1    May 10, 2012

Related U.S. Application Data

(60) Provisional application No. 61/172,447, filed on Apr. 24, 2009.

(51) Int. Cl.
*A01N 47/28* (2006.01)
*A61K 31/17* (2006.01)
*A01N 37/18* (2006.01)
*A61K 31/65* (2006.01)
*C07D 471/04* (2006.01)
*C07D 471/22* (2006.01)
*C07D 487/04* (2006.01)

(52) U.S. Cl.
USPC ........... 514/588; 514/413; 514/152; 514/248; 514/257

(58) Field of Classification Search
None
See application file for complete search history.

(56) References Cited

U.S. PATENT DOCUMENTS

| 5,629,337 | A | * | 5/1997 | Gray | 514/443 |
| 6,071,949 | A | | 6/2000 | Mulshine et al. | |
| 6,479,546 | B1 | | 11/2002 | Holman et al. | |
| 6,756,399 | B2 | | 6/2004 | Mulshine et al. | |
| 7,674,811 | B2 | | 3/2010 | Verma et al. | |
| 2003/0147813 | A1 | * | 8/2003 | Lyons | 424/45 |
| 2006/0019939 | A1 | * | 1/2006 | Adams et al. | 514/183 |
| 2007/0161546 | A1 | * | 7/2007 | King | 514/8 |
| 2008/0125440 | A1 | | 5/2008 | Cai et al. | |

FOREIGN PATENT DOCUMENTS

WO    WO95/24894    9/1995
WO    WO2007/087250    8/2007

OTHER PUBLICATIONS

Steele et al. "Lipoxygenase Inhibitors as Potential Cancer Chemopreventives", CancerEpid.Biom.Prev., 1999, vol. 8, No. 5, pp. 467-483.*

Steele, V. et al., Lipoxygenase Inhibitors as Potential Cancer Chemopreventives, *Cancer Epidemiology, Biomarkers and Prevention*, 8: 467-83, 1999.
West, M. et al., The arachidonic acid 5-lipoxygenase inhibitor nordihydroguaiaretic acid inhibits necrosis factor α activation of microglia and extends survival of G93A-SOD1 transgenic mice, *Journal of Neurochemisty*, 91: 133-43, 2004.
Chen, Y. et al., The Alox5 gene is a novel therapeutic target in cancer stem cells of chronic myeloid leukemia, *Cell Cycle*, 8(21): 3488-92, Nov. 1, 2009.
Chen, Y. et al., Loss of the Alox5 gene impairs leukemia stem cells and prevents chronic myeloid leukemia, *Nature Genetics*, 41(7): 783-92, Jul. 2009.
Steele, V. et al., Potential use of lipoxygenase inhibitors for cancer chemoprevention, *Exp Opin Invest Drugs*, 9(9): 2121-2138, 2000.
Ruiz, J. et al., QSAR Study of Dual Cyclooxygenase and 5-Lipoxygenase Inhibitors 2,6-di-tert-Butylphenol Derivatives, *Bioorganic & Medicinal Chemistry*, 11:4207-4216, 2003.
Bell, R. et al., Preclinical and Clinical Activity of Zileuton and A-78773, *Ann N Y Acad Sci*,. 696:205-15, Nov. 30, 1993.
Tsukada 1986, Arachidonate 5-Lipoxygenase Inhibitors Show Potent Antiproliferative Effects on Human Leukemia Cell Lines, *Biochemical and Biophysical Research Communications*, 140(3): 832-36, 1986.
Romano, M., et al., Cyclooxygenase-2 and 5-lipoxygenase converging functions on cell proliferation and tumor angiogenesis: implications for cancer therapy, *The FASEB Journal*, 17: 1986-1995, 2003.
Sullivan, C. et al, Targeted therapy of chronic myeloid leukemia, *Biochemical Pharmacology*, 80(5): 584-591, Sep. 1, 2010.
Vareed et al., Pharmacokinetics of Curcumin Conjugate Metabolites in Healthy Human Subjects, *Cancer Epidemiol Biomarkers Prev*, 17(6); 1411, Jun. 2008.
Chen, Y. et al., A tumor suppressor function of the Msr1 gene in leukemia stem cells of chronic myeloid leukemia, *Blood*, 118(2): 390-400, Jul. 14, 2011.
Peng, C. et al., LSK derived LSK—cells have a high apoptotic rate related to survival regulation of hematopoietic and leukemic stem cells, *PLoS ONE*, 7(6), Jun. 4, 2012, Article No. e38614.

(Continued)

*Primary Examiner* — James D Anderson
*Assistant Examiner* — Stephanie Springer
(74) *Attorney, Agent, or Firm* — Gifford, Krass, Sprinkle, Anderson & Citkowski, P.C.

(57) ABSTRACT

Methods of treating a subject having, or at risk of having, a myeloproliferative disorder are provided according to embodiments of the present invention which include administering a therapeutically effective amount of an arachidonate 5-lipoxygenase (5-LO) inhibitor to the subject. Combinations of therapeutic agents are administered according to embodiments of the present invention. In some embodiments, two or more 5-LO inhibitors are administered to a subject to treat a myeloproliferative disorder. In further embodiments, at least one 5-LO inhibitor and at least one additional therapeutic agent are administered to a subject to treat a myeloproliferative disorder. Methods of inhibiting leukemia stem cells are provided according to embodiments of the present invention which include contacting leukemia stem cells with an effective amount of an arachidonate 5-lipoxygenase inhibitor.

9 Claims, 31 Drawing Sheets

(56) References Cited

OTHER PUBLICATIONS

Al Baghdadi, T. et al. Novel combination treatments targeting chronic myeloid leukemia stem cells (Review), *Clinical Lymphoma, Myeloma and Leukemia*, 12(2): 94-105, Apr. 2012.

Anderson, K. et al., Induction of Apoptosis in Blood Cells from a Patient with Acute Myelogenous Leukemia by SC41661A, a Selective Inhibitor of 5-Lipoxygenase, *Prostaglandins Leukotrienes and Essential Fatty Acids*, 48: 323-26, 1993.

Anderson, K. et al., An in Vivo Inhibitor of 5-Lipoxygenase, MK886, at Micromolar Concentration Induces Apoptosis in U937 and CML Cells, *Anticancer Research*, 16: 2589-600, 1996.

Anderson, K. et al., Selective Inhibitors of 5-Lipoxygenase Reduce CML Blast Cell Proliferation and Induce Limited Differentiation and Apoptosis, *Leukemia Research*, 19(11): 789-801, 1995.

Stenke, L. et al., Elevated white blood cell synthesis of leukotriene C4 in chronic myelogenous leukaemia but not in polycythaemia vera, *British Journal of Hematology*, 74: 257-63, 1990.

* cited by examiner

```
                           SEQUENCE LISTING

<160> NUMBER OF SEQ ID NOS: 8

<210> SEQ ID NO 1
<211> LENGTH: 1854
<212> TYPE: DNA
<213> ORGANISM: Homo sapiens

<400> SEQUENCE: 1
atgccctcct acacggtcac cgtggccact ggcagccagt ggttcgccgg cactgacgac       60
tacatctacc tcagcctcgt gggctcggcg ggctgcagcg agaagcacct gctggacaag      120
cccttctaca acgacttcga gcgtggcgcg gtggattcat acgacgtgac tgtggacgag      180
gaactgggcg agatccagct ggtcagaatc gagaagcgca agtactggct gaatgacgac      240
tggtacctga agtacatcac gctgaagacg ccccacgggg actacatcga gttcccctgc      300
taccgctgga tcaccggcga tgtcgaggtt gtcctgaggg atggacgcgc aaagttggcc      360
cgagatgacc aaattcacat tctcaagcaa caccgacgta agaactgga aacacggcaa      420 aaacaatatc gatggatgga gtggaaccct ggcttcccct tgagcatcga tgccaaatgc      480
cacaaggatt taccccgtga tatccagttt gatagtgaaa aaggagtgga ctttgttctg      540
aattactcca aagcgatgga gaacctgttc atcaaccgct tcatgcacat gttccagtct      600
tcttggaatg acttcgccga ctttgagaaa atctttgtca agatcagcaa cactatttct      660
gagcgggtca tgaatcactg gcaggaagac ctgatgtttg gctaccagtt cctgaatggc      720
tgcaaccctg tgttgatccg gcgctgcaca gagctgcccg agaagctccc ggtgaccacg      780
gagatggtag agtgcagcct ggagcggcag ctcagcttgg agcaggaggt ccagcaaggg      840
aacattttca tcgtggactt tgagctgctg gatggcatcg atgccaacaa aacagacccc      900
tgcacactcc agttcctggc cgctcccatc tgcttgctgt ataagaacct ggccaacaag      960
attgtcccca ttgccatcca gctcaaccaa atcccgggag atgagaaccc tatttttcctc     1020 ccttcggatg caaaatacga ctggcttttg gccaaaatct gggtgcgttc cagtgacttc     1080
cacgtccacc agaccatcac ccaccttctg cgaacacatc tggtgtctga ggttttttggc     1140 attgcaatgt accgccagct gcctgctgtg cacccccattt tcaagctgct ggtggcacac     1200
gtgagattca ccattgcaat caacaccaag gcccgtgagc agctcatctg cgagtgtggc     1260
ctctttgaca aggccaacgc cacagggggc ggtgggcacg tgcagatggt gcagagggcc     1320
atgaaggacc tgacctatgc ctccctgtgc tttcccgagg ccatcaaggc ccggggcatg     1380
gagagcaaag aagacatccc ctactacttc taccgggacg acgggctcct ggtgtgggaa     1440
gccatcagga cgttcacggc cgaggtggta gacatctact acgagggcga ccaggtggtg     1500
gaggaggacc cggagctgca ggacttcgtg aacgatgtct acgtgtacgg catgcgggc     1560 cgcaagtcct caggcttccc caagtcggtc aagagccggg agcagctgtc ggagtacctg     1620
accgtggtga tcttccaccg ctccgcccag cacgccgcgg tcaacttcgg ccagctgttc     1680
ctgggcatgt acccagaaga gcattttatc gagaagcctg tgaaggaagc catggcccga     1740
ttccgcaaga acctcgaggc cattgtcagc gtgattgctg agcgcaacaa gaagaagcag     1800
```
ctgccatatt actacttgtc cccagaccgg attccgaaca gtgtggccat ctga       1854

<210> SEQ ID NO 2
<211> LENGTH: 617
<212> TYPE: PRT
<213> ORGANISM: Homo sapiens

<400> SEQUENCE: 2

Met Pro Ser Tyr Thr Val Thr Val Ala Thr Gly Ser Gln Trp Phe Ala
1               5                   10                  15

Gly Thr Asp Asp Tyr Ile Tyr Leu Ser Leu Val Gly Ser Ala Gly Cys
            20                  25                  30

Ser Glu Lys His Leu Leu Asp Lys Pro Phe Tyr Asn Asp Phe Glu Arg
        35                  40                  45

Gly Ala Val Asp Ser Tyr Asp Val Thr Val Asp Glu Glu Leu Gly Glu
    50                  55                  60

Ile Gln Leu Val Arg Ile Glu Lys Arg Lys Tyr Trp Leu Asn Asp Asp
65                  70                  75                  80

Trp Tyr Leu Lys Tyr Ile Thr Leu Lys Thr Pro His Gly Asp Tyr Ile
                85                  90                  95

Glu Phe Pro Cys Tyr Arg Trp Ile Thr Gly Asp Val Glu Val Val Leu
            100                 105                 110

Arg Asp Gly Arg Ala Lys Leu Ala Arg Asp Asp Gln Ile His Ile Leu
        115                 120                 125

Lys Gln His Arg Arg Lys Glu Leu Glu Thr Arg Gln Lys Gln Tyr Arg
    130                 135                 140

Trp Met Glu Trp Asn Pro Gly Phe Pro Leu Ser Ile Asp Ala Lys Cys
145                 150                 155                 160

His Lys Asp Leu Pro Arg Asp Ile Gln Phe Asp Ser Glu Lys Gly Val
                165                 170                 175

Asp Phe Val Leu Asn Tyr Ser Lys Ala Met Glu Asn Leu Phe Ile Asn
            180                 185                 190

Arg Phe Met His Met Phe Gln Ser Ser Trp Asn Asp Phe Ala Asp Phe
        195                 200                 205

Glu Lys Ile Phe Val Lys Ile Ser Asn Thr Ile Ser Glu Arg Val Met
    210                 215                 220

Asn His Trp Gln Glu Asp Leu Met Phe Gly Tyr Gln Phe Leu Asn Gly
225                 230                 235                 240

Cys Asn Pro Val Leu Ile Arg Arg Cys Thr Glu Leu Pro Glu Lys Leu
                245                 250                 255

Pro Val Thr Thr Glu Met Val Glu Cys Ser Leu Glu Arg Gln Leu Ser
            260                 265                 270

Leu Glu Gln Glu Val Gln Gln Gly Asn Ile Phe Ile Val Asp Phe Glu
        275                 280                 285

Leu Leu Asp Gly Ile Asp Ala Asn Lys Thr Asp Pro Cys Thr Leu Gln
    290                 295                 300

Phe Leu Ala Ala Pro Ile Cys Leu Leu Tyr Lys Asn Leu Ala Asn Lys
305                 310                 315                 320

Ile Val Pro Ile Ala Ile Gln Leu Asn Gln Ile Pro Gly Asp Glu Asn
                325                 330                 335

Pro Ile Phe Leu Pro Ser Asp Ala Lys Tyr Asp Trp Leu Leu Ala Lys
            340                 345                 350

Ile Trp Val Arg Ser Ser Asp Phe His Val His Gln Thr Ile Thr His
        355                 360                 365

Leu Leu Arg Thr His Leu Val Ser Glu Val Phe Gly Ile Ala Met Tyr

```
                370             375             380
Arg Gln Leu Pro Ala Val His Pro Ile Phe Lys Leu Leu Val Ala His
385                 390                 395                 400

Val Arg Phe Thr Ile Ala Ile Asn Thr Lys Ala Arg Glu Gln Leu Ile
                405                 410                 415

Cys Glu Cys Gly Leu Phe Asp Lys Ala Asn Ala Thr Gly Gly Gly Gly
            420                 425                 430

His Val Gln Met Val Gln Arg Ala Met Lys Asp Leu Thr Tyr Ala Ser
            435                 440                 445

Leu Cys Phe Pro Glu Ala Ile Lys Ala Arg Gly Met Glu Ser Lys Glu
        450                 455                 460

Asp Ile Pro Tyr Tyr Phe Tyr Arg Asp Asp Gly Leu Leu Val Trp Glu
465                 470                 475                 480

Ala Ile Arg Thr Phe Thr Ala Glu Val Val Asp Ile Tyr Tyr Glu Gly
                485                 490                 495

Asp Gln Val Val Glu Asp Pro Glu Leu Gln Asp Phe Val Asn Asp
            500                 505                 510

Val Tyr Val Tyr Gly Met Arg Gly Arg Lys Ser Ser Gly Phe Pro Lys
            515                 520                 525

Ser Val Lys Ser Arg Glu Gln Leu Ser Glu Tyr Leu Thr Val Val Ile
        530                 535                 540

Phe Thr Ala Ser Ala Gln His Ala Ala Val Asn Phe Gly Gln Leu Phe
545                 550                 555                 560

Leu Gly Met Tyr Pro Glu Glu His Phe Ile Glu Lys Pro Val Lys Glu
                565                 570                 575

Ala Met Ala Arg Phe Arg Lys Asn Leu Glu Ala Ile Val Ser Val Ile
            580                 585                 590

Ala Glu Arg Asn Lys Lys Lys Gln Leu Pro Tyr Tyr Leu Ser Pro
        595                 600                 605

Asp Arg Ile Pro Asn Ser Val Ala Ile
    610                 615

<210> SEQ ID NO 3
<211> LENGTH: 23
<212> TYPE: DNA
<213> ORGANISM: artificial
<220> FEATURE:
<223> OTHER INFORMATION: primer for RT-PCR of beta-catenin

<400> SEQUENCE: 3
aacagggtgc tattccacga cta                                           23

<210> SEQ ID NO 4
<211> LENGTH: 18
<212> TYPE: DNA
<213> ORGANISM: artificial
<220> FEATURE:
<223> OTHER INFORMATION: primer for RT-PCR of beta-catenin

<400> SEQUENCE: 4
tgtgaacgtc ccgagcaa                                                 18

<210> SEQ ID NO 5
<211> LENGTH: 20
<212> TYPE: DNA
<213> ORGANISM: artificial
<220> FEATURE:
<223> OTHER INFORMATION: primer for RT-PCR of GATA-1

<400> SEQUENCE: 5
```

```
-continued actgtggagc aacggctact                                                        20

<210> SEQ ID NO 6
<211> LENGTH: 20
<212> TYPE: DNA
<213> ORGANISM: artificial
<220> FEATURE:
<223> OTHER INFORMATION: primer for RT-PCR of GATA-1

<400> SEQUENCE: 6
tccgccagag tgttgtagtg                                                        20

<210> SEQ ID NO 7
<211> LENGTH: 20
<212> TYPE: DNA
<213> ORGANISM: artificial
<220> FEATURE:
<223> OTHER INFORMATION: primer for RT-PCR of FOG-1

<400> SEQUENCE: 7
catagaggag cccccaagtc                                                        20

<210> SEQ ID NO 8
<211> LENGTH: 20
<212> TYPE: DNA
<213> ORGANISM: artificial
<220> FEATURE:
<223> OTHER INFORMATION: primer for RT-PCR of FOG-1

<400> SEQUENCE: 8
ggctgcctct tcttcctttt                                                        20
```

METHODS AND COMPOSITIONS RELATING TO HEMATOLOGIC MALIGNANCIES

REFERENCE TO RELATED APPLICATION

This application is the United States national phase application of PCT/US2010/032416, filed Apr. 26, 2010, which claims priority from U.S. Provisional Patent Application Ser. No. 61/172,447, filed Apr. 24, 2009, the entire content of both of which is incorporated herein by reference.

GOVERNMENT SUPPORT

This invention was made with government support under Grant No. CA122142 awarded by the National Institutes of Health. The government has certain rights in the invention.

BACKGROUND OF THE INVENTION

Myeloproliferative disorders (MPD) are conditions where too many blood cells are produced. MPDs include: Childhood Acute Myeloid Leukemia and Other myeloid malignancies such as childhood myelodysplastic syndromes; Acute Myeloid Leukemia (AML); Chronic Myelogenous Leukemia (CML); Chronic Myeloproliferative Disorders such as Polycythemia Vera, Chronic Idiopathic Myelofibrosis, Essential Thrombocythemia, Chronic Neutrophilic Leukemia, and Chronic Eosinophilic Leukemia; Myelodysplastic Syndromes such as refractory anemia, refractory anemia with excess blasts, refractory anemia with ringed sideroblasts, refractory cytopenia with multilineage dysplasia, unclassifiable myelodysplastic syndrome, myelodysplastic syndrome associated with del (5q), de novo Myelodysplastic Syndrome, secondary Myelodysplastic Syndrome and "previously treated" Myelodysplastic Syndrome; and Myelodysplastic/Myeloproliferative Neoplasms such as Chronic Myelomonocytic Leukemia, Juvenile Myelomonocytic Leukemia (JMML), Atypical Chronic Myeloid Leukemia (aCML) and Myelodysplastic/Myeloproliferative Neoplasm, unclassifiable.

Chronic Myelogenous Leukemia (CML), also known as chronic myeloid leukemia or chronic granulocytic leukemia (CGL), is a malignancy of a hematopoietic stem cells characterized by a cytogenetic abnormality, the Philadelphia chromosome in 95% of the patients (Druker, 2008; Faderl et al., 1999a; Faderl et al., 1999b). It accounts for 15-20% of all cases of adult leukemia.

CML is a progressive, uniformly fatal disease in untreated patients. It is often divided into three phases: a chronic phase lasting three to six years; an acute or accelerated phase lasting three to six months; and a final blast crisis phase. The progression of the disease to blast crisis results in rapid death due to infections, bleeding and leukemic organ infiltration.

The Philadelphia chromosome or Philadelphia translocation is a specific cytogenetic abnormality that is the hallmark of CML, but can also be found in other myeloproliferative disorders, including ALL and AML. It results from a reciprocal chromosomal translocation between chromosome 9 and 22: t(9; 22)(q34; q11). The translocation produces a fusion gene, termed BCR-ABL (Ren, 2005), created by the translocation of the c-ABL proto-oncogene form its normal position on chromosome 9 chromosome 22. The region on chromosome 22 was named breakpoint cluster region (BCR) and spans 5.3 kilobases. ABL is a non-receptor tyrosine kinase that is expressed in most tissues and BCR is a signaling protein. The BCR-ABL fusion has constitutively activated tyrosine-kinase activity, which is essential for the transforming activity and leukemogenicity. Depending on the chromosomal break point different forms of BCR-ABL protein with different molecular weights, p185 BCR-ABL (p185 BCR-ABL is also known as p190 BCR-ABL), p210 BCR-ABL and p230 BCR-ABL, are generated.

Ph$^+$ leukemias are induced by the chimeric BCR-ABL oncogene resulting from the fusion of the BCR gene to the N-terminus of the c-ABL gene. The BCR gene, on chromosome 22, breaks either at exon 1, exon 12/13, or exon 19 and fuses to the c-ABL gene on chromosome 9 to form, respectively, three types of BCR-ABL chimeric gene: P190 (also known as P185), P210, or P230. The three forms of BCR-ABL contain the same portion of the c-ABL gene but different lengths of the BCR gene. BCR comprises three domains: a coiled-coil structure, serine-rich sequences, and the C-terminal domain. P190 contains the first two domains of BCR, and P210 and P230 also contain some and the majority of the C-terminal domain of BCR, respectively. The C-terminal domain that is lacking in the P190 BCR protein comprises Pleckstrin homology (PH) and dbl-like domains (present in both P210 and P230). P230 contains in addition the calcium-phosphate biding (CalB) domain and the first third of the domain associated with GTPase activating activity for p21rac (GAP$^{rac}$) of the BCR region.

In humans, each of the three forms of the BCR-ABL oncogene is associated with a distinct type of leukemia. The P190 form is most often present in B-ALL but only rarely in CML (Deininger M W et al., Blood (2000) 96:3343-56). P210 predominates in CML and in some acute lymphoid (Deininger et al. supra) and myeloid leukemias in CML blast crisis. P230 was found in a very mild form of CML and in a few patients with typical CML (Pane F et al., Blood (1996) 88:2410-2414; Wilson et al., Blood (1997) 89:3064; Mittre et al., Blood (1997) 89:4239; Briz et al., Blood (1997) 90:5024). Lymphoid blast crisis of CML and Ph$^+$ B-ALL account for 20 percent of adults and 5 percent of children with acute B-lymphoid leukemia that is caused by BCR-ABL and other oncogenes. Among those patients with BCR-ABL-induced B-ALL, 50 percent of adults and 20 percent of children carry P210 form of BCR-ABL and the rest of the patients carry the P190 form (Deininger et al. supra; Sawyers C L N. Engl. J. Med. (1999) 340:1330-1340; Druker B J et al., N. Engl. J. Med. (2001) 344:1038-1042). Thus, both P190 and P210 can induce Ph$^+$ B-ALL, and only P210 is a major inducer of CML.

Transition from chronic phase to blast crisis is a devastating process in Ph$^+$ leukemia. While in most patients, chronic phase CML can be temporarily controlled with cytotoxic drugs such as imatinib, the disease can progress from chronic phase to accelerated phase or blast crisis within several years of diagnosis. Although the mechanism underlying the disease progression remains unclear, additional genetic alterations seem to play a role in this process. Mutations in the BCR-ABL fusion gene, of tumor suppressor genes, including the retinoblastoma gene (Rb), p16, and p53, have been found to be associated with CML blast crisis patients (Towatari M et al., Blood (1991) 78:2178-2181; Sill H et al., Blood (1995) 85:2013-2016; Feinstein E et al., Proc. Natl. Acad. Sci. U.S.A. (1991) 88:6293-6297). Several studies have shown that BCR-ABL deregulates the functions of DNA repair-related genes. For example, BCR-ABL down-regulates expression of the DNA repair enzyme DNA-PKcs (Deutsch E et al., Blood (2001) 97:2084-90). P210BCR-ABL may interact with the Xeroderma pigmentosum group B protein, which could lead to the impairment of DNA repair function (Takeda N et al., Proc. Natl. Acad. Sci. USA (1999) 96:203-207). Expression of two other genes related to genetic stability, BRCA-1 and RAD51, is also deregulated by BCR-ABL (Canitrot Y et al., Oncogene (1999) 18:2676-2680; Slupianek A et al., *Mol Cell* (2001) 8:795-806). BCR-ABL can also cause over-expression and increased activity of the error-prone polymerase β, leading to an increased mutagenesis (Canitrot et al. supra).

The field of stem cell biology has stimulated cancer biologists to identify and characterize cancer stem cells in tumors. Such cancer stem cells are rare but are critical for the formation and growth of tumors (Jordan et al., 2006; Pardal et al., 2003; Reya et al., 2001; Rossi et al., 2008; Singh et al., 2003; Wang and Dick, 2005), and are thought to be required for the initiation of tumors (Al-Hajj et al., 2003).

For leukemia such cancer stem cells are called leukemic or leukemia stem cells (LSCs). The concept of LSCs was first described in the 1970s (Park, C. H. et al., J. Natl. Cancer Inst., 46: 411-422), although the existence of LSC was demonstrated only more recently (Blair, A., et al., 1997, Blood 89:3104-3112 and Bonnet, D. et al., 1997 Nature Med., 3: 730-737). It is currently thought that a few LSCs are sufficient to induce leukemia, accumulate mutations and can give rise to abnormal new hematopoietic tissues. LSCs similar to normal hematopoietic stem cells do not proliferate at a high rate.

The responsiveness of patients to current treatments, particularly treatment with kinase inhibitors, is often transient since patients develop resistance to these drugs.

Thus, while some treatments have been developed to address myeloproliferative disorders, there is a continuing need for therapeutic methods and compositions to treat myeloproliferative disorders. In particular, new treatments are required in view of resistance to current treatments in patients. In particular, there is a continuing need for therapeutic methods and compositions to treat CML.

SUMMARY OF THE INVENTION

Methods of treating a subject having, or at risk of having, a myeloproliferative disorder are provided according to embodiments of the present invention which include administering a therapeutically effective amount of an arachidonate 5-lipoxygenase (5-LO) inhibitor to the subject.

An administered 5-LO inhibitor is N-[1-(1-benzothien-2-yl)ethyl]-N-hydroxyurea, also known as zileuton, in embodiments of methods of the present invention.

Combinations of therapeutic agents are administered according to embodiments of the present invention. In some embodiments, two or more 5-LO inhibitors are administered to a subject to treat a myeloproliferative disorder. In further embodiments, at least one 5-LO inhibitor and at least one additional therapeutic agent are administered to a subject to treat a myeloproliferative disorder.

The at least one additional therapeutic agent is an anticancer agent according to embodiments of the present invention including, without limitation, a tyrosine kinase inhibitor, a 5-lipoxygenase-activating protein inhibitor, a src kinase inhibitor, an aurora kinase inhibitor, an Hsp90 inhibitor, an anti-metabolite, an alkylating agent, a steroid, interferon alpha 2b; or a combination of any two or more thereof.

In some embodiments, methods of the present invention include administering at least a therapeutically effective dose of a 5-LO inhibitor and a therapeutically effective dose of a tyrosine kinase inhibitor to the subject.

In some embodiments, the tyrosine kinase inhibitor is a bcr-abl tyrosine kinase inhibitor. For example, the bcr-abl tyrosine kinase inhibitor is 4-[(4-methylpiperazin-1-yl)methyl]-N-[4-methyl-3-[(4-pyridin-3-ylpyrimidin-2-yl)amino]-phenyl]-benzamide, also known as imatinib, in embodiments of methods of the present invention. Imatinib is preferably included as a pharmaceutically acceptable salt, particularly as imatinib mesylate.

In certain embodiments, methods of the present invention include administering at least a therapeutically effective dose of a 5-LO inhibitor and a therapeutically effective dose of an ALOX5-activating protein (FLAP) inhibitor. An administered FLAP inhibitor is 1-[(4-chlorophenyl)methyl]3-[(1,1-dimethylethyl)thio]-α, α-dimethyl-5-(1-methylethyl)-1H-indole-2-propanoic acid, also known as MK886, in embodiments of methods of the present invention.

In certain embodiments, methods of the present invention include administering at least a therapeutically effective dose of a 5-LO inhibitor and a therapeutically effective dose of a src kinase inhibitor. For example, the src kinase inhibitor is N-(2-chloro-6-methylphenyl)-2-[[6-[4-(2-hydroxyethyl)-1-piperazinyl]-2-methyl-4-pyrimidinyl]amino]-5-thiazolecarboxamide monohydrate, also known as dasatinib, in embodiments of methods of the present invention.

In certain embodiments, methods of the present invention include administering at least a therapeutically effective dose of a 5-LO inhibitor and a therapeutically effective dose of an aurora kinase inhibitor. For example, the aurora kinase inhibitor is N-[5-(2-Methoxy-2-phenyl-acetyl)-1,4,5,6-tetrahydro-pyrrolo[3,4-c]pyrazol-3-yl]-4-(4-methyl-piperazin-1-yl)-benzamide, also known as danusertib, in embodiments of methods of the present invention.

In certain embodiments, methods of the present invention include administering at least a therapeutically effective dose of a 5-LO inhibitor and a therapeutically effective dose of a chaperone inhibitor. For example, the chaperone inhibitor is a heat shock protein 90 inhibitor in embodiments of methods of the present invention.

In certain embodiments, methods of the present invention include administering at least a therapeutically effective dose of a 5-LO inhibitor and a therapeutically effective dose of a protein synthesis inhibitor. For example, the protein synthesis inhibitor is 1-[(1S,3aR,14bS)-2-methoxy-1,5,6,8,9,14b-hexahydro-4H-cyclopenta[a][1,3]dioxolo[4,5-h]pyrrolo[2,1-b][3]benzazepin-1-yl]-4-methyl(2R)-2-hydroxy-2-(4-hydroxy-4-methylpentyl)butanedioate, also known as omacetaxine mepesuccinate, in embodiments of methods of the present invention.

According to embodiments of methods of the present invention, patients with symptoms of a myeloproliferative disorder are identified and treated with a therapeutically effective dose of the 5-lipoxygenase (5-LO) inhibitor GSK2190915 and a therapeutically effective dose of imatinib.

According to embodiments of methods of the present invention, patients with symptoms of a myeloproliferative disorder are identified and treated with a therapeutically effective dose of the 5-lipoxygenase (5-LO) inhibitor GSK2190915 and a therapeutically effective dose of the dual kinase inhibitor dasatinib.

According to embodiments of methods of the present invention, patients with symptoms of a myeloproliferative disorder are identified and treated with a therapeutically effective dose of the 5-lipoxygenase (5-LO) inhibitor VIA-2291.

According to embodiments of methods of the present invention, patients with symptoms of a myeloproliferative disorder are identified and treated with a therapeutically effective dose of the 5-lipoxygenase (5-LO) inhibitor licofelone (ML3000) and a therapeutically effective dose of the dual kinase inhibitor dasatinib.

According to embodiments of methods of the present invention, patients with symptoms of a myeloproliferative disorder are identified and treated with a therapeutically effective dose of the 5-lipoxygenase (5-LO) inhibitor curcumin and a therapeutically effective dose of imatinib.

According to embodiments of methods of the present invention, patients with symptoms of CML are identified and treated with a therapeutically effective dose of the 5-lipoxygenase (5-LO) inhibitor zileuton and a therapeutically effective dose of the Hsp90 inhibitor IPI-504.

According to embodiments of methods of the present invention, patients with symptoms for CML are identified and treated with a therapeutically effective dose of the 5-lipoxygenase (5-LO) inhibitor zileuton and a therapeutically effective dose of the heat shock protein 90 (Hsp90) inhibitor tanespimycin.

According to embodiments of methods of the present invention, patients with symptoms of CML are identified and treated with a therapeutically effective dose of the 5-lipoxygenase (5-LO) inhibitor zileuton and a therapeutically effective dose of the dual kinase inhibitor dasatinib.

According to embodiments of methods of the present invention, patients with symptoms of CML are identified and treated with a therapeutically effective dose of the 5-lipoxygenase (5-LO) inhibitor zileuton and a therapeutically effective dose of the heat shock protein 90 (Hsp90) inhibitor STA-9090.

According to embodiments of methods of the present invention, patients with symptoms of CML are identified and treated with a therapeutically effective dose of the 5-lipoxygenase (5-LO) inhibitor VIA-2291 (Atreleuton) and a therapeutically effective dose of the dual kinase inhibitor dasatinib.

According to embodiments of methods of the present invention, patients with symptoms of CML are identified and treated with a therapeutically effective dose of the 5-lipoxygenase (5-LO) inhibitor GSK2190915 and a therapeutically effective dose of imatinib.

According to embodiments of methods of the present invention, patients with symptoms for CML are identified and treated with the 5-lipoxygenase (5-LO) inhibitor GSK2190915 and the dual kinase inhibitor dasatinib.

According to embodiments of methods of the present invention, patients with symptoms of CML are identified and treated with a therapeutically effective dose of the 5-lipoxygenase (5-LO) inhibitor VIA-2291.

According to embodiments of methods of the present invention, patients with symptoms of CML are identified and treated with a therapeutically effective dose of the 5-lipoxygenase (5-LO) inhibitor licofelone (ML3000) and a therapeutically effective dose of the dual kinase inhibitor dasatinib.

According to embodiments of methods of the present invention, patients with symptoms of CML are identified and treated with a therapeutically effective dose of the 5-lipoxygenase (5-LO) inhibitor curcumin and a therapeutically effective dose of imatinib.

Methods of inhibiting leukemia stem cells are provided according to embodiments of the present invention which include contacting leukemia stem cells with an effective amount of an arachidonate 5-lipoxygenase inhibitor.

Methods of inhibiting leukemia stem cells are provided according to embodiments of the present invention wherein the leukemia stem cells are contacted with an effective amount of an arachidonate 5-lipoxygenase inhibitor in a subject having, or at risk of having, a myeloproliferative disorder.

Methods of inhibiting leukemia stem cells are provided according to embodiments of the present invention wherein the leukemia stem cells are isolated from a subject having, or at risk of having, a myeloproliferative disorder and contacted with the effective amount of an arachidonate 5-lipoxygenase inhibitor ex vivo.

Methods of inhibiting leukemia stem cells are provided according to embodiments of the present invention which include contacting leukemia stem cells with an effective amount of an arachidonate 5-lipoxygenase inhibitor wherein the arachidonate 5-lipoxygenase inhibitor is selected from the group consisting of: N-[1-(1-benzothien-2-yl)ethyl]-N-hydroxyurea (zileuton), atreleuton, BW-B 70C, darbufelone, licofelone, minocycline, tepoxalin, tebufelone, curcumin, DHDMBF, BF389, RJW63556, PGV20229, CI986, S2474, ZD2138, CJ-13,610, L-739,010, Wy-50295, TMK688, PEP03, GSK-2190915 and AZD-4407.

Methods are provided according to embodiments of the present invention for treating a subject having, or at risk of having, a myeloproliferative disorder where the subject is resistant to anti-cancer effects of a kinase inhibitor selected from: imatinib, dasatinib and nilotinib, wherein the methods include administering a therapeutically effective dose of a 5-LO inhibitor.

In particular embodiments of the present invention, the myeloproliferative disorder is a myeloproliferative disorder characterized by elevated ALOX5. In certain embodiments, the myeloproliferative disorder is a myeloproliferative disorder characterized by oncogene-mediated elevated ALOX5. Non-limiting examples of myeloproliferative disorders characterized by oncogene-mediated elevated ALOX5 include chronic myelogenous leukemia and Tel-PDGFR-beta-induced myeloid leukemia.

Methods are provided according to embodiments of the present invention for treating a myeloproliferative disorder in a subject having, or at risk of having, a myeloproliferative disorder which include detecting an abnormality selected from the group consisting of: a chromosomal abnormality associated with oncogene tyrosine kinase activity, a tyrosine kinase oncogene in a sample obtained from the subject and a combination thereof; and administering a therapeutically effective amount of a 5-LO inhibitor to the subject, thereby treating the myeloproliferative disorder.

Methods are provided according to embodiments of the present invention for treating a myeloproliferative disorder in a subject having, or at risk of having, a myeloproliferative disorder which include detecting an abnormality selected from the group consisting of: a chromosomal abnormality associated with oncogene tyrosine kinase activity, a tyrosine kinase oncogene in a sample obtained from the subject and a combination thereof; detecting elevated ALOX5 in a sample obtained from the subject; and administering a therapeutically effective amount of a 5-LO inhibitor to the subject, thereby treating the myeloproliferative disorder.

In particular embodiments, the tyrosine kinase oncogene is bcr-abl and/or Tel-PDGFR-beta.

Detecting elevated ALOX5 can include detecting an elevated level of ALOX5 expression, detecting an elevated level of ALOX5 activity, detecting an elevated level of an ALOX5 metabolite; or a combination of any of these.

In one embodiment, detecting an elevated level of an ALOX5 metabolite includes detection of LTB4 in a sample obtained from the subject. In one embodiment, detecting an elevated level of an ALOX5 metabolite includes detection of LTC4 in a sample obtained from the subject. The sample can be any type of biological sample, exemplified by blood, plasma and bone marrow.

Methods of treating a subject having, or at risk of having leukemia, are provided which include administering a therapeutically effective amount of a 5-LO inhibitor; and administering a therapeutically effective amount of a BCR-ABL inhibitor. Without wishing to be bound by theory, it is believed that the 5-LO inhibitor is effective to inhibit leukemia stem cells, such as CML-stem cells and the BCR-ABL inhibitor inhibits differentiated leukemia cells, thereby treating the leukemia.

Compositions are provided according to embodiments of the present invention which include a 5-LO inhibitor admixed with an additional therapeutic agent. In a particular embodiment, a composition of the present invention includes a 5-LO inhibitor admixed with a bcr-abl tyrosine kinase inhibitor. For example, a composition of the present invention includes N-[1-(1-benzothien-2-yl)ethyl]-N-hydroxyurea and imatinib mesylate.

Commercial packages are provided according to embodiments of the present invention for preferentially inhibiting a myeloproliferative disorder in a subject having, or at risk of having, a myeloproliferative disorder which include a 5-LO inhibitor. Optionally, one or more auxiliary components are included in inventive commercial packages, such as pharmaceutically acceptable carrier such as a buffer, a diluent or a reconstituting agent.

Optionally, a commercial package according to embodiments of the present invention includes an additional therapeutic agent, such as a kinase inhibitor, a FLAP inhibitor, an Hsp90 inhibitor, an anti-metabolite, an alkylating agent, a steroid, interferon alpha 2b; and a combination of any two or more thereof. In a further option a composition of the present invention is included in a commercial package.

DETAILED DESCRIPTION OF THE INVENTION

Figure 1:
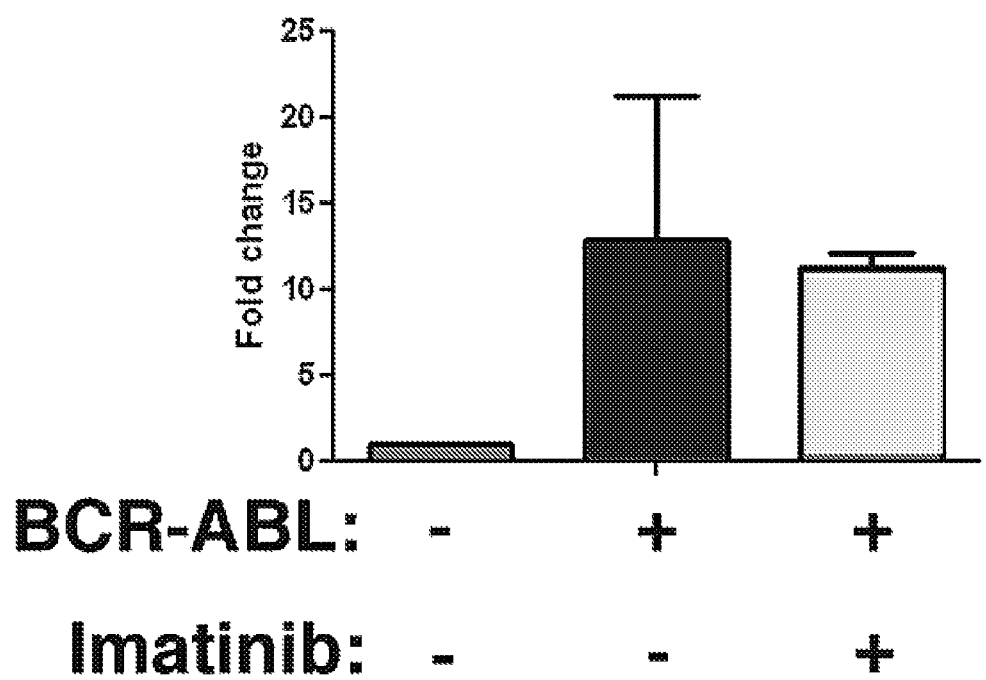
FIG. 1 is a graph showing that expression of the Alox5 gene is up-regulated by BCR-ABL in CML stem cells (CML-SCs) as compared to the sorted $GFP^+Lin^-c-Kit^+Sca-1^+$ cells that did not express BCR-ABL (BCR-ABL$^-$), and this up-regulation is not prevented by imatinib treatment (Imatinib+)

The singular terms "a," "an," and "the" include plural referents unless the context clearly indicates otherwise.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, Pa., 2003; Herdewijn, P. (Ed.), Oligonucleotide Synthesis: Methods and Applications, Methods in Molecular Biology, Humana Press, 2004; Chu, E. and Devita, V. T., Eds., Physicians' Cancer Chemotherapy Drug Manual, Jones & Bartlett Publishers, 2005; J. M. Kirkwood et al., Eds., Current Cancer Therapeutics, 4th Ed., Current Medicine Group, 2001; Remington: The Science and Practice of Pharmacy, Lippincott Williams & Wilkins, 21st Ed., 2006; L. V. Allen, Jr. et al., Ansel's Pharmaceutical Dosage Forms and Drug Delivery Systems, 8th Ed., Philadelphia, Pa.: Lippincott, Williams & Wilkins, 2004; and L. Brunton et al., Goodman & Gilman's The Pharmacological Basis of Therapeutics, McGraw-Hill Professional, 11th Ed., 2005.

Methods of Treatment

Methods of treating a subject having, or at risk of having, a myeloproliferative disorder are provided according to embodiments of the present invention, which include administering a therapeutically effective amount of a 5-LO inhibitor to the subject.

Subjects are identified as having, or at risk of having, a myeloproliferative disorder using well-known medical and diagnostic techniques. Exemplary medical and diagnostic techniques for identification of subjects are identified as having, or at risk of having, a myeloproliferative disorder are described herein and in Haferlach et al. 2008, Ann. Hematol., 87, 1-10).

In one embodiment, the invention provides methods for preventing the transition from chronic or accelerated phase leukemia to acute phase leukemia including administering to a subject a therapeutically effective amount of at least one 5-LO inhibitor.

In one embodiment, the invention provides methods for treating Philadelphia chromosome-positive (Ph$^+$) acute phase leukemia including administering to a subject a therapeutically effective amount of at least one 5-LO inhibitor. In particular embodiments, a therapeutically effective amount of an arachidonate 5-lipoxygenase inhibitor is administered to a subject having pre-acute phase Philadelphia chromosome-positive (Ph+) chronic myeloid leukemia, inhibiting the transition from the pre-acute phase to the acute phase.

In particular embodiments, myeloproliferative disorders treated in accordance with methods of the invention include myeloid leukemias, chronic myeloid leukemia (CML), acute myelogenous leukemia (AML), childhood acute myeloid leukemia, chronic myeloproliferative disorders, myelodysplastic/myeloproliferative neoplasms, myelodysplastic syndromes.

In an exemplary embodiment, the invention provides methods for preventing the transition from Ph$^+$ chronic myeloid leukemia (CML) to AML or ALL, especially, B-ALL.

In yet another embodiment, the invention provides methods for treating a subject suffering from Ph$^+$ leukemia that is resistant or insensitive to kinase inhibition therapy by administering to a subject a therapeutically effective amount of at least one 5-LO inhibitor, or a combination of at least one 5-LO inhibitor with a second therapeutic agent or treatment. Myeloproliferative disorders resistant or insensitive to kinase inhibition therapy that may be treated in accordance with the methods of the invention include CML. Myeloproliferative disorders resistant or insensitive to kinase inhibition therapy include myeloproliferative disorders associated with a genetic mutation in the kinase domain of BCR-ABL, amplification of the BCR-ABL gene, upregulation of multidrug resistance proteins, or functional inactivation of imatinib.

In a further embodiment, myeloproliferative disorders treated in accordance with methods of the invention are resistant or insensitive to kinase inhibition therapy and are characterized by the presence of one or more mutations in the BCR-ABL protein. It has been observed that patients treated with imatinib show a high relapse rate in advanced- and blast-crisis phase. In such patients a number of mutations have been identified in the ABL kinase domain, which result in drug resistance. The most prominent BCR-ABL mutation is in the amino acid residue 315, altering threonine to isoleucine (T315I). This T315I mutation is responsible for the resistance to imatinib, dasatinib and nilotinib treatment. In addition to the T315I mutation, the T315V and T315A (dasatinib only) mutations have been reported to be associated with resistance to imatinib, dasatinib and nilotinib treatment.

Other residues with frequent mutations in patients resistant to imatinib are Gly250 (G250A, G250E) Tyr253 (Y253H, Y253F), Glu255 (E255K, E255V), Val299 (V299L), Phe317 (F317L, F317V), Met351 (M351T) and Phe359 (F359A, F359C). (see Weisberg et al. 2007, Nat Rev Cancer 7(5):345-356).

Other mutations observed after imatinib treatment are M244V, L248V, Q252H, Q252R, E292K, F311I, F311L, M343T, E355G, V379I, L387M, M388L, H396R, H396P and F486S.

In patients treated with dasatinib, the following mutations have been reported in addition to the T315I and T315A mutation: L248V, Q252H, E292K, V299L, F317I, F317L, F317V and F317C.

In patients treated with nilotinib the most prevalent mutation is T315I and further mutations described are: G250E, Y253H, E255K, E292K, F359C, L384M and L387F.

BCR-ABL mutations associated with kinase resistance are well-known in the art along with methods of their detection, such as sequencing or PCR, in a subject to be treated, for example as described in U.S. Pat. No. 7,521,175 and Ou et al. 2008, Am. J. Hematol, 83-296-308). Further diagnostic companies, such as MolecularMD, Portland, Oreg., USA; DxS, a Qiagen company, Manchester, UK offer to perform such testing and provide kits.

In another exemplary embodiment, the myeloproliferative disorders are resistant and/or insensitive to treatment with imatinib mesylate or dasatinib or nilotinib. In another exemplary embodiment, the patients are intolerant to imatinib or dasatinib or nilotinib.

The term "resistant or insensitive to kinase inhibition therapy" refers to a subject suffering from a myeloproliferative disorder that does not respond to treatment with a kinase inhibitor. Subjects who are resistant or insensitive to kinase inhibition therapy may initially not respond to treatment with a kinase inhibitor or may develop an insensitivity/resistance during the course of treatment (e.g., the subject initially responds to treatment but later stops responding to the treatment). A subject does not respond to treatment with a kinase inhibitor when the subject manifests a worsening of symptoms during treatment, including, for example, a worsening of one or more of the following symptoms: an increase in the percentage of blasts and/or promyelocytes in the blood and/or bone marrow, hematologic progression (e.g., worsening of blood counts), cytogenetic evolution (e.g., development of new chromosomal abnormalities), fever, weight loss, night sweats, bone pain, constitutional symptoms, lymphadenopathy, leukemia cutis, central nervous system disease, and/or bleeding secondary to progressive thrombocytopenia. The term "resistant or insensitive to kinase inhibition therapy" also encompasses subjects intolerant of kinase inhibition therapy, such as subjects experiencing severe side effects of kinase inhibition therapy.

In another aspect, the invention provides methods for targeting LSCs present in myeloproliferative disorders, such as CML-SCs, and/or blocking such LSCs and/or reducing the survival and/or the self-renewal of such LSCs and/or affecting the differentiation of such LSCs.

In embodiments of the present invention methods are provided for targeting CML-SCs, and/or blocking CML-SCs and/or reducing the survival and/or the self-renewal of CML-SCs and/or affecting the differentiation of CML-SCs.

In an another embodiment, a myeloproliferative disorder treated in accordance with methods of the invention is characterized by a t(5; 12) (q33; p13) chromosomal translocation, resulting in a TEL-PDGFRB fusion gene in the subject having the myeloproliferative disorder.

"The terms "treating" and "treatment" used to refer to treatment of a myeloproliferative disorder in a subject include: preventing, inhibiting or ameliorating the myeloproliferative disorder in a subject, such as slowing progression of the myeloproliferative disorder and/or reducing or ameliorating a sign or symptom of the myeloproliferative disorder. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

One sign of a myeloproliferative disorder is presence of leukemia stem cells and embodiments of methods of the present invention include inhibition, such as reduction in number or activity, of leukemia stem cells. Without wishing to be bound by theoretical considerations, it is believed that leukemia stem cells, among other leukemia cells, are inhibited by 5-LO inhibitors and inhibition of the leukemia stem cells contributes to treatment of the myeloproliferative disorder. Inhibition of leukemia stem cells has beneficial therapeutic effects in a subject having, or at risk of having, a myeloproliferative disorder, including, but not limited to, inhibiting one or more symptoms of the myeloproliferative disorder and inhibiting blast crisis. Included in inhibition of one or more symptoms of the myeloproliferative disorder and inhibition of blast crisis is prevention of one or more symptoms of the myeloproliferative disorder and prevention of blast crisis.

The terms "5-lipoxygenase", "arachidonate 5-lipoxygenase", "5-LO", "Alox5" and "ALOX5" are used interchangeably. Other names for Alox5 also used in the art are 5-LOX, arachidonic acid 5-lipoxygenase, leukotriene A4 synthase and SLPG. The Entrez Gene Id for ALOX5 is 240.

The terms "leukemic stem cell," "leukemia stem cell," and "LSC" are used interchangeably and refer to a cancer stem cell found in leukemia, such as myeloproliferative disorders and CML, that is able to self-renew, differentiate, and proliferate, and capable of inducing myeloproliferative disorders, such as CML. Leukemic stem cells are known in the art and are described in Blair, A. et al., 1997, Blood, 89:3104-3112 and Bonnet, D. et al., 1997, Nature Med. 3: 730-737.

The terms "CML stem cell" and "CML-SC" are used interchangeably and refer to the cancer stem cell found in CML, that is able to self-renew, differentiate, and proliferate, and capable of inducing CML. CML stem cells are known in the art and are described in Stuart et al. 2009, Cell Cycle 1; 8(9):1338-43; Jamieson 2008, Hematology Am Soc Hematol Educ Program 1: 436-442 and Jorgensen and Holyoake 2007 Biochem Soc Trans 35(Pt 5):1347-51.

Methods of inhibiting leukemia stem cells are provided according to embodiments of the present invention which include contacting leukemia stem cells with an effective amount of an arachidonate 5-lipoxygenase inhibitor.

Methods of inhibiting leukemia stem cells are provided according to embodiments of the present invention wherein the leukemia stem cells are contacted with an effective amount of an arachidonate 5-lipoxygenase inhibitor in a subject having, or at risk of having, a myeloproliferative disorder.

Methods of inhibiting leukemia stem cells are provided according to embodiments of the present invention wherein the leukemia stem cells are isolated from a subject having, or at risk of having, a myeloproliferative disorder and contacted with the effective amount of an arachidonate 5-lipoxygenase inhibitor ex vivo.

Methods of inhibiting leukemia stem cells are provided according to embodiments of the present invention wherein the leukemia stem cells are CML stem cells and where the CML stem cells are contacted with an effective amount of an arachidonate 5-lipoxygenase inhibitor in a subject having, or at risk of having, a myeloproliferative disorder.

Methods of inhibiting leukemia stem cells are provided according to embodiments of the present invention wherein the leukemia stem cells are CML stem cells isolated from a subject having, or at risk of having, CML and where the CML stem cells are contacted with the effective amount of an arachidonate 5-lipoxygenase inhibitor ex vivo.

Leukemia stem cells are isolated from a subject using techniques well-known in the art, such as bone marrow isolation combined with FACS. The terms "isolated leukemia stem cells" and "isolated CML stem cells" refer to separation of the indicated stem cells from the usual environment in which they are found in a subject. The isolated stem cells are generally present in a bone marrow sample which can be returned to the subject's body following contacting the leukemia stem cells with the effective amount of an arachidonate 5-lipoxygenase inhibitor.

5-LO Inhibitors

The term "5-LO inhibitor" as used herein refers to any agent, protein, nucleic acid, small molecule or chemical that reduces the levels or activity of ALOX5.

The term "small molecule" refers to a compound, which has a molecular weight of less than about 5 kD, less than about 2.5 kD, less than about 1.5 kD, or less than about 0.9 kD. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides or polypeptides.

A 5-LO inhibitor included in inventive methods can be an antibody, an aptamer, an antisense oligonucleotide, a ribozyme or an inhibitory compound, such as an organic or inorganic inhibitory compound.

A 5-LO inhibitor inhibits ALOX5 activity in any of various ways including by inhibition of ALOX5 transcription, translation, or transport. Further, inhibition of ALOX5 activity includes inhibition of the functional activities of ALOX5, which include but are not limited to the inhibition of enzymatic activity of the ALOX5 protein.

A 5-LO inhibitor is identified by in vitro and in vivo assays including assessment of the effects of a putative 5-LO inhibitor on ALOX5 mRNA levels, ALOX5 protein levels and/or ALOX5 activity. Assays used in identification of a 5-LO inhibitor illustratively include RT-PCR, Northern blot, immunoblot, immunoprecipitation, ELISA, assay of binding of a putative 5-LO inhibitor to target sequences, assay of 5-LO metabolites, particularly LTB4, and assays for leukemia cells, particularly leukemic stem cells, such as by FACS analysis. Additional assays which identify 5-LO inhibitors are described herein and in Bell R L et al., Ann NY Acad. Sci., 1993, 696:205-15.

To detect lipoxygenase inhibitor activity commercial kits can be also used, e.g. by Cayman Chemicals (Lipoxygenase Inhibitor Screening Assay Kit). The assay is based on measurement of hydroperoxides generated by 5-LO when incubated with arachidonic acid. For example, cells are lysed with a lysis buffer and the lipoxygenase activity is measured in control and treated cells in triplicate. Cell lysates are incubated with a substrate, e.g. linoleic acid. A chromogen is added for detection to measure the absorbance intensities at the appropriate wavelength, e.g. 500 nm for the chromogen provided by Cayman. A further method for identifying 5-LO inhibitors is disclosed in WO 2008/014198.

5-LO Inhibitors-Inhibitory Compounds

Compounds having 5-LO inhibitory activity are included in compositions and methods according to embodiments of the present invention.

5-LO inhibitors include, but are not limited to, zileuton, atreleuton, BW-B 70C, darbufelone, licofelone, minocycline, tepoxalin, tebufelone, curcumin, DHDMBF, BF389, RJW63556, PGV20229, CI986, S2474, ZD2138, CJ-13,610, L-739,010, Wy-50295, TMK688, PEP03, GSK-2190915 and AZD-4407.

5-LO inhibitors include zileuton, also known as 1-[1-(1-benzothiophen-2-yl)ethyl]-1-hydroxyurea. 5-LO inhibitors include, without limitation, N-hydroxyurea derivatives, illustratively including 1-[(2R)-4-[5-[(4-fluorophenyl)methyl]thiophen-2-yl]but-3-yn-2-yl]-1-hydroxyurea, also known as ABT-761, atreleuton and VIA-2291; and 1-[(E)-4-[3-(4-fluorophenoxy)phenyl]but-3-en-2-yl]-1-hydroxyurea, also known as BW-B 70C.

Additional 5-LO inhibitors are disclosed in U.S. Pat. Nos. 4,873,259; 5,234,950; 5,098,932; 5,354,865; 5,220,059, 5,288,751, 5,883,106 and 7,674,811 as well as in publications WO92/01682; WO 92/09567 WO09/069,044; WO03/082312; WO92/109566; and US2007000685892; de Gaetano, G. et al., (2003), Trends in Pharmacological Sciences 24, 245-252; Ruiz, J. et al., (2003), Bioorganic & Medicinal Chemistry 11, 4207-4216; Stewart A O et al., J Med Chem. 1997 Jun. 20; 40(13):1955-68; Bhatia P A et al., J Med Chem. 1996 Sep. 27; 39(20):3938-50; Bell R L et al., J Pharmacol Exp Ther. 1995 February; 272(2):724-31; Carter G W et al., Ann NY Acad Sci. 1994 Nov. 15; 744:262-73; Bell R L et al., Ann NY Acad Sci. 1993 Nov. 30; 696:205-15; Bell R L et al., J Lipid Mediat. 1993 March-April; 6(1-3):259-64; Bell R L et al., Agents Actions, 1993 March; 38(3-4):178-87; and Abraham W M et al., Eur J Pharmacol. 1992 Jul. 7; 217(2-3):119-26.

The tetracycline minocycline (E,4S,4aR,5aS,12aR)-2-(amino-hydroxy-methylidene)-4,7-bis(dimethylamino)-10, 11,12a-trihydroxy-4a,5,5a,6-tetrahydro-4H-tetracene-1,3, 12-trione) has 5-LO inhibitory activity in addition to its bacteriostatic activity.

Curcumin, also known as 1,7-Bis(4-hydroxy-3-methoxyphenyl)-1,6-heptadiene-3,5-dione (Merck Index: 14, 2673), acts as a 5-LO inhibitor, and also has other activities, such as the inhibition of the induction of nitric oxide synthetase and EGF receptor intrinsic kinase activity.

Darbufelone is a 5-LO inhibitor also known as CI1004, (Z)-5-{[3,5-bis(1,1-dimethylethyl)-4-hydroxyphenyl]methylene}-2-imino-4-thiazolidinone methanesulfonate and by the IUPAC name: (5Z)-2-amino-5-[(3,5-ditert-butyl-4-hydroxyphenyl)methylidene]-1,3-thiazol-4-one; methanesulfonic acid.

Licofelone is a 5-LO inhibitor also known as ML3000, 2-[6-(4-chlorophenyl)-2,2-dimethyl-7-phenyl-2,3-dihydro-1H-pyrrolizine-5-yl]acetic acid and by the IUPAC name: 2-[2-(4-chlorophenyl)-6,6-dimethyl-1-phenyl-5,7-dihydropyrrolizin-3-yl]acetic acid.

AZD-4407 is a 5-LO inhibitor also known as [5-<<4-<<2S,4R)-15 tetrahydro-4-hydroxy-2-methyl-2H-pyran-4-yl)thiophen-2-yl)sulfanyl)-1-methylindolin-2-one described in EP 623614 and Alcaraz, M-L et al., Org. Process Res. Dev., 2005, 9 (5), pp 555-569.

Tepoxalin is a 5-LO inhibitor also known as 5-(5-chlorophenyl-N-hydroxy-1-(4-methoxyphenyl)-N-methyl-1H-pyrazole-3-propanamide) and by the IUPAC name: 3-[5-(4-chlorophenyl)-1-(4-methoxyphenyl)pyrazol-3-yl]-N-hydroxy-N-methylpropanamide.

Tebufelone is a 5-LO inhibitor also known as 1-[3,5-bis-(1,1-dimethylethyl)-4-hydroxyphenyl]-5-hexyn-1-one and by the IUPAC name: 1-(3,5-ditert-butyl-4-hydroxyphenyl) hex-5-yn-1-one.

DHDMBF is a 5-LO inhibitor also known as di-7-tert-butyl-2,3-dihydro-3,3-dimethylbenzofuran.

BF389 is a 5-LO inhibitor also known as dihydro-4-(3,5-di-tert-butyl-4-hydroxybenzylidene)-2-methyl-2H-1,2-oxazin-3(4H)-one and dihydro-4-[[3,5-bis(1,1-dimethyl)-4-hydroxyphenyl]methylene]-2-methyl-2H-1,2-oxazin-3(4H)-one.

RJW63556 is a 5-LO inhibitor also known as N-[5-(4-fluoro) phenoxy]thiophene-2-methanesulfonamide.

PGV20229 is a 5-LO inhibitor also known as 1-(7-tert.-butyl-2,3-dihydro-3,3-dimethylbenzo[b]furan-5-yl)-4-cyclopropylbutan-1-one.

CI986 is a 5-LO inhibitor also known as 5-[3,5-bis(1,1-dimethyethyl)-4-hydroxyphenyl]-1,3,4-thiadiazole-2(3H)-thione-2-hydroxy-N,N,N-trimethyl-ethanaminium salt and (5-[3,5-bis(1,1-dimethylethyl)-4-hydroxyphenyl]-1,3,4-thiadizole-2(3H)-thione, choline salt).

S2474 is a 5-LO inhibitor also known as ((E)-(5)-(3,5-di-tert-butyl-4-hydroxybenzylidene)-2-ethyl-1,2-isothiazolidine-1,1-dioxide).

ZD2138 is a 5-LO inhibitor which is a 4-methoxytetrahydropyran derivative. ZD2138 is also known as [6-[3-fluoro-5-[4-methoxy-3,4,5,6-tetrahydro-2H-pyran-4-yl])phenoxymethyl]-1-methyl-2-quinolone] as described in Smith, W. G. et al., J. Pharmacol. Exp. Ther., 275, 1332-1338, 1995.

CJ-13,610 is a 5-LO inhibitor also known as 4-{3-[4-(2-methyl-1H-imidazol-1-yl)phenylthio]}phenyl-3,4,5,6-tetrahydro-2H-pyran-4-carboxamide and described in Mano et al Chem. Pharm. Bull, 53, 965-973, 2005.

L-739,010 is a 5-LO inhibitor also known as 2-cyano-4-(3-furyl)-7-[[6-[3-(3-hydroxy-6,8-dioxabicyclo[3.2.1]octa-nyl)]-2-pyridyl]methoxy]naphthalene and described in Hamel et al J. Med. Chem., 40, 2866-2875, 1997.

Wy-50295 is a 5-LO inhibitor also known as tromethamine, S-[+]-a-methyl-6-12-quinolinyl-methoxy)-2-naphthalene acetic acid-2-hydroxy-1,1-bis(hydroxymethyl) ethylamine salt and by the IUPAC name: (2S)-2-[6-(quinolin-2-ylmethoxy)naphthalen-2-yl]propanoic acid as described in Musser and Kreft, Drugs of the Future, 15, 73-80, 1990.

TMK688 is a 5-LO inhibitor also known as (1-[[5'-(3"-methoxy-4"-ethoxycarbonyloxyphenyl)-2',4'-pentadienoyl] aminoethyl]-4-diphenylmethoxypiperidine, CAS 110501-66-1) and by the IUPAC name: [4-[(1E,3E)-5-[2-(4-benzhydryloxypiperidin-1-yl)ethylamino]-5-oxopenta-1,3-dienyl]-2-methoxyphenyl]ethyl carbonate as described in Tohda et al, Clin. Exp. Allergy, 27, 110-118, 1997.

5-LO Inhibitors-Nucleic Acids

In certain embodiments, compositions and methods for treatment of a myeloproliferative disorder in a subject include antisense treatment.

As used herein, antisense treatment refers to administration or in situ generation of oligonucleotide probes or their derivatives which specifically hybridize or otherwise bind under cellular conditions with the cellular mRNA and/or genomic DNA encoding ALOX5 so as to inhibit expression of ALOX5, e.g. by inhibiting transcription and/or translation. The binding may be by conventional base pair complementarity, or, for example, in the case of binding to DNA duplexes, through specific interactions in the major groove of the double helix. In general, antisense treatment refers to the range of techniques generally employed in the art, and includes any treatment which relies on specific binding to oligonucleotide sequences.

Methods and compositions are provided herein which include one or more nucleic acid inhibitors of ALOX5. Illustrative examples of nucleic acid-based agents include antisense molecules such as antisense oligonucleotides and polynucleotides; catalytic nucleic acid-based agents, such as ribozymes; and nucleic acid-based aptamers. Nucleic acid inhibitors of ALOX5 further illustratively include, RNAi, siRNA, and shRNA inhibitors.

General approaches to constructing oligomers useful in antisense therapy are described, for example, by van der Krol et al., (1988) *Biotechniques* 6:958-976; and Stein et al., (1988) *Cancer Res* 48:2659-2668.

The term "nucleic acid" as used herein refers to RNA or DNA molecules having more than one nucleotide in any form including single-stranded, double-stranded, oligonucleotide or polynucleotide. The term "nucleotide sequence" is used to refer to the ordering of nucleotides in an oligonucleotide or polynucleotide in a single-stranded form of nucleic acid.

The terms "duplex" and "double-stranded" are used to refer to nucleic acids characterized by binding interaction of complementary nucleotide sequences. A duplex includes a "sense" strand and an "antisense" strand. Such duplexes include RNA/RNA, DNA/DNA or RNA/DNA types of duplexes. A duplex may be formed from two nucleotide sequences which are otherwise unconnected. Alternatively, a duplex may be formed by a single-stranded nucleic acid where the single-stranded nucleic acid has substantially complementary sense and antisense regions. Such a nucleic acid forms a "hairpin" conformation when the substantially complementary sense and antisense regions are hybridized to form a duplex.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'. It will be recognized by one of skill in the art that two complementary nucleotide sequences include a sense strand and an antisense strand.

The degree of complementarity, also called homology, between nucleic acid strands significantly affects binding of the strands to each other. An antisense strand which is substantially complementary to a sense strand hybridizes to the sense strand under high stringency hybridization conditions.

The term "hybridization" refers to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The term "specific hybridization" refers to hybridization of a particular nucleic acid to a target nucleic acid without substantial hybridization to nucleic acids other than the target nucleic acid in a cell, tissue or subject.

The term "oligonucleotide" is used herein to describe a nucleotide sequence having from 2-100 linked nucleotides, while the term "polynucleotide" is used to describe a nucleotide sequence having more than 100 nucleotides.

The term "nucleotide" is also used herein as a noun to refer to individual nucleotides or varieties of nucleotides as opposed to a nucleotide sequence.

The term "ribozyme" refers to enzymatic RNA molecules capable of catalyzing the specific cleavage of RNA. The mechanism of ribozyme action involves sequence specific hybridization of the ribozyme molecule to complementary target RNA, followed by an endonucleolytic cleavage. A ribozyme composition includes one or more sequences complementary to ALOX5 mRNA and inhibits the expression of ALOX5.

A 5-LO inhibitor which is a nucleic acid can be produced by chemical synthesis and/or using molecular biology techniques well-known in the art. For example, chemical synthesis of oligonucleotides is described in Herdewijn, P. (Ed.), Oligonucleotide Synthesis: Methods and Applications, Methods in Molecular Biology, Humana Press, 2004. Molecular biology methods relating to anti-ALOX5 nucleic acid synthesis are described, for example, in Sambrook, J. and Russell, D. W., Molecular Cloning: A Laboratory Manual, Cold Spring Harbor Laboratory Press, 3rd Ed., 2001; and Engelke, D. R., RNA Interference (RNAi): Nuts and Bolts of RNAi Technology, DNA Press LLC, Eagleville, Pa., 2003.

Naturally occurring or modified nucleotides may be used in constructing an anti-ALOX5 nucleic acid. Modified nucleotides may be used to increase the stability of an anti-ALOX5 nucleic acid, increase resistance to nucleases, or enhance stability of binding to a target, for instance. Examples of modified nucleotides include phosphorothioates, phosphorodithioates boronophosphates, alkyl phosphonates such as methyl phosphonates, and phosphoramidates such as 3'-amino phosphoramidates, see also U.S. Pat. Nos. 5,176,996; 5,264,564; and 5,256,775.

Generally, antisense nucleic acids useful for inhibiting ALOX5 expression are in the range of about 12 to about 100 nucleotides in length, or longer.

In one embodiment, a 5-LO inhibitor is a double-stranded RNA molecule that inhibits expression of an ALOX5 gene by RNA interference.

RNA interference is a target sequence-specific method of inhibiting a selected gene. RNA interference has been characterized in numerous organisms and is known to be mediated by a double-stranded RNA, also termed herein a double-stranded RNA compound. Briefly described, RNA interference involves a mechanism triggered by the presence of small interfering RNA, siRNA, resulting in degradation of a target complementary mRNA. siRNA is double-stranded RNA which includes a nucleic acid sequence complementary to a target sequence in the gene to be silenced. The double-stranded RNA may be provided as a long double-stranded RNA compound, in which case it is subject to cleavage by the endogenous endonuclease Dicer in a cell. Cleavage by Dicer results in siRNA duplexes having about 21-23 complementary nucleotides in each of the sense strand and the antisense strand, and optionally 1-2 nucleotide 3' overhangs on each of the two strands.

Alternatively, siRNA is provided as a duplex nucleic acid having a sense strand and an antisense strand, wherein the sense and antisense strands are substantially complementary and each of the sense and antisense strands have about 16-30 nucleotides. The complementary sense and antisense strands and optionally include 1-2 nucleotide 3' overhangs on one or both of the two strands. In one embodiment, an siRNA is preferred which has sense and antisense strands, wherein each of the two strands has 21-23 nucleotides, wherein 2 nucleotides on the 3' end of each strand are overhanging and the remaining 19-21 nucleotides are 100% complementary. As noted above, further details of siRNA compounds are described in Engelke, D. R., RNA Interference (RNAi): Nuts and Bolts of RNAi Technology, DNA Press LLC, Eagleville, Pa., 2003. Additional description of siRNA length and composition is found in Elbashir, S. M. et al., Genes and Devel., 15:188-200, 2001; and O'Toole, A. S. et al., RNA, 11:512-516, 2005.

siRNA provided as a duplex nucleic acid having a sense strand and an antisense strand may be configured such that the sense strand and antisense strand form a duplex in hybridization conditions but are otherwise unconnected. A double-stranded siRNA compound may be assembled from separate antisense and sense strands. Thus, for example, complementary sense and antisense strands are chemically synthesized and subsequently annealed by hybridization to produce a synthetic double-stranded siRNA compound.

Further, the sense and antisense strands for inclusion in siRNA may be produced from one or more expression cassettes encoding the sense and antisense strands. Where the sense and antisense strands are encoded by a single expression cassette, they may be excised from a produced transcript to produce separated sense and antisense strands and then hybridized to form a duplex siRNA. See, for example, Engelke, D. R., RNA Interference (RNAi): Nuts and Bolts of RNAi Technology, particularly chapters 5 and 6, DNA Press LLC, Eagleville, Pa., 2003 for further details of synthetic and recombinant methods of producing siRNA.

In a further alternative, a double-stranded "short hairpin" RNA compound, termed "shRNA" or "hairpin siRNA" includes an antisense strand and a sense strand connected by a linker. shRNA may be chemically synthesized or formed by transcription of a single-stranded RNA from an expression cassette in a recombinant nucleic acid construct. The shRNA has complementary regions which form a duplex under hybridization conditions, forming a "hairpin" conformation wherein the complementary sense and antisense strands are linked, such as by a nucleotide sequence of about 1-20 nucleotides. In general, each of the complementary sense and antisense strands have about 16-30 nucleotides.

As noted, siRNA and shRNA may be expressed from a DNA template encoding the desired transcript or transcripts. A DNA template encoding the desired transcript or transcripts is inserted in a vector, such as a plasmid or viral vector, and operably linked to a promoter for expression in vitro or in vivo. Plasmids and viral vectors suitable for transcription of a DNA template are known in the art. Particular viral vectors illustratively include those derived from adenovirus, adeno-associated virus and lentivirus.

The terms "expression construct" and "expression cassette" are used herein to refer to a double-stranded recombinant DNA molecule containing a desired nucleic acid coding sequence and containing appropriate regulatory elements necessary or desirable for the transcription of the operably linked coding sequence in vitro or in vivo. The term "regulatory element" as used herein refers to a nucleotide sequence which controls some aspect of the expression of nucleic acid sequences. Exemplary regulatory elements illustratively include an enhancer, an internal ribosome entry site ("IRES"), an origin of replication, a polyadenylation signal, a promoter, a transcription termination sequence, and an upstream regulatory domain, which contribute to the replication, transcription, post-transcriptional processing of a nucleic acid sequence.

A "vector" is a self-replicating nucleic acid molecule that transfers an inserted nucleic acid molecule into and/or between host cells. The term includes vectors that function primarily for insertion of a nucleic acid molecule into a cell, replication of vectors that function primarily for the replication of nucleic acid, and expression vectors that function for transcription and/or translation of the DNA or RNA. Also included are vectors that provide more than one of the above functions. As used herein, "expression vectors" are defined as polynucleotides which, when introduced into an appropriate host cell, can be transcribed and translated into a polypeptide(s). An "expression system" usually connotes a suitable host cell comprised of an expression vector that can function to yield a desired expression product.

The term "operably linked" as used herein refers to connection of two or more nucleic acid molecules, including an oligonucleotide or polynucleotide to be transcribed and a regulatory element such as a promoter or an enhancer element, which allows transcription of the oligonucleotide or polynucleotide to be transcribed.

The term "promoter" as used herein refers to a DNA sequence operably linked to a nucleic acid sequence to be transcribed such as a nucleic acid sequence encoding a desired molecule. A promoter is generally positioned upstream of a nucleic acid sequence to be transcribed and provides a site for specific binding by RNA polymerase and other transcription factors. In specific embodiments, a promoter is generally positioned upstream of the nucleic acid sequence transcribed to produce the desired molecule, and provides a site for specific binding by RNA polymerase and other transcription factors.

The term "recombinant" is used to indicate a nucleic acid construct in which two or more nucleic acids are linked and which are not found linked in nature.

As will be recognized by one of skill in the art, particular siRNAs may be of different size and still be effective to inhibit a target gene. Routine assay may be performed to determine effective size and composition of particular compounds. Without wishing to be bound by theory, it is believed that at least the antisense strand is incorporated into an endonuclease complex which cleaves the target mRNA complementary to the antisense strand of the siRNA.

Administration of long RNA duplexes processed to siRNA, as well as administration of siRNA or shRNA, and/or expression constructs encoding siRNA or shRNA, results in degradation of the target ALOX5 mRNA and inhibition of expression of the protein encoded by the ALOX5 mRNA, thereby inhibiting activity of the encoded ALOX5 protein in the cell.

Further details of RNA interference mechanisms as well as descriptions of target identification, synthetic siRNA and shRNA production, siRNA and shRNA expression construct production, and protocols for purification and delivery of expression constructs and synthetic siRNA and shRNA in vitro and in vivo are described in Engelke, D. R., RNA Interference (RNAi): Nuts and Bolts of RNAi Technology, DNA Press LLC, Eagleville, Pa., 2003.

A nucleic acid 5-LO inhibitor is directed to a specified target sequence of a nucleic acid molecule encoding human ALOX5 in certain embodiments.

The nucleic acid sequence encoding human ALOX5 is shown and referred to herein as SEQ ID No. 1.

```
  1 atgccctcct acacggtcac cgtggccact ggcagccagt ggttcgccgg cactgacgac 61 tacatctacc tcagcctcgt gggctcggcg ggctgcagcg agaagcacct gctggacaag 121 cccttctaca acgacttcga gcgtggcgcg gtggattcat acgacgtgac tgtggacgag 181 gaactgggcg agatccagct ggtcagaatc gagaagcgca agtactggct gaatgacgac 241 tggtacctga agtacatcac gctgaagacg ccccacgggg actacatcga gttccctgc
```

-continued

```
 301 taccgctgga tcaccggcga tgtcgaggtt gtcctgaggg atggacgcgc aaagttggcc
 361 cgagatgacc aaattcacat tctcaagcaa caccgacgta aagaactgga acacggcaa
 421 aaacaatatc gatggatgga gtggaaccct ggcttcccct tgagcatcga tgccaaatgc
 481 cacaaggatt tacccgtga tatccagttt gatagtgaaa aaggagtgga ctttgttctg
 541 aattactcca aagcgatgga gaacctgttc atcaaccgct tcatgcacat gttccagtct
 601 tcttggaatg acttcgccga ctttgagaaa atctttgtca agatcagcaa cactatttct
 661 gagcgggtca tgaatcactg gcaggaagac ctgatgtttg gctaccagtt cctgaatggc
 721 tgcaaccctg tgttgatccg cgcgctgcaca gagctgcccg agaagctccc ggtgaccacg
 781 gagatggtag agtgcagcct ggagcggcag ctcagcttgg agcaggaggt ccagcaaggg
 841 aacattttca tcgtggactt tgagctgctg gatggcatcg atgccaacaa aacagacccc
 901 tgcacactcc agttcctggc cgctcccatc tgcttgctgt ataagaacct ggccaacaag
 961 attgtcccca ttgccatcca gctcaaccaa atcccgggag atgagaaccc tatttcctc
1021 ccttcggatg caaaatacga ctggcttttg gccaaaatct gggtgcgttc cagtgacttc
1081 cacgtccacc agaccatcac ccaccttctg cgaacacatc tggtgtctga ggttttggc
1141 attgcaatgt accgccagct gcctgctgtg cacccattt tcaagctgct ggtggcacac
1201 gtgagattca ccattgcaat caacaccaag gcccgtgagc agctcatctg cgagtgtggc
1261 ctctttgaca aggccaacgc cacagggggc ggtgggcacg tgcagatggt gcagagggcc
1321 atgaaggacc tgacctatgc ctccctgtgc tttcccgagg ccatcaaggc ccggggcatg
1381 gagagcaaag aagacatccc ctactacttc taccgggacg acgggctcct ggtgtgggaa
1441 gccatcagga cgttcacggc cgaggtggta gacatctact acgagggcga ccaggtggtg
1501 gaggaggacc cggagctgca ggacttcgtg aacgatgtct acgtgtacgg catgcggggc
1561 cgcaagtcct caggcttccc caagtcggtc aagagccggg agcagctgtc ggagtacctg
1621 accgtggtga tcttcaccgc ctccgcccag cacgccgcgg tcaacttcgg ccagctgttc
1681 ctgggcatgt acccagaaga gcattttatc gagaagcctg tgaaggaagc catggcccga
1741 ttccgcaaga acctcgaggc cattgtcagc gtgattgctg agcgcaacaa gaagaagcag
1801 ctgccatatt actacttgtc cccagaccgg attccgaaca gtgtggccat ctga
```

<sup>45</sup>

The amino acid sequence of human ALOX5 is shown and referred to herein as SEQ ID No. 2.

A nucleic acid sequence encoding a human ALOX5 protein of SEQ ID No. 2 may be identical to the nucleotide sequence

```
  1 mpsytvtvat gsqwfagtdd yiylslvgsa gcsekhlldk pfyndferga vdsydvtvde
 61 elgeiqlvri ekrkywlndd wylkyitlkt phgdyiefpc yrwitgdvev vlrdgrakla
121 rddqihilkq hrrkeletrq kqyrwmewnp gfplsidakc hkdlprdiqf dsekgvdfvl
181 nyskamenlf inrfmhmfqs swndfadfek ifvkisntis ervmnhwqed lmfgyqflng
241 cnpvlirrct elpeklpvtt emvecslerq lsleqevqqg nifivdfell dgidanktdp
301 ctlqflaapi cllyknlank ivpiaiqlnq ipgdenpifl psdakydwll akiwvrssdf
361 hvhqtithll rthlvsevfg iamyrqlpav hpifkllvah vrftiaintk areqlicecg
421 lfdkanatgg gghvqmvqra mkdltyaslc fpeaikargm eskedipyyf yrddgllvwe
481 airtftaevv diyyegdqvv eedpelqdfv ndvyvygmrg rkssgfpksv ksreqlseyl
541 tvviftasaq haavnfgqlf lgmypeehfi ekpvkeamar frknleaivs viaernkkkq
601 lpyyylspdr ipnsvai
``` shown in SEQ ID NO. 1, or, owing to the degeneracy of the genetic code, a different nucleic acid sequence may encode the same ALOX5 protein of SEQ ID No. 2. Thus, a nucleic acid 5-LO inhibitor is directed to a specified target sequence of the nucleic acid sequence of SEQ ID No. 1 or a target sequence of an alternate nucleic acid sequence encoding the ALOX5 protein of SEQ ID No. 2.

A nucleic acid 5-LO inhibitor may also be directed to a nucleic acid sequence encoding a variant of the protein shown in SEQ ID NO. 2. Variants include naturally occurring allelic variants or non-naturally occurring allelic variants. Such naturally occurring and non-naturally occurring variants include proteins having amino acid deletions, substitutions and additions, as well as fragments, derivatives or analogs of SEQ ID No. 2. The terms "allelic variant," "fragment," "derivative" and "analog" when referring to the protein of SEQ ID No. 2 refer to a protein which retains essentially the same biological function or activity as the protein of SEQ ID No. 2.

An ALOX5 target sequence for a nucleic acid 5-LO inhibitor is identified using several criteria to optimize the ALOX5 inhibiting effects. Target ALOX5 sequences for siRNA and shRNA mediated inhibition are selected which have about a 30-50% GC content. Thus, for example, a 21 nucleotide target sequence optimally includes about 5-11 guanine and/or cytosine residues.

Selected target sequences are compared to other sequences in a nucleic acid database to identify target sequences having significant homology to non-target sequences which may be present in a cell or organism to which the 5-LO inhibitor is delivered. Such databases may include the publicly available GENBANK, described in Benson D. A., et al., GenBank, Nucleic Acids Res., 2006 Jan. 1; 34(Database issue):D16-20, for instance. Any such identified non-specific sequences are eliminated from consideration for use in methods or compositions according to the present invention. Comparison of target sequences to database sequences may be accomplished using any of various comparison methods and tools known in the art. A commonly used tool is the Basic Local Alignment Search Tool (BLAST), first described in Altschul, S. F. et al., Basic local alignment search tool, J. Mol. Biol., 215:403-10, 1990. The BLAST tools are available for use online or download from the National Center for Biotechnology Information (NCBI) at http://www.ncbi.nlm.nih.gov. One of skill in the art can determine appropriate parameters for detecting homology between a potential target for an anti-ALOX5 nucleic acid agent and other nucleic acid sequences without undue experimentation. For example, for each siRNA, the full nucleotide target sequence was tested for homology with any DNA or RNA sequence in all the databases using BLAST.

An identified target sequence may be further validated by producing an anti-ALOX5 nucleic acid compound directed to the target sequence and assaying the efficacy of the compound in inhibiting ALOX5 transcription and/or translation in vitro and/or in vivo.

A nucleic acid 5-LO inhibitor is introduced into a cell by any of various methods well-known in the art. A nucleic acid 5-LO inhibitor may be delivered to cells in vivo using methods such as direct injection of DNA, receptor-mediated DNA uptake, viral-mediated transfection or non-viral transfection and lipid based transfection, all of which may involve the use of vectors. For example, a nucleic acid can be introduced into a cell via calcium phosphate or calcium chloride co-precipitation-mediated transfection, DEAE-dextran-mediated transfection or electroporation.

Direct injection has been used to introduce naked DNA into cells in vivo (Acsadi et al., 1991; Wolff et al., 1990). A delivery apparatus (e.g., a "gene gun") for injecting DNA into cells in vivo may be used. Such an apparatus may be commercially available (Bio-Rad Laboratories, Hercules, Calif.). Naked DNA may also be introduced into cells by complexing the DNA to a cation, such as polylysine, which is coupled to a ligand for a cell-surface receptor (Wu and Wu, 1988; Wilson et al., 1992; U.S. Pat. No. 5,166,320). Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes (Curiel et al., 1991; Cristiano et al., 1993).

Defective retroviruses, are well characterized vectors (Miller, 1990). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include psi.Crip, psi.Cre, psi.2 and psi.Am. Retroviruses have been used to introduce a variety of genes into many different cell types, both in vitro and in vivo, including epithelial cells, endothelial cells, lymphocytes, myoblasts, hepatocytes, and bone marrow cells (Eglitis et al., 1985; Danos and Mulligan, 1988; Wilson et al., 1988; Armentano et al., 1990; Huber et al., 1991; Ferry et al., 1991; Chowdhury et al., 1991; van Beusechem et al., 1992; Kay et al., 1992; Dai et al., 1992; Hwu et al., 1993; U.S. Pat. No. 4,868,116; U.S. Pat. No. 4,980,286; PCT Publication No. WO 89/07136; PCT Publication No. WO 89/02468; PCT Publication No. WO 89/05345; and PCT Publication No. WO 92/07573).

Suitable adenoviral vectors derived from the adenovirus strain Ad type 5 dl324 or other strains of adenovirus (e.g., Ad2, Ad3, Ad7) are well known to those skilled in the art. Recombinant adenoviruses are advantageous in that they do not require dividing cells to be effective gene delivery vehicles and can be used to infect a wide variety of cell types, including airway epithelium (Rosenfeld et al., 1992), endothelial cells (Lemarchand et al., 1992), hepatocytes (Herz and Gerard, 1993) and muscle cells (Quantin et al., 1992).

Adeno-associated virus (AAV) is a well-known vector. AAV is a naturally occurring defective virus that requires another virus, such as an adenovirus or a herpes virus, as a helper virus for efficient replication and a productive life cycle (Muzyczka et al., 1992). AAV may be used to integrate DNA into non-dividing cells (Flotte et al., 1992; Samulski et al., 1989; McLaughlin et al., 1989). An AAV vector such as that described in Tratschin et al., 1985 may be used to introduce DNA into cells (Hermonat et al., 1984; Tratschin et al., 1985; Wondisford et al., 1988; Tratschin et al., 1984; and Flotte et al., 1993). Lentiviral vectors may also be adapted for use in the invention.

General methods for nucleic acid delivery are known in the art (see for example, U.S. Pat. No. 5,399,346). A biocompatible capsule for delivering genetic material is described in PCT Publication No. WO 95/05452. Methods of gene transfer into hematopoietic cells have also previously been reported (Clapp et al., 1991; Anderson, 2000; Cavazzana-Calvo et al., 2000).

Details of these and other techniques are known in the art, for example, as described in J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; and Engelke, D. R., RNA Interference (RNAi): Nuts and Bolts of RNAi Technology, DNA Press LLC, Eagleville, Pa., 2003.

Suitable assays for assessment of the effects of introduction of an effective amount of an anti-ALOX5 nucleic acid compound into a cell are known in the art and illustratively include assays for ALOX5 protein and/or ALOX5 encoding RNA by one or more of: RT-PCR, Northern blot, immunoblot, immunoprecipitation, and ELISA. Additional assays for effective anti-ALOX5 nucleic acid compounds include assay of one or more ALOX5 metabolites, particularly LTB4, such as by immunoblot, immunoprecipitation, or ELISA; and assays for leukemia cells, such as FACS analysis.

5-LO Inhibitors-5-LO Binding Compositions

An antibody or antibody fragment which is a 5-LO inhibitor included in a composition and/or method of the present invention specifically binds to ALOX5 and inhibits activity of ALOX5. Examples of ALOX5 binding inhibitors include antibodies.

The term "antibody" herein is used in its broadest sense and illustratively includes polyclonal antibodies, monoclonal antibodies, chimeric antibodies, humanized antibodies, as well as antigen binding antibody fragments and molecules having ALOX5 binding functionality. The term "antibody" includes an intact immunoglobulin having four polypeptide chains, two heavy (H) chains and two light (L) chains linked by disulfide bonds. The term antibody also includes "antigen binding antibody fragments" illustratively including such fragments as an Fab fragment, an Fab' fragment, an F(ab')2 fragment, an Fd fragment, an Fv fragment, an scFv fragment, and a domain antibody (dAb).

Antibodies are generated using standard techniques, using ALOX5 protein or DNA, or peptides corresponding to portions of ALOX5, as an antigen. Methods of antibody generation are described in detail in E. Harlow and D. Lane, Antibodies: A Laboratory Manual, Cold Spring Harbor Laboratory Press, 1988; and B. K. C. Lo, Antibody Engineering: Methods and Protocols (Methods in Molecular Biology) Humana Press, December 2003.

Non-Immunoglobulin Binding Proteins

In addition to antibodies, many other protein domains mediate specific high-affinity interactions. A wide range of different non-immunoglobulin scaffolds with diverse origins and characteristics are currently used for, for example, combinatorial library display. A wide range of different non-immunoglobulin scaffolds with diverse origins and characteristics are currently used for, for example, combinatorial library display. Exemplary non-immunoglobulin scaffolds may include an antibody substructure or other protein structure, such as an ankyrin-repeat domain. Exemplary non-immunoglobulin based affinity proteins include Affibody molecules, which are based on combinatorial protein engineering of the small and robust a-helical structure of protein A. Affibody molecules have been widely used as selective binding reagents. In addition, Affibody molecules labeled with fluorescence markers allow quantitative measurements of non-labeled target molecules.

In some embodiments, a protein-binding molecule can be, for example, but not limited to, an antibody substructure, minibody, adnectin, anticalin, affibody, affilin, avibodies, avimer, knottin, fynomer, phylomer, SMIP, versabodies, glubody, C-type lectin-like domain protein, designed ankyrin-repeat proteins (DARPin), tetranectin, kunitz domain protein, thioredoxin, cytochrome b562, zinc finger scaffold, Staphylococcal nuclease scaffold, fibronectin or fibronectin dimer, tenascin, N-cadherin, E-cadherin, ICAM, titin, GCSF-receptor, cytokine receptor, glycosidase inhibitor, antibiotic chromoprotein, myelin membrane adhesion molecule P0, CD8, CD4, CD2, class I MHC, T-cell antigen receptor, CD1, C2 and I-set domains of VCAM-1, I-set immunoglobulin domain of myosin-binding protein C, I-set immunoglobulin domain of myosin-binding protein H, I-set immunoglobulin domain of telokin, NCAM, twitchin, neuroglian, growth hormone receptor, erythropoietin receptor, prolactin receptor, interferon-gamma receptor, β-galactosidase/glucuronidase, β-glucuronidase, transglutaminase, ubiquitin, T-cell antigen receptor, superoxide dismutase, tissue factor domain, cytochrome F, green fluorescent protein, GroEL, and thaumatin. The protein-binding molecules can be used in a similar way as antibodies (for example see Zahnd et al. J. Biol. Chem. 2006, Vol. 281, Issue 46, 35167-35175).

Aptamers

Aptamers are an example of 5-LO inhibitors that can be nucleic acid-based 5-LO inhibitors or peptide-based binding compositions that inhibit ALOX5. The term "aptamer" as used herein is intended to mean a nucleic acid and/or peptide that specifically binds to a target. Aptamers are selected from pools of nucleic acids and/or peptides for their selective binding properties. In the case of a nucleic acid aptamer, the aptamer is characterized by binding interaction with a target other than Watson-Crick base pairing or triple helix binding with a second and/or third nucleic acid. Such binding interaction may include Van der Waals interaction, hydrophobic interaction, hydrogen bonding and/or electrostatic interactions, for example. Similarly, peptide-based aptamers are characterized by specific binding to a target wherein the aptamer is not a naturally occurring ligand for the target. In the context of the present invention, a 5-LO inhibitor which is an aptamer is characterized by ALOX5 binding and inhibiting ALOX5 function.

5-LO Inhibitor Modifications

A 5-LO inhibitor is optionally modified to enhance delivery to a target and/or to enhance therapeutic efficacy.

For example, one or more cellular targeting moieties that direct the 5-LO inhibitor into a cell or to a subcellular region can be included. Such cellular targeting moieties include, for example and without limitation: those described in Lindgren, M. et al. "Cell-penetrating peptides." Trends Pharmacol. Sci. vol. 21, No. 3, pp.: 99-103 (2000); a Protein Transduction Domain (PTD) of TAT protein, or a synthetic analog of thereof (M. Becker-Hapak, S. S. McAllister, and S. F. Dowdy (2001) Methods 24: 247-256, A. Ho et al. (2001) Cancer Res. 61: 474-477); *Drosophila* antennapedia protein domain called Helix-3 or Penetratin-1, or a synthetic analog thereof (D. Derossi, G. Chassaing, and A. Prochiantz (1998) Trends Cell Biol. 8: 84-87, A. Prochiantz (1996) Curr. Opin. Neurobiol. 6: 629-63); Herpesvirus VP22 protein transport domain, or a synthetic analog thereof (N. Normand, H. van Leeuwen, and P. O'Hare (2001) J. Biol. Chem. 276: 15042-15050, A. Phelan, G. Elliott, and P. O'Hare (1998) Nat. Biotech. 16: 440-443); Membrane-Translocating Sequence (MTS) from Kaposi fibroblast growth factor or related amino acid sequences such as AAVLLPVLLAAP (M. Rojas, J. P. Donahue, Z. Tan, and Y.-Z. Lin (1998) Nat. Biotech. 16: 370-375, C. Du, S. Yao, M. Rojas, and Y.-Z. Lin (1998) J. Peptide Res. 51: 235-243); Pep-1, MPG, and similar peptides (M. C. Morris et al. (2001) Nat. Biotech. 19: 1173-1176, M. C. Morris et al. (1999) Nuc. Ac. Res. 27: 3510-3517); and Transportan, Transportan 2, and similar peptides or a synthetic analog thereof (M. Pooga et al. (1998) FASEB J. 12: 67-77; and M. Pooga et al. (1998) Ann. New York Acad. Sci. 863: 450 453).

Further, a 5-LO inhibitor is optionally conjugated to a therapeutic moiety such as a cytotoxin, a therapeutic agent or a radioactive metal ion. A cytotoxin or cytotoxic agent includes any agent that is detrimental to cells. Exemplary cytotoxins and cytotoxic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Techniques for conjugating a targeting moiety and/or therapeutic moiety to an antibody or non-immunologlobulin binding moiety are well known, for example, as described in Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84; Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982). Carbodiimide conjugation, such as detailed in Bauminger, S. and Wilchek, M., (1980) Methods Enzymol. 70, 151-159, may be used to conjugate a variety of therapeutic and/or targeting moieties to antibodies or non-immunoglobulin binding moieties.

Combination Treatments

Combinations of therapeutic agents are administered according to embodiments of the present invention. In some embodiments, two or more 5-LO inhibitors are administered to a subject to treat a myeloproliferative disorder in the subject. In further embodiments, at least one 5-LO inhibitor and at least one additional therapeutic agent are administered to a subject to treat a myeloproliferative disorder. In still further embodiments, at least one 5-LO inhibitor and at least two additional therapeutic agents are administered to a subject to treat a myeloproliferative disorder.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject.

The at least one additional therapeutic agent is an anti-cancer agent according to embodiments of the present invention including, without limitation, a kinase inhibitor, a 5-lipoxygenase-activating protein inhibitor, an Hsp90 inhibitor, an anti-metabolite, an alkylating agent, a steroid, interferon alpha 2b; or a combination of any two or more thereof. As will be recognized by one of skill in the art, identification of a therapeutic agent as kinase inhibitor, a 5-lipoxygenase-activating protein inhibitor, an Hsp90 inhibitor, an anti-metabolite, or an alkylating agent does not limit the identified agent to only one type of therapeutic activity. Thus, for example, a kinase inhibitor may be characterized as a dual inhibitor, having specific activity to inhibit two types of kinases, or a multi-kinase inhibitor, having specific activity to inhibit three or more types of kinases. Illustratively, a dual kinase inhibitor can have activity as a tyrosine kinase inhibitor and as a src kinase inhibitor.

In yet further embodiments, at least one 5-LO inhibitor is administered to a subject to treat a myeloproliferative disorder along with an additional anti-cancer treatment such as radiation therapy and/or chemotherapy and/or bone marrow or cord blood transplant.

Combination therapies utilizing one or more 5-LO inhibitors and one or more kinase inhibitors, one or more 5-lipoxygenase-activating protein inhibitors and/or one or more Hsp90 inhibitors may show synergistic effects, e.g., a greater therapeutic effect than would be observed using either inhibitor as a monotherapy.

In various embodiments, combination therapies including a 5-LO inhibitor may refer to (1) pharmaceutical compositions that include one or more 5-LO inhibitors in combination with one or more additional therapeutic agents; and (2) co-administration of one or more 5-LO inhibitors with one or more additional therapeutic agents wherein the 5-LO inhibitor and the one or more additional therapeutic agents have not been formulated in the same composition. When using separate formulations, the 5-LO inhibitor may be administered at the same time, intermittent times, staggered times, prior to, subsequent to, or combinations thereof, with reference to the administration of the one or more additional therapeutic agents.

Further embodiments of methods of combination therapies according to the present invention include administration of a 5-LO inhibitor and at least two of: a kinase inhibitor, a FLAP inhibitor and an Hsp90 inhibitor.

Combination therapies including 5-LO inhibitors and an additional therapeutic agent, such as a kinase inhibitor, FLAP inhibitor and/or Hsp90 inhibitor, may be advantageous over combination therapies known in the art because the combination allows the additional therapeutic agent to exert greater effect at lower dosage.

Combination treatments can allow for reduced effective dosage and increased therapeutic index of therapeutic agents used in methods of the present invention. Thus, for example, the effective dose ($ED_{50}$) for a BCR-ABL kinase inhibitor, such as imatinib, when used in combination with a 5-LO kinase inhibitor can be at least 2 fold less than the $ED_{50}$ for the BCR-ABL kinase inhibitor alone, and even more preferably at 5 fold, 10 fold or even 25 fold less. Conversely, the therapeutic index (TI) for such BCR-ABL kinase inhibitor when used in combination with a 5-LO kinase inhibitor described herein can be at least 2 fold greater than the TI for a BCR-ABL kinase inhibitor regimen alone, and even more preferably at 5 fold, 10 fold or even 25 fold greater. The use of the combination therapy will give a greater chance to target the leukemic stem cells effectively.

Combination Treatment with One or More 5-LO Inhibitors and One or More Kinase Inhibitors Combination therapies utilizing one or more 5-LO inhibitors and one or more kinase inhibitors may show synergistic effects, e.g., a greater therapeutic effect than would be observed using either inhibitor as a monotherapy.

In certain embodiments, combinations therapies include one or more 5-LO inhibitors and at least one kinase inhibitor selected from tyrosine kinase inhibitors, Src kinase inhibitors, BCR-ABL kinase inhibitors, dual specificity kinase inhibitors, multi-specificity kinase inhibitors and aurora kinase inhibitors. Combinations of two or more kinase inhibitors are included according to embodiments of the present invention.

In various embodiments, combination therapies including a 5-LO inhibitor may refer to (1) pharmaceutical compositions that include one or more 5-LO inhibitors in combination with one or more kinase inhibitors; and (2) co-administration of one or more 5-LO inhibitors with one or more kinase inhibitors wherein the 5-LO inhibitor and the kinase inhibitor have not been formulated in the same composition. When using separate formulations, the 5-LO inhibitor may be administered at the same time, intermittent times, staggered times, prior to, subsequent to, or combinations thereof, with reference to the administration of the kinase inhibitor.

Tyrosine Kinase Inhibitors

One or more tyrosine kinase inhibitors is included in embodiments of methods and compositions of the present invention.

In preferred embodiments, an included tyrosine kinase inhibitor inhibits bcr-abl kinase and may also have activity to inhibit one or more additional tyrosine kinases.

The term "bcr-abl" refers to an oncoprotein encoded by a chimeric oncogene generated by the translocation of sequences from the cABL protein tyrosine kinase on chromosome 9 into BCR sequences on chromosome 22. In this application the terms BCR-ABL, Bcr-Abl and bcr-abl are used interchangeably and refer to the fused gene resulting from genetic translocation of BCR and ABL, RNA and fusion protein, also known as Bcr-Abl tyrosine kinase. This fusion protein has been found in three major forms: P190, P210 and P230.

The term "BCR-ABL inhibitor" refers to an agent that decreases the level of a BCR-ABL kinase protein and/or decreases at least one activity of a BCR-ABL kinase.

Exemplary activities of BCR-ABL kinases include, for example, protein tyrosine kinase activity and interaction with other proteins (e.g., an SH2 or SH3 interaction inhibitor). Agents that may be inhibitors of BCR-ABL kinases, include, for example, a polypeptide, nucleic acid, macromolecule, or small molecule. BCR-ABL kinase inhibitors may act to inhibit a BCR-ABL kinase either directly or indirectly. In one embodiment, a BCR-ABL kinase inhibitor may prevent activation of a BCR-ABL kinase, for example, by inhibiting a protein that directly or indirectly acts to stimulate BCR-ABL kinase activity.

Compounds having BCR-ABL inhibitory activity are included in compositions and methods according to embodiments of the present invention.

Kinase inhibitors included in compositions and methods according to embodiments of the present invention include, but are not limited to, imatinib, dasatinib, nilotinib, bosutinib, AZD0530, NPB-001-05, AT9283, BAY 43-9006, bafetinib, 3-(imidazo[1,2-b]pyridazin-3-ylethynyl)-4-methyl-N-{4-[(4-methylpiperazin-1-yl)methyl]-3-(trifluoromethyl)phenyl}benzamide (also known as AP24534), lestaurtinib, tozasertib, danusertib, XL228, KW-2449, AT-9283, VE-465, DCC-2036, PKC412, SGX393 and vatalanib.

BCR-ABL tyrosine kinase inhibitors include, but are not limited to, 4-[(4-methylpiperazin-1-yl)methyl]-N-[4-methyl-3-[(4-pyridin-3-ylpyrimidin-2-yl)amino]phenyl]benzamide, also known as imatinib (Gleevec, Novartis); N-(2-chloro-6-methylphenyl)-2-[[6-[4-(2-hydroxyethyl)-1-piperazinyl]-2-methyl-4-pyrimidinyl]amino]-5-thiazolecarboxamide monohydrate, also known as dasatinib (Sprycel, BMS-354825, Bristol-Myers Squibb; dual inhibitor for BCR-ABL and src family kinases); 4-methyl-N-[3-(4-methyl-1H-imidazol-1-yl)-5-(trifluoromethyl)phenyl]-3-[(4-pyridin-3-ylpyrimidin-2-yl)amino]benzamide, also known as nilotinib (Novartis), AMN107 and by the IUPAC name: 4-methyl-N-[3-(4-methylimidazol-1-yl)-5-(trifluoromethyl)phenyl]-3-[(4-pyridin-3-ylpyrimidin-2-yl)amino]benzamide; and 4-[(2,4-dichloro-5-methoxyphenyl)amino]-6-methoxy-7-[3-(4-methylpiperazin-1-yl)propoxy]quinoline-3-carbonitrile, also known as bosutinib (Wyeth, SKI-606), a 4-anilino-3-quinolinecarbonitrile dual inhibitor of Src and Abl kinases.

AZD0530 (Saracatinib) is a dual tyrosine kinase inhibitor also known as N-(5-chloro-1,3-benzodioxol-4-yl)-7-(2-(4-methylpiperazin-1-yl)ethoxy)-5-(tetrahydro-2H-pyran-4-yloxy)quinazolin-4-amine and by the IUPAC name: N-(5-chloro-1,3-benzodioxol-4-yl)-7-[2-(4-methylpiperazin-1-yl)ethoxy]-5-(oxan-4-yloxy)quinazolin-4-amine.

Bafetinib is an ABL kinase inhibitor also known as INNO-406, NS-187 and by the IUPAC name: 4-[[(3S)-3-(dimethylamino)pyrrolidin-1-yl]methyl]-N-[4-methyl-3-[(4-pyrimidin-5-ylpyrimidin-2-yl)amino]phenyl]-3-(trifluoromethyl)benzamide.

Lestaurtinib is a JAK2, FLT3 and TrkA kinase inhibitor also known as CEP-701 and (9S,10S,12R)-2,3,9,10,11,12-Hexahydro-10-hydroxy-10-(hydroxymethyl)-9-methyl-9,12-epoxy-1H-diindolo[1,2,3-fg:3',2',1'-kl]pyrrolo[3,4-i][1,6]benzodiazocin-1-one.

PKC412 is a kinase inhibitor also known as midostaurin, and [9S-(9a,10b,11b,13a)]-N-(2,3,10,11,12,13-Hexahydro-10-methoxy-9-methyl-1-oxo-9,13-epoxy-1H,9H-diindolo[1,2,3-gh:3',2',1'-1m]pyrrolo[3,4-j][1,7]benzodiazonin-11-yl)-N-methylbenzamide.

Vatalanib is a multi-tyrosine kinase inhibitor also known as PTK787/ZK-222584 and N-(4-chlorophenyl)-4-(pyridin-4-ylmethyl)phthalazin-1-amine.

Src Kinase Inhibitors

The term "Src kinase" refers to a member of the Src tyrosine kinase family. Exemplary Src kinases include, for example, Src, c-Src, v-Src, Yes, c-Yes, v-Yes, Fyn, Lyn, Lck, Blk, Hck, Fgr, c-Fgr, v-Fgr, lck (or p56lck), Tkl, Csk, Ctk and homologs (e.g., orthologs and paralogs), variants, or fragments thereof.

The term "Src kinase inhibitor" refers to an agent that decreases the level of a Src kinase protein and/or decreases at least one activity of a Src kinase. Exemplary activities of Src kinases include, for example, protein tyrosine kinase activity and interaction with other proteins (e.g., an SH2 interaction inhibitor). Src kinase inhibitors may act to inhibit a Src kinase either directly or indirectly. In one embodiment, a Src kinase inhibitor may prevent activation of a Src kinase, for example, by inhibiting a protein that directly or indirectly acts to stimulate Src kinase activity.

Src kinase inhibitors included in embodiments of methods and compositions of the present invention include, but are not limited to, N-(5-chloro-1,3-benzodioxol-4-yl)-7-(2-(4-methylpiperazin-1-yl)ethoxy)-5-(tetrahydro-2H-pyran-4-yloxy)quinazolin-4-amine, also known as AZD0530 AZD0530 is a dual-specific inhibitor of Src and Abl, protein tyrosine kinases that are overexpressed in chronic myeloid leukemia cells.

Aurora Kinase Inhibitors

The term "aurora kinase" refers a member of the serine/threonine kinase family. Members of this family are aurora A (also known as aurora 2 or serine/threonine-protein kinase 6 or AURKA), aurora B and aurora C. Exemplary activities of aurora kinases include, for example, cell proliferation, mitotic regulation, and cell division. Aurora kinase inhibitors may act to inhibit a aurora kinase either directly or indirectly. In one embodiment, a aurora kinase inhibitor may prevent activation of a aurora kinase, for example, by inhibiting a protein that directly or indirectly acts to stimulate aurora kinase activity. In another embodiment, the interaction of aurora-B with its binding partner surviving may be blocked by an inhibitor, alternatively the ATP binding site of the aurora kinase may be blocked.

Aurora kinase inhibitors included in embodiments of methods and compositions of the present invention include, but are not limited to N-[4-[[6-Methoxy-7-[3-(4-morpholinyl)propoxy]-4-quinazolinyl]amino]phenyl]benzamide (also known as ZM447439), Hesperadin (Hauf et al., J. Cell Biol. 2003, 161, 281-294); MLN8237; KW-2449 (Shiotsu et al. 2007, Blood 110, p. 1832); XL228; VE-465; 1-Cyclopropyl-3-(3-(6-(morpholinomethyl)-1H-benzo[d]imidazol-2-yl)-1H-pyrazol-4-yl)urea (also known as AT9283); N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide (also known as PF-03814735) and DCC-2036.

Tozasertib is a aurora kinase inhibitor also known as MK-0457 and VX-680 and by the IUPAC name: N-[4-[4-(4-methylpiperazin-1-yl)-6-[(5-methyl-1H-pyrazol-3-yl)amino]pyrimidin-2-yl]sulfanylphenyl]cyclopropanecarboxamide.

Danusertib is a aurora kinase inhibitor also known as PHA-739358 and by the IUPAC name: N-[5-[(2R)-2-methoxy-2-phenylacetyl]-4,6-dihydro-1H-pyrrolo[3,4-c]pyrazol-3-yl]-4-(4-methylpiperazin-1-yl)benzamide.

Specific aurora kinase inhibitors as well as pan-aurora kinase inhibitors may be useful for treatment of CML or MPD.

Other Kinase Inhibitors

Other kinase inhibitors have shown to be useful for the treatment of CML or MPD. Kinase inhibitors included in embodiments of methods and compositions of the present invention include, but are not limited to sorafenib tosylate (also known as BAY 43-9006 or Nexavar)

In an exemplary embodiment, a combination therapy including administering to a subject zileuton and imatinib mesylate.

Imatinib mesylate is a protein tyrosine kinase inhibitor that inhibits the BCR-ABL tyrosine kinase created by the Philadelphia chromosome abnormality in CML. Imatinib mesylate achieves this inhibitory result through binding to the adenosine triphosphate-binding site of the BCR-ABL tyrosine kinase, which prevents phosphorylation of substrates and related malignant transformation. Through inhibition of this kinase, it is believed that imatinib mesylate inhibits cell proliferation and induces apoptosis (T. Schindler et al (2000) Science 289:1938-1942).

Imatinib mesylate is indicated for treatment of CML patients in blast phase, accelerated phase, or in chronic phase after failure of interferon-alpha therapy. Present dosages recommended for treatment with imatinib mesylate are 200-400 mg/day for patients with chronic phase CML and 500-800 mg/day for patients with accelerated phase or blast phase CML. In the event of disease progression, failure to achieve a satisfactory hematologic response after at least 3 months of treatment; or loss of a previously achieved hematologic response, the dose of imatinib mesylate may be increased. Treatment dosage may be increased in patients with chronic phase CML from 400 mg/day to 600 mg/day in the absence of severe adverse drug reaction and severe non-leukemia related neutropenia or thrombocytopenia. Similarly, treatment dosage may be increased in patients with chronic phase CML from 600 mg/day to 800 mg/day (Novartis, Gleevec package insert T-2001-14 90012401).

As will be recognized by one of skill in the art, alternative forms, such as alternative salts, hydrates or solvates other than the mesylate salt of imatintib, may be pharmaceutically acceptable and may be used according to embodiments of the present invention.

In an exemplary embodiment, a combination therapy including administering to a subject zileuton and dasatinib.

Dasatinib is indicated for treatment of CML patients in accelerated (advanced) phase, lymphoid blast phase or chronic phase. Present dosages recommended for treatment with dasatinib are 100 mg/day for patients with chronic phase, CML and 140 mg/day for patients with accelerated phase or blast phase CML with resistance or intolerance to imatinib or interferon-alpha therapy. In the event of disease progression, failure to achieve a satisfactory hematologic response; or loss of a previously achieved hematologic response, the dose of dasatinib may be increased. Treatment dosage may be increased in patients with chronic phase CML from 100 mg/day to 140 mg/d and for patients with accelerated phase or blast phase CML from 140 mg/day to 180 mg/d in the absence of severe adverse drug reaction and severe non-leukemia related neutropenia or thrombocytopenia (Bristol-Myers Squibb Company, SPRYCEL, package insert DS-B0001-0609).

In an exemplary embodiment, a combination therapy including administering to a subject zileuton and nilotinib.

Nilotinib is indicated for treatment of CML patients in accelerated (advanced) phase, lymphoid blast phase or chronic phase resistant or intolerant to prior therapy including imatinib. Present dosages recommended for treatment with nilotinib are 400 mg twice daily (taken as two 200 mg capsules every twelve hours). In the event of toxicities (hematological or liver), the dose may be reduced to 400 mg/day (Novartis, Tasigna, package insert T2009-95/T2009-96).

Combination Treatment with One or More 5-LO Inhibitors and One or More Hsp90 Inhibitors Combination therapies utilizing one or more 5-LO inhibitors and one or more Hsp90 inhibitors may show synergistic effects, e.g., a greater therapeutic effect than would be observed using either inhibitor as a monotherapy.

In an exemplary embodiment, a combination therapy including administering to a subject zileuton and retaspimycin hydrochloride (IPI-504) or 17-amino-17-demethoxygeldanamycin (IPI-493).

In various embodiments, combination therapies including a 5-LO inhibitor may refer to (1) pharmaceutical compositions that include one or more 5-LO inhibitors in combination with one or more Hsp90 inhibitors; and (2) co-administration of one or more 5-LO inhibitor with one or more Hsp90 inhibitors wherein the 5-LO inhibitor and the Hsp90 inhibitor have not been formulated in the same compositions. When using separate formulations, the 5-LO inhibitor may be administered at the same time, intermittent times, staggered times, prior to, subsequent to, or combinations thereof, with reference to the administration of the Hsp90 inhibitor.

In certain embodiments, combinations therapies may include one or more 5-LO inhibitor, one or more Hsp90 inhibitors and/or or BCR-ABL kinase inhibitors, and/or one or more dual specificity inhibitors, and various combinations thereof.

Hsp90 Inhibitors

The term "Hsp90 inhibitor" refers to an agent that decreases the level of Hsp90 protein and/or decreases at least one activity of Hsp90 protein. Exemplary activities of Hsp90 include, for example, prevention of protein aggregation, prevention of misfolding, assisting in the proper folding of proteins and stabilization of proteins including mutant proteins, such as v-src and bcr-abl.

Compounds having Hsp90 inhibitory activity are included in compositions and methods according to embodiments of the present invention.

Hsp90 inhibitors included in compositions and methods according to embodiments of the present invention include, but are not limited to, geldanamycin, tanespimycin, retaspimycin, alvespimycin, macbecin, gamitrinibs, BIIB028, BIIB-021, SNX-0723, SNX-2112, SNX-5422 mesylate, SNX-7081, AT13387, Resorcinol 7, pochonin D, Pochoxime A, Pochoxime B, Pochoxime C, STA-1474, STA-9090, Radicicol, KW-2478, MPC-3100, HSP990, XL888, NVP-HSP990, PU-H71, PU24FC1, PU-DZ8, Purine 6 and AV-142

Hsp90 inhibitors included in compositions and methods according to embodiments of the present invention include, but are not limited to, ansamycin Hsp90 inhibitors, ansamycin-derived Hsp90 inhibitors, amide Hsp90 inhibitors, resorcinol-containing Hsp90 inhibitors, non-geldanamycin derivative Hsp90 inhibitors, purine-derived Hsp90 inhibitors as well as other types of Hsp90 inhibitors.

Ansamycin Hsp90 inhibitors include, but are not limited to, macbecin also known as (4E,6Z,8S,10E,12R,13S,14R,16S,17R)-13,14,17-trimethoxy-4,8,10,12,16-pentamethyl-3,20,22-trioxo-2-azabicyclo[16.3.1]docosa-1(21),4,6,10,18-pentaen-9-yl carbamate and by the IUPAC name: [(2R,3S,5S,6R,7S,8E,10R,11S,12Z,14E)-2,5,6-trimethoxy-3,7,9,11,15-pentamethyl-16,20,22-trioxo-17-azabicyclo[16.3.1]docosa-1(21),8,12,14,18-pentaen-10-yl]carbamate; and gamitrinibs also known as GAmitochondrial matrix inhibitors.

Ansamycin-derived Hsp90 inhibitors include, but are not limited to, geldanamycin, also known as E,6Z,8S,9S,10E,12S,13R,14S,16R)-13-hydroxy-8,14,19-trimethoxy-4,10,12,16-tetramethyl-3,20,22-trioxo-2-azabicyclo[16.3.1]docosa-1(21),4,6,10,18-pentaen-9-yl carbamate and by the IUPAC name: [(3R,5S,6R,7S,8E,10S,11S,12Z,14E)-6-hydroxy-5,11,21-trimethoxy-3,7,9,15-tetramethyl-16,20,22-trioxo-17-azabicyclo[16.3.1]docosa-1(21),8,12,14,18-pentaen-10-yl]carbamate; 17-AAG, also known as tanespimycin, CNF1010, KOS-953, 17-allylamino-17-desmethoxygeldanamycin and by the IUPAC name: [(3R,5S,6R,7S,8E,10S,11S,12Z,14E)-6-hydroxy-5,11-dimethoxy-3,7,9,15-tetramethyl-16,20,22-trioxo-21-(prop-2-enylamino)-17-azabicyclo[16.3.1]docosa-1(21),8,12,14,18-pentaen-10-yl] carbamate; 17-AAG hydroquinone also known as retaspimycin and 18,21-didehydro-17-demethoxy-18,21-dideoxo-18,21-dihydroxy-17-(2-propenylamino)geldanamycin, IPI-493 (retaspimycin hydrochloride formulated for oral administration), IPI-504 (retaspimycin hydrochloride formulated for i.v. administration) and 7-allylamino-17-desmethoxygeldanamycin-hydroquinone; 17-DMAG also known as alvespimycin, KOS-1022, 17-Dimethyl-aminoethylamino-17-demethoxygeldanamycin, N,N-dimethylethylamino analogue of 17-AAG, and by the IUPAC name: [(3R,5S,6R,7S,8E,10S,11S,12Z,14E)-21-(2-dimethylaminoethylamino)-6-hydroxy-5,11-dimethoxy-3,7,9,15-tetramethyl-16,20,22-trioxo-17-azabicyclo[16.3.1]docosa-1(21),8,12,14,18-pentaen-10-yl]carbamate; AB-010 which is a solvent-free albumin-bound form of 17AAG; and injectable suspension formulations of 17-AAG.

Amide Hsp90 inhibitors include, but are not limited to, SNX-2112 also known as 4-[6,6-dimethyl-4-oxo-3-(trifluoromethyl)-4,5,6,7-tetrahydro-1H-indazol-1-yl]-2-[(trans-4-hydroxycyclohexyl)amino]benzamide; SNX-5422 mesylate also known as SNX-5542 mesylate; SNX-7081; and AT13387.

Resorcinol-containing Hsp90 inhibitors include, but are not limited to, Resorcinol 7 also known as NVP-AUY922 and by the IUPAC name: (5Z)—N-ethyl-5-(4-hydroxy-6-oxo-3-propan-2-ylcyclohexa-2,4-dien-1-ylidene)-4-[4-(morpholin-4-ylmethyl)phenyl]-2H-1,2-oxazole-3-carboxamide; pochonin D also known by the IUPAC name: (4E,8E,11S)-18-chloro-15,17-dihydroxy-11-methyl-12-oxabicyclo[12.4.0]octadeca-1(14),4,8,15,17-pentaene-3,13-dione; Pochoxime A; Pochoxime B; Pochoxime C; STA-1474; and STA-9090.

Purine-derived Hsp90 inhibitors include, but are not limited to, NVP-HSP990; PU-H71 also known as 6-Amino-8-[(6-iodo-1,3-benzodioxol-5-yl)thio]-N-(1-methylethyl)-9H-purine-9-propanamine; PU24FC1 (see US 20080253965); PU-DZ8 (see US 20080253965); and Purine 6.

Other types of Hsp90 inhibitors include, but are not limited to, AV-142; BIIB028; BIIB-021 also known as CNF2024 and by the IUPAC name: N-(diaminomethylidene)-4-[4-(furan-2-carbonyl)piperazin-1-yl]-3-methylsulfonylbenzamide; methanesulfonic acid; SNX-0723 also known as 2-fluoro-6-[(3S)-tetrahydrofuran-3-ylamino]-4-(3,6,6-trimethyl-4-oxo-4,5,6,7-tetrahydro-1H-indol-1-yl)benzamid; Radicicol also known as monorden and as (1aR,2E,4E,14R,15aR)-8-chloro-9,11-dihydroxy-14-methyl-1a,14,15,15a-tetrahydro-6H-oxireno[e][2]benzoxacyclotetradecine-6,12(7H)-dione; KW-2478; MPC-3100; HSP990; and XL888.

Hsp90 inhibitors include, but are not limited to, retaspimycin hydrochloride (IPI-504, Infinity Pharmaceuticals) described in Peng et al., 2007; 17-amino-17-demethoxygeldanamycin (IPI-493); and 3-(5-chloro-2,4-dihydroxyphenyl)-N-ethyl-4-(4-methoxyphenyl)-1H-pyrazole-5-carboxamide, also known as VER-49009d described in Mol Cancer Ther 2007 April; 6(4):1198-211.

Hsp90 inhibitors are further described in Workman, Trends in Molecular Medicine 2004, vol. 10, pp 47-51; Biamonte et al. 2010, Journal of Medicinal Chemistry, 53 (1), 3-17; Solit, D. B. et al., 2008, Drug Discov. Today. 13:38-43; Taldone, T. et al., Current Opinion in Pharmacology 8, 370-374; Taldone, T. et al., Journal of Labelled Compounds and Radiopharmaceuticals 53, 47-49; U.S. Pat. Nos. 4,261,989; 7,138,401; 7,579,337; 7,566,706; and 7,691,840.

FLAP Inhibitors

The term "FLAP inhibitor" refers to an agent that decreases the level of a 5-lipoxygenase-activating protein (FLAP) and/or decreases at least one activity of a FLAP protein. Exemplary activities of FLAP include, for example, activation of 5-LO.

Combination therapies utilizing one or more 5-LO inhibitors and one or more FLAP inhibitors may show synergistic effects, e.g., a greater therapeutic effect than would be observed using either inhibitor as a monotherapy.

In certain embodiments, combinations therapies include one or more 5-LO inhibitors and at least FLAP inhibitor. Combinations of two or more FLAP inhibitors are included according to embodiments of the present invention.

In various embodiments, combination therapies including a 5-LO inhibitor may refer to (1) pharmaceutical compositions that include one or more 5-LO inhibitors in combination with one or more FLAP inhibitors; and (2) co-administration of one or more 5-LO inhibitors with one or more FLAP inhibitors wherein the 5-LO inhibitor and the FLAP inhibitor have not been formulated in the same composition. When using separate formulations, the 5-LO inhibitor may be administered at the same time, intermittent times, staggered times, prior to, subsequent to, or combinations thereof, with reference to the administration of the FLAP inhibitor.

A FLAP inhibitor included in embodiments of methods and compositions of the present invention includes, but is not limited to, 1-[(4-chlorophenyl)methyl]3-[(1,1-dimethylethyl)thio]-α, α-dimethyl-5-(1-methylethyl)-1H-indole-2-propanoic acid, also known as MK886 and 3-(1((4-chlorophenyl)methyl)-3-((1,1-dimethylethyl)thio)-5-(quinolin-2-ylmethyloxy)-1H-indol-2-yl)-2,2-dimethyl-propanoate also known as MK-0591 or MK591 (Brideau et al. Ca. J. Physiol.

Pharmacol 1992 70:799-807). BAY-X-1005 is a FLAP inhibitor also known as 2-(4-(quinolin-2-yl-methoxy)phenyl)-2-cyclopentylacetic acid, described in Muller-Peddinghaus, R., et al., (1993). J. Pharmacol. Exp. Ther., 267, 51-57. AM679 is a FLAP inhibitor also known as 3-[5-((S)-1-Acetyl-2,3-dihydro-1H-indol-2-5-ylmethoxy)-3-tert-butylsulfanyl-1-[4-(5-methoxy-pyrimidin-2-yl)-benzyl]-1H-indol-2-yl]-2,2-6 dimethyl-propionic acid.

Additional FLAP inhibitors included in embodiments of methods and compositions of the present invention include, but are not limited to, those detailed in: U.S. Pat. No. 7,405,302; WO2009055721 and WO2009045700.

Protein Synthesis Inhibitors

A protein synthesis inhibitor included in embodiments of methods and compositions of the present invention includes, but is not limited to, omacetaxine mepesuccinate. Omacetaxine mepesuccinate induces apoptosis by inhibition of protein synthesis.

Additional Therapeutic Agents

Additional therapeutic agents included in embodiments of methods and compositions of the present invention include, but are not limited to, non-steroidal anti-inflammatory agents, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, steroids and vasoactive agents.

One or more additional leukemia therapeutics is optionally included in compositions and methods according to embodiments of the present invention. Exemplary leukemia therapeutics include, but are not limited to, AG-858, alemtuzumab, bortezomib, GVAX leukemia vaccine, lonafarnib and tipifarnib.

AG-858, also known as HSPPC-70, is an autologous polyvalent heat shock protein-peptide complex vaccine used for treatment of CML.

Alemtuzumab is an anti-CD52 mAb used for treatment of CLL and CTCL.

Bortezomib, also known as PS-341, [(1R)-3-methyl-1-({(2S)-3-phenyl-2-[(pyrazin-2-ylcarbonyl)amino]propanoyl}amino)butyl]boronic acid and by the IUPAC name: [(1S)-3-methyl-1-[[(2R)-3-phenyl-2-(pyrazine-2-carbonylamino)propanoyl]amino]butyl]boronic acid, is a proteasome inhibitor used for treating relapsed multiple myeloma and mantle cell lymphoma.

Tipifarnib, also known as 6-[amino(4-chlorophenyl)(1-methyl-1H-imidazol-5-yl)methyl]-4-(3-chlorophenyl)-1-methylquinolin-2(1H)-one and by the IUPAC name: 6-[(R)-amino-(4-chlorophenyl)-(3-methylimidazol-4-yl)methyl]-4-(3-chlorophenyl)-1-methylquinolin-2-one, is a farnesyl transferase inhibitor.

Lonafarnib, also known as 4-(2-(4-(8-Chloro-3,10-dibromo-6,11-dihydro-5H-benzo(5,6)cyclohepta(1,2-b)pyridin-11-yl)-1-piperidinyl)-2-oxoethyl)-1-piperidinecarboxamide, is a farnesyl transferase inhibitor.

Suitable anti-cancer agents include, but are not limited to, antimetabolites, alkylating agents, interferon alfa 2b, and steroids.

Particular examples of anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, droloxifene, dromostanolone, duazomycin, edatrexate, eflornithine, elsamitrucin, enloplatin, enpromate, epipropidine, epirubicin, erbulozole, esorubicin, estramustine, estramustine, etanidazole, etoposide, etoposide, etoprine, fadrozole, fazarabine, fenretinide, floxuridine, fludarabine, fluorouracil, fluorocitabine, fosquidone, fostriecin, fulvestrant, gemcitabine, gemcitabine, hydroxyurea, idarubicin, ifosfamide, ilmofosine, interleukin 2, interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, puromycin, pyrazofurin, riboprine, rogletimide, safingol, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vindesine, vinepidine, vinglycinate, vinleurosine, vinorelbine, vinrosidine, vinzolidine, vorozole, zeniplatin, zinostatin, zoledronate, and zorubicin.

Inhibitor Modification

Half-life of a 5-LO inhibitor or other therapeutic agent can be increased by adding moieties, such as polyethylene glycol, polyglutamic acid (PGA), polylactic acid (PLA), monomethoxy-polyethylene glycol-polylactic acid, heparin, collagen, hyaluronic acid, gelatin, transferrin, albumin, biotin or an Fc fragment.

Pharmaceutical Compositions and Methods of Administration

Therapeutic agents described herein can be used in various forms depending on the particular therapeutic agent and factors such as the intended route of administration. Therapeutic agents can be used as the free acid, free base, pharmaceutically acceptable salt, hydrate or solvate, for example. Racemic and chiral forms are contemplated as within the scope of the present invention along with isomorphic crystalline forms. The term "pharmaceutically acceptable" refers to compositions, materials, compounds and formulations suitable for contact with human or animal tissues without unreasonable benefit/risk ratio.

Therapeutic agents described herein such as 5-LO inhibitors, Hsp90 inhibitors, kinase inhibitors, FLAP inhibitors, and additional therapeutic agents may be formulated in a conventional manner using one or more pharmaceutically acceptable carriers or excipients. For example, therapeutic agents and their pharmaceutically acceptable salts, hydrates and solvates may be formulated for administration by, for example, injection, inhalation or insufflation (either through the mouth or the nose) or oral, buccal, parenteral or rectal administration or transdermal delivery. In one embodiment, a therapeutic agent may be administered locally, at the site where the target cells are present, i.e., in a specific tissue, organ, or fluid (e.g., blood, cerebrospinal fluid, etc.).

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

The therapeutic agents can be formulated for a variety of modes of administration, including systemic and topical or localized administration. Techniques and formulations generally may be found in Remington's Pharmaceutical Sciences, Meade Publishing Co., Easton, Pa. For systemic administration, injection is preferred, including intramuscular, intravenous, intraperitoneal, and subcutaneous. For injection, the inhibitors can be formulated in liquid solutions, preferably in physiologically compatible buffers such as Hank's solution or Ringer's solution. In addition, the inhibitors may be formulated in solid form and redissolved or suspended immediately prior to use. Lyophilized forms are also included.

For oral administration, the pharmaceutical compositions may take the form of, for example, tablets, lozenges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art, and may include multi-layered coatings to achieve controlled release dosage forms. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation, the therapeutic agents may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the inhibitor and a suitable powder base such as lactose or starch.

The therapeutic agents may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The therapeutic agents may also be formulated in rectal compositions such as suppositories or retention enemas, e.g., containing conventional suppository bases such as cocoa butter or other glycerides.

In addition to the formulations described previously, the therapeutic agents may also be formulated as a depot preparation. Such long acting formulations may be administered by implantation (for example subcutaneously or intramuscularly) or by intramuscular injection. Thus, for example, the therapeutic agents may be formulated with suitable polymeric or hydrophobic materials (for example as an emulsion in an acceptable oil) or ion exchange resins, or as sparingly soluble derivatives, for example, as a sparingly soluble salt.

Dosage levels of between about 0.01 and about 100 mg/kg body weight per day preferably between about 0.5 and about 75 mg/kg body weight per day of a 5-LO inhibitor are useful for treating leukemia and/or preventing the transition from chronic or accelerated phase leukemia to acute phase leukemia. In a particular example, dosing of a 5-LO inhibitor for an adult human is 4 times daily with 600 mg or 2× daily with 1200 mg.

The amount of active ingredient that may be combined with the carrier materials to produce a single dosage form will vary depending upon the subject treated and the particular mode of administration. A typical preparation may include from about 0.00001 to 100% such as from 0.001 to 10% or from 0.1% to 5% by weight of one or more inhibitors described herein.

The terms "systemic administration," "administered systemically," "peripheral administration" and "administered peripherally" are art-recognized and refer to the administration of a subject composition, therapeutic agent or other material other than directly into the central nervous system, such that it enters the patient's system and, thus, is subject to metabolism and other like processes.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) dextran; and (22) other non-toxic compatible substances employed in pharmaceutical formulations.

In particular embodiments, a pharmaceutically acceptable carrier is a particulate carrier such as lipid particles including liposomes, micelles, unilamellar or mulitlamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate pharmaceutically acceptable carrier can be selected from among a lipid particle; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 nm-10 microns. In particular embodiments, a particulate carrier is formulated such that particles have an average particle size in the range of about 1 nm-100 nm.

Nanoparticulate formulations of pharmaceutically acceptable carriers include, for example, nanoparticulate polymers, dendrimers, liposomes, viruses, carbon nanotubes, and metals such as iron oxide and gold. Exemplary polymers for the preparation of nanoparticles include natural polymers such as heparin, dextran, albumin, gelatine, alginate, collagen, and chitosan or synthetic polymers including polyethylene glycol (PEG), polyglutamic acid (PGA), polylactic acid (PLA), polycarprolactone (PCL) and N-(2-hydroxypropyl)-methacrylamide copolymer (HPMA). Additional nanoparticulate carriers are described in Wang et al. Cancer Res Treat. 2009; 41(1): 1-11).

The term "therapeutic effect" is art-recognized and refers to a local or systemic effect in animals, particularly mammals, and more particularly humans caused by a pharmacologically active substance. The phrase "therapeutically-effective amount" means the amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions described herein may be administered in a sufficient amount to produce a desired effect at a reasonable benefit/risk ratio applicable to such treatment.

Toxicity and therapeutic efficacy of the inhibitors can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. The inhibitors that exhibit large therapeutic indexes are preferred. While the inhibitors that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The terms "patient", "subject" and "individual" are used herein to refer to either a human or a non-human animal. The term animal refers to a living multi-cellular vertebrate organism, including for example, mammals and birds. The term mammal includes both human and non-human mammals. Similarly, the term "subject" includes both human and veterinary subjects.

The term "mammal" is known in the art, and exemplary mammals include humans, primates, livestock animals such as sheep, cattle, goats, horses and pigs; companion animals such as cats and dogs; rabbits; and rodents such as mice, guinea pigs and rats.

The term "sample" refers to a sample obtained from a biological organism, particularly a subject as described herein. Non-limiting examples of samples include, bone marrow, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, and vitreal fluid, and nasal secretions.

Staging and Assessment of Myeloproliferative Disorders

In certain embodiments, the methods described herein may be used for treating and/or preventing several different leukemic disease states. Prior to, during, and/or following, the administration of a 5-LO inhibitor according to embodiments of the present invention, patients suffering from leukemia may optionally be staged to determine the severity of the leukemia. Staging may include determining the number of blasts, promyelocytes, basophil, and platelets per liter of peripheral blood or bone marrow, as described further below.

Unlike other forms of leukemia, CML is a relatively homogeneous disease. Almost all patients with CML (90%) have the same chromosomal abnormality in their leukemic cells. The chromosomal abnormality can be identified by cytogenetic testing, including PCR testing and/or Fluorescence In Situ Hybridization (FISH). In up to 40% of CML patients, the disease progresses directly from the chronic to the blastic phase. Cortes and Kantarjian (1998) in Cancer management: a multidisciplinary approach, 2d ed. Huntington, N.Y.: Publisher Research Management, Inc, p306-15. Blast transformation typically occurs at 3 to 5 years, but onset is random and may be observed at the time of initial diagnosis. Common features for chronic phase CML patients include fatigue, weight loss, and signs or symptoms of splenomegaly (e.g., left upper quadrant pain, abdominal fullness, a palpable mass), which occurs in up to 70% of patients. Cortes et al (1996) Am J Med 100(5):555-70. Patients with extreme elevations in white blood cell count (hyperleukocytosis) may demonstrate signs or symptoms of leukostasis, including mental status changes, focal neurologic deficits, tinnitus, dyspnea, and priapism. Retinal hemorrhages or other bleeding manifestations may appear irrespective of platelet counts. This is attributable to the qualitative platelet dysfunction that is common in CML. Goldman (1997) BMJ (Clin Res Ed) 314:657-60.

As CML progresses from chronic phase to accelerated phase, the patient may experience fever, night sweats, weight loss, and progressive splenomegaly. More often, however, there is no significant change in symptoms, and onset is heralded by hematologic progression (e.g., worsening of blood counts) or cytogenetic evolution (e.g., development of new chromosomal abnormalities). As CML progresses from the accelerated phase to blast phase, the patient may experience fever, weight loss, night sweats, bone pain, and constitutional symptoms. Lymphadenopathy, leukemia cutis, central nervous system disease, and bleeding secondary to progressive thrombocytopenia also may occur. Hughes and Goldman (1995) in Hematology: basic principles and practice, 2d ed. New York: Churchill Livingstone, p1142-59.

CML staging involves the use of a system of categorization to describe the seriousness of the CML and attempts to put patients with similar prognosis and treatment in the same staging group. Staging is important in developing CML treatment strategies as it allows doctors to compare the efficacy of different treatments for patients with similar conditions, and aids in the determination of treatment decisions. Staging systems for CML are generally based on clinical features with demonstrated prognostic significance, including age, size of spleen, percentage of circulating and marrow blasts, degree of basophilia, extent of thrombocytosis, and presence of atypical chromosomal abnormalities. Faderl S., et al., Ann. Intern. Med., 131: 207-219, 1999; Grier H E and Civin C I, Myeloid Leukemias, Myelodysplasia, and Myeloproliferative Diseases in Children. In (Nathan and Oski, eds) Hematology of Infancy and Childhood, volume 2, 5$^{th}$ Edition, W.B. Saunders Company, 1998; 34:1286-1459; Santini V. et al., Ann. Intern. Med., 134: 573-586, 2001; Lubbert M et al., Br J Haematol 2001 August; 114(2):349-357. In addition, specific response to interferon alpha-2b therapy is considered to be a particularly sensitive predictor of long-term survival following treatment. Goldman (1997) Baillieres Clin Haematol 10(2):405-21.

Patients with CML in the chronic phase have all of the following conditions: less than 15% blasts in the peripheral blood or bone marrow; less than 30% blasts and promyelocytes in the peripheral blood or bone marrow; less than 20% basophils in the peripheral blood; $100 \times 10^9$ per liter platelets; and no extramedullary involvement other than liver or spleen. Patients with CML in the accelerated phase have at least one of the following conditions: 15% to less than 30% blasts in the peripheral blood or bone marrow; 30% blasts and promyelocytes in the peripheral blood or bone marrow (but less than 30% blasts in the peripheral blood or bone marrow); 20% basophils in the peripheral blood; or less than $100 \times 10^9$ per liter platelets.

Blast phase CML patients have at least 30% blasts and promyelocytes in the peripheral blood or bone marrow, or extramedullary involvement other than liver or spleen. In certain embodiments, blast phase CML patients treated using a 5-LO inhibitor may be two years of age or older, have histologically confirmed diagnosis of blast phase CML, were previously treated with imatinib mesylate with no response or resulted in loss of response, and/or have bilirubin levels greater than or equal to 1.5 times the upper limit of normal, serum glutamic-oxaloacetic transaminase and serum glutamic-pyruvic transaminase levels greater than or equal to 2.5 times the upper limit of normal, and/or serum creatine levels greater than or equal to 1.5 times the upper limit of normal.

Patients with CML in chronic, accelerated or blast phase, who are resistant to standard therapy generally have a relatively poor prognosis with a rapid progression to blast crisis, bone marrow failure and death. To measure the success of a therapeutic treatment of CML, hematologic responses or cytogenetic responses or molecular responses are determined. In the case of a complete response, the spleen of the patient should not be palpable. A complete hematologic response is defined as maintaining the following conditions for four weeks: less than or equal to 5% blasts in bone marrow; no peripheral blood blasts; absolute neutrophil count of greater than $1.5 \times 10^9$ per liter; platelet count of greater than $100 \times 10^9$ per liter; and no extramedullary involvement. In the differential blood count no immature granulocyte (monocytes, polymorphonuclear cells (PMC), myeloblasts (MB)) and less than 5% basophils should be detectable.

Achieving a cytogenetic response has been established as a surrogate marker for an improved probability of survival in CML. A complete cytogenetic response (CCyR) is the detection of 0% Philadelphia chromosome in 20 metaphases analyzed (G banding); a partial response (PCyR) is the detection of 1% to 35% Philadelphia chromosomes; a minor response (MCyR) is the detection of 36% to 65%; and minimal response is the detection of 66% to 95% Philadelphia chromosomes in 20 metaphases. Instead of G banding, interphase fluorescence in situ hybridization (FISH) analysis can be performed on either blood or bone marrow samples.

To measure the therapeutic effect, the molecular response may be analyzed using blood or bone marrow and isolating RNA for quantitative RT-PCR analysis. No BCR-ABL transcripts are detectable in the case of a complete response. Detection of 0.10 or lower compared to the control gene ratio is considered a major molecular response. Diagnostic kits for the molecular diagnosis are provided for example by Ipsogen, Marseille, France; MolecularMD, Portland, Oreg. 97219, USA; TrimGen, Sparks, Md., USA; Genedia Srl, Lammari, Italy, and DxS, a Qiagen company, Manchester, UK.

The Philadelphia chromosome, with the BCR-ABL oncogene detectable at the molecular level, is present at diagnosis in 95% of patients. Optionally, complete hematologic responses are further classified according to suppression of the Philadelphia chromosome (Ph). For example, a patient with complete hematologic response and greater than 65% Ph positive is classified as no cytogenetic response. Patient responses that are 36% to 65% Ph positive are classified as minimal cytogenetic responses, 1% to 35% Ph positive are partial cytogenetic responses, and 0% Ph positive are complete cytogenetic responses.

In certain embodiments, a partial hematologic response may be defined as maintaining the following conditions for four weeks: less than or equal to 5% blasts in bone marrow; no peripheral blood blasts; absolute neutrophil count of less than $1.5 \times 10^9$ per liter; and platelet count of less than $100 \times 10^9$ per liter.

In certain embodiments, a hematologic improvement may be defined as maintaining the following conditions for four weeks: less 15% blasts in bone marrow and peripheral blood; less than 40% blasts and promyelocytes in peripheral blood and blood marrow; less than 20% basophils in peripheral blood; and no extramedullary involvement other than liver or spleen.

The term "accelerated phase", with reference to leukemia, refers to a stage of leukemia wherein blood or bone marrow samples from subjects have more than about 10% blasts (or more than about 20% blasts and promyelocytes) but less than about 30% blasts and promyelocytes.

The terms "acute phase" or "blast phase" or "blast crisis", with reference to leukemia, refers to a stage of leukemia wherein blood and/or bone marrow samples from subjects have more than about 30% blasts and promyelocytes. Acute phase leukemia may include acute lymphocytic leukemia (ALL) and/or acute myelogenous leukemia (AML). An exemplary form of ALL is B-cell acute lymphoblastic leukemia (B-ALL).

The term "blast" refers to immature blood cells. The term "chronic phase", with reference to leukemia, refers to a stage of leukemia wherein subjects have less than about 10% blasts (or less than about 20% blasts and promyelocytes) in blood or bone marrow samples. Chronic phase leukemia may include chronic lymphocytic leukemia (CLL) and/or chronic myelogenous leukemia (CML).

The term "lymphoid cells" is art recognized and refers to cells of the lymphatic system including, T-cells, B-cells, NK-cells, and dendritic cells.

The term "myeloid cells" is art recognized and refers to all hematopoietic cells other than the lymphoid cells. Exemplary myeloid cells include, for example, dendritic cells (e.g., Langerhans cells), monocytes (e.g., macrophages and osteoclasts), neutrophils, eosinophils, basophils, megakaryocytes (e.g., platelets), and erythrocytes.

The term "preventing transition," with reference to a subject suffering from leukemia, refers to preventing the percentage of blasts and promyelocytes in blood and/or bone marrow samples from increasing to 30% or above. In one embodiment, preventing transition refers to preventing the transition from chronic or accelerated phase leukemia to acute phase leukemia. In an exemplary embodiment, preventing transition refers to preventing the transition from chronic myeloid leukemia (CML) to acute phase leukemia, e.g., AML or ALL, especially B-ALL. Preventing transition, with reference to a subject having less than 30% blasts and promyelocytes in blood and/or bone marrow samples, includes maintaining the percentage at less than 30%, decreasing the percentage from less than 30% to an even lower percentage, as well as increasing the percentage from a given level to a greater level that is less than 30% (e.g., increasing from 15% to 20%).

In one embodiment, the methods provided herein are directed to treating leukemia that is resistant and/or insensitive to BCR-ABL kinase inhibition therapy. In an exemplary embodiment, the 5-LO inhibitor may be administered to a subject who has already manifested intolerance to a BCR-ABL kinase inhibitor, such as, for example, imatinib mesylate, within 6 months of the treatment with the BCR-ABL kinase inhibitor. The subject's intolerance to a BCR-ABL kinase inhibitor can be defined by manifesting symptoms or adverse effects such hepatoxicity, fluid retention syndrome, neutropenia, hemorrhage, dyspepsia, dyspnea, diarrhea, muscle cramps, skin rash, fatigue, headache, nausea, vomiting, and thrombocytopenia. Such patients may be treated with at least one 5-LO inhibitor or a combination of at least one 5-LO inhibitor and at least one BCR-ABL inhibitor or Src kinase inhibitor or Hsp90 inhibitor, preferably an inhibitor that is different from the one to which the subject has already manifested an intolerance. For example, a BCR-ABL inhibitor that may be suitable may have a different structure or may inhibit the protein by a different mechanism.

Commercial Packages

Commercial packages are provided according to embodiments of the present invention for treating a myeloproliferative disorder in a subject having, or at risk of having, a myeloproliferative disorder which include a 5-LO inhibitor. Optionally, one or more auxiliary components are included in inventive commercial packages, such as pharmaceutically acceptable carrier such as a buffer, a diluent or a reconstituting agent.

Optionally, a commercial package according to embodiments of the present invention includes an additional therapeutic agent, such as a tyrosine kinase inhibitor, a bcr-abl tyrosine kinase inhibitor, a FLAP inhibitor, a src kinase inhibitor, an Hsp90 inhibitor, a heat shock protein 90 inhibitor, an anti-metabolite, an alkylating agent, a steroid, interferon alpha 2b; and a combination of any two or more thereof. In a further option a composition of the present invention is included in a commercial package.

Diagnostic Aids

Methods of aiding in diagnosis of a myeloproliferative disorder in a subject are provided according to embodiments of the present invention which include detecting arachidonate 5-lipoxygenase in a sample obtained from the subject.

In particular embodiments, a sample obtained from a subject is assayed for ALOX5 levels and/or activity to aid in determining whether the subject has a myeloproliferative disorder to be treated according to embodiments of methods of the present invention. Thus, for example, methods are provided which include detecting elevated ALOX5 in a sample obtained from the subject, such as detecting an elevated level of ALOX5 expression, detecting an elevated level of ALOX5 activity, detecting an elevated level of an ALOX5 metabolite; or a combination of any of these.

In particular embodiments, a bone marrow sample obtained from a subject is assayed for ALOX5 levels and/or activity to aid in determining whether the subject has a myeloproliferative disorder to be treated according to embodiments of methods of the present invention. Thus, for example, methods are provided which include detecting elevated ALOX5 in a bone marrow sample obtained from the subject, such as detecting an elevated level of ALOX5 expression, detecting an elevated level of ALOX5 activity, detecting an elevated level of an ALOX5 metabolite; or a combination of any of these.

In further embodiments, a sample enriched for leukemia stem cells obtained from a subject is assayed for ALOX5 levels and/or activity to aid in determining whether the subject has a myeloproliferative disorder to be treated according to embodiments of methods of the present invention. Thus, for example, methods are provided which include detecting elevated ALOX5 in a bone marrow sample obtained from the subject which is enriched for leukemia stem cells, such as detecting an elevated level of ALOX5 expression, detecting an elevated level of ALOX5 activity, detecting an elevated level of an ALOX5 metabolite; or a combination of any of these. A sample can be enriched in leukemia stem cells by FACS, for example.

In one embodiment, detecting an elevated level of an ALOX5 metabolite includes detection of LTB4 in a sample obtained from the subject. In a further embodiment, detecting an elevated level of an ALOX5 metabolite includes detection of LTB4 or LTC4 in a sample obtained from the subject. In some embodiments the sample is a plasma sample or a bone marrow sample.

Embodiments of inventive compositions and methods are illustrated in the following examples. These examples are provided for illustrative purposes and are not considered limitations on the scope of inventive compositions and methods.

EXAMPLES

Example 1

Identification of Alox5 in CML

Leukemic stem cells in CML (CML-SCs) are insensitive to BCR-ABL kinase inhibitors (Graham et al., 2002). A bone marrow transplantation (BMT) mouse model of CML is used as an assay system, in which bone marrow cells from donor mice pretreated with 5-fluorouracil (5-FU) and transduced with BCR-ABL result in development of CML in recipient mice (Li et al., 1999). Bone marrow cells from C57BL/6 (B6) mice are transduced with retrovirus containing BCR-ABL/GFP or GFP alone under conditions for induction of CML, followed by transplantation of the transduced cells into B6 recipient mice. Some mice are treated with the BCR-ABL kinase inhibitor imatinib (150 mg/kg body weight/per dose, once every 4 hours; orally by gavage) for 5 doses beginning at day 13 post bone marrow transplantation (BMT) to allow identification of genes that are altered by BCR-ABL in LSCs, but this alteration is not restored by inhibition of BCR-ABL kinase activity with imatinib. Some pathways are activated by BCR-ABL but are insensitive to inhibition by imatinib (Hu et al., 2006).

Fourteen days after BMT, bone marrow cells are isolated and subsequently sorted by FACS for LSCs (GFP$^+$Lin$^-$c-Kit$^+$Sca-1$^+$) (Hu et al., 2006). Total RNA is isolated from these BCR-ABL-expressing LSCs or from the GFP$^+$Lin$^-$c-Kit$^+$Sca-1$^+$ cells that only express GFP, and DNA microarray analysis is carried out to compare gene expression between BCR-ABL-expressing and non-BCR-ABL expressing Lin$^-$c-Kit$^+$Sca-1$^+$ cells. The Alox5 gene is up-regulated and this upregulation is not abolished by imatinib treatment as shown in FIG. 1.

Figure 2:
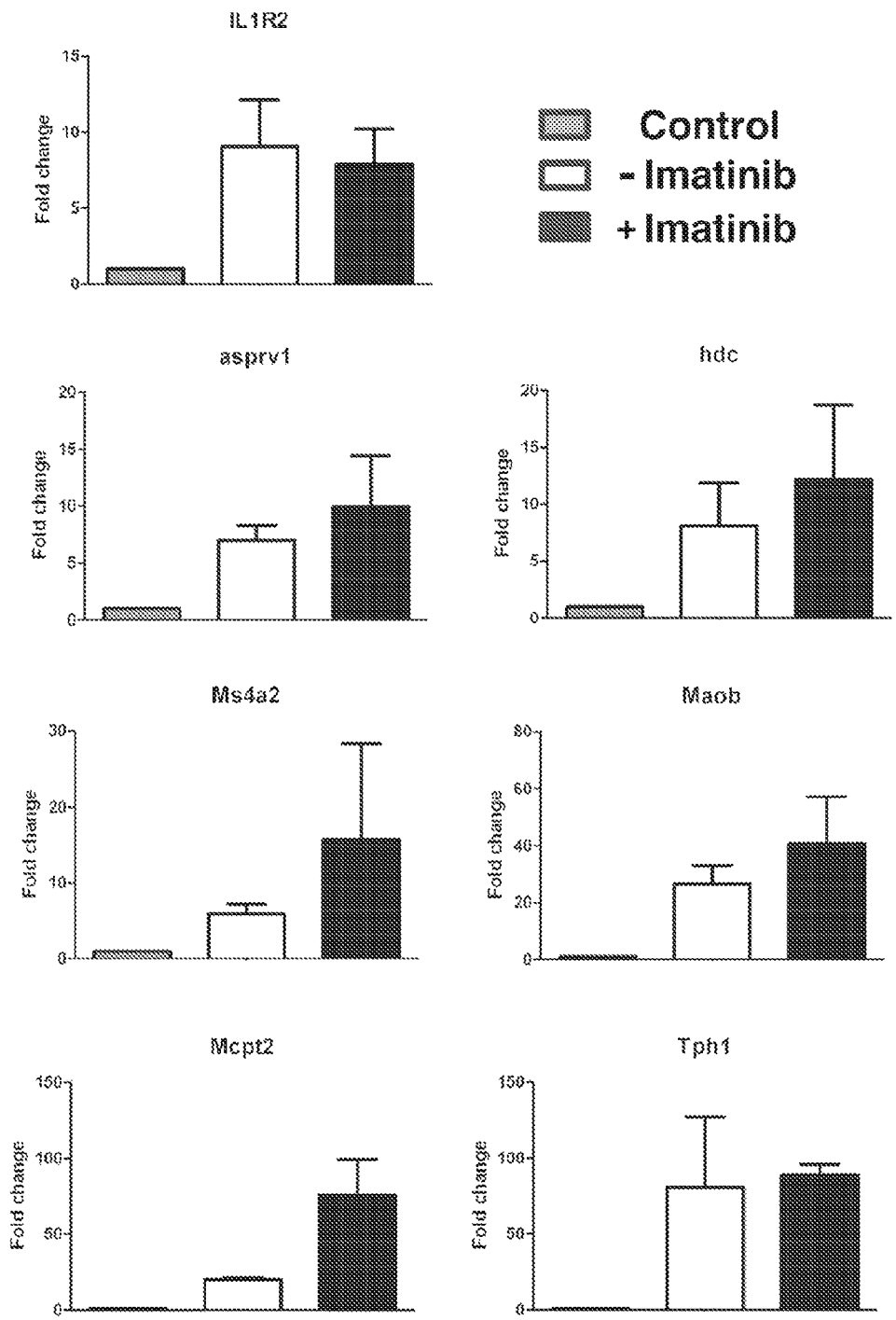
FIG. 2 is a set of graphs showing a quantitative RT-PCR analysis of genes that are up-regulated by BCR-ABL in LSCs (-imatinib; open boxes) and not changed in expression following imatinib treatment (+imatinib, filled boxes) compared to normal control (grey boxes)

Several additional genes (IL1R2, asprvl, hdc, Ms4a2, Maob, Mcpt2, Tph1) are also up-regulated by BCR-ABL and not changed in expression following imatinib treatment determined by RT-PCR and as shown in FIG. 2.

Figure 3:
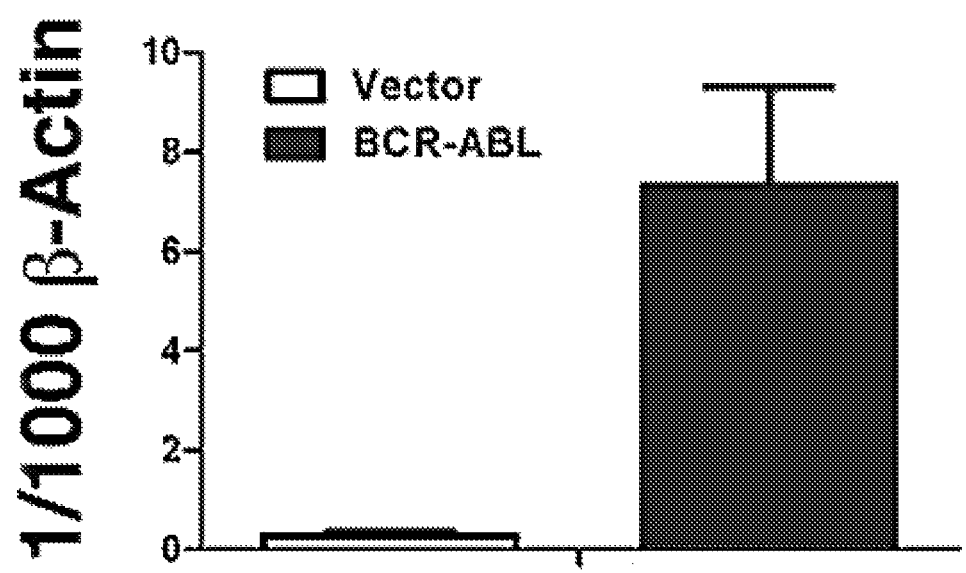
FIG. 3 is a graph showing Alox5 gene expression being upregulated in BCR-ABL positive LSCs (BCR-ABL, filled box) when compared to GFP vector-transduced normal stem cells (vector, open box) (p<0.001) as determined by RT-PCR.

The up-regulation of Alox5 by BCR-ABL in LSCs is confirmed by RT-PCR of isolated and FACS sorted (GFP$^+$Lin$^-$c-Kit$^+$Sca-1$^+$) bone marrow cells as shown in FIG. 3.

Figure 4:
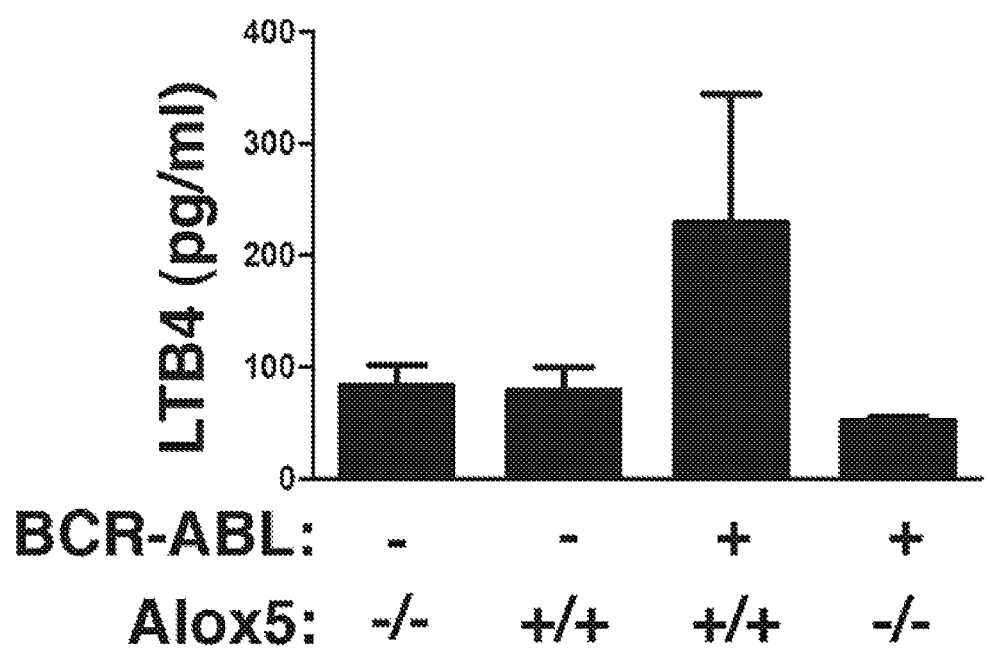
FIG. 4 is a graph showing analysis of the plasma level of leukotriene B4 (LTB4) in recipients of BCR-ABL-transduced bone marrow cells and controls.

A BCR-ABL-mediated increase in Alox5 function is also shown by measuring levels of leukotriene B4 (LTB4) in the bone marrow recipients, which is synthesized and metabolized through the ALOX5 pathway, in peripheral blood of the transplanted mice. Plasma level of LTB4 is increased in CML mice (BCR-ABL$^+$/Alox5$^+$), but not in the control groups (BCR-ABL$^-$, Alox5$^{-/-}$; BCR-ABL$^-$, Alox5$^+$; BCR-ABL$^+$, Alox5$^{-/-}$) as shown in FIG. 4.

Example 2

Alox5 is Essential for CML Induction by BCR-ABL

Alox5 homozygous knockout (Alox5$^{-/-}$) mice are used in this example to determine the effect of Alox5 on LSC function. Wild type or Alox5$^{-/-}$ donor bone marrow cells on the B6 strain background are used to induce CML.

Figure 5:
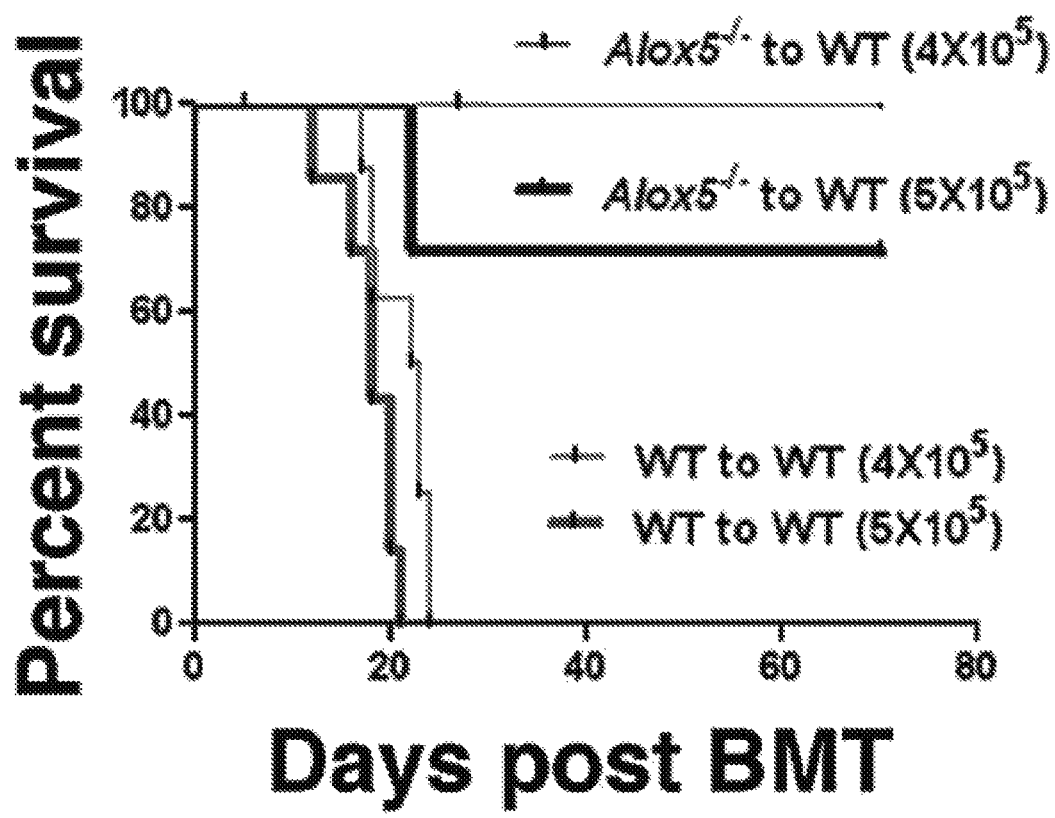
FIG. 5 is a graph showing Kaplan-Meier survival curves for recipients of BCR-ABL-transduced bone marrow cells from wild type or Alox5$^{-/-}$ donor mice and showing mean percentage for each group (n=5)

Kaplan-Meier survival curves for recipients of BCR-ABL-transduced bone marrow cells from wild type or Alox5$^{-/-}$ donor mice (10 mice per group) are determined. Recipients of BCR-ABL-transduced bone marrow cells from 5-FU-treated wild type donor mice developed and died of CML within 4 weeks, whereas recipients of BCR-ABL-transduced bone marrow cells from Alox5$^{-/-}$ donor mice are resistant to induction of CML and survived, as shown in FIG. 5. This defective disease phenotype correlates with much less severe infiltration of myeloid leukemia cells in the lung and spleen. Gross appearance of the lungs and spleens showed severe lung hemorrhages and splenomegaly of recipients of BCR-ABL-transduced bone marrow cells from wild type but not Alox5$^{-/-}$ donor mice. Haematoxylin and eosin-stained lung and spleen sections from recipients of BCR-ABL-transduced bone marrow cells from wild type or Alox5$^{-/-}$ donor mice confirmed the gross findings.

FACS analysis of CML cells in peripheral blood and bone marrow shows that Gr-1+ myeloid leukemia cells grow initially, reach a peak after 2 weeks, then start to decline, and eventually disappear after 7 weeks in peripheral blood and bone marrow of recipients receiving BCR-ABL-transduced Alox5$^{-/-}$ donor bone marrow cells.

Figure 6:
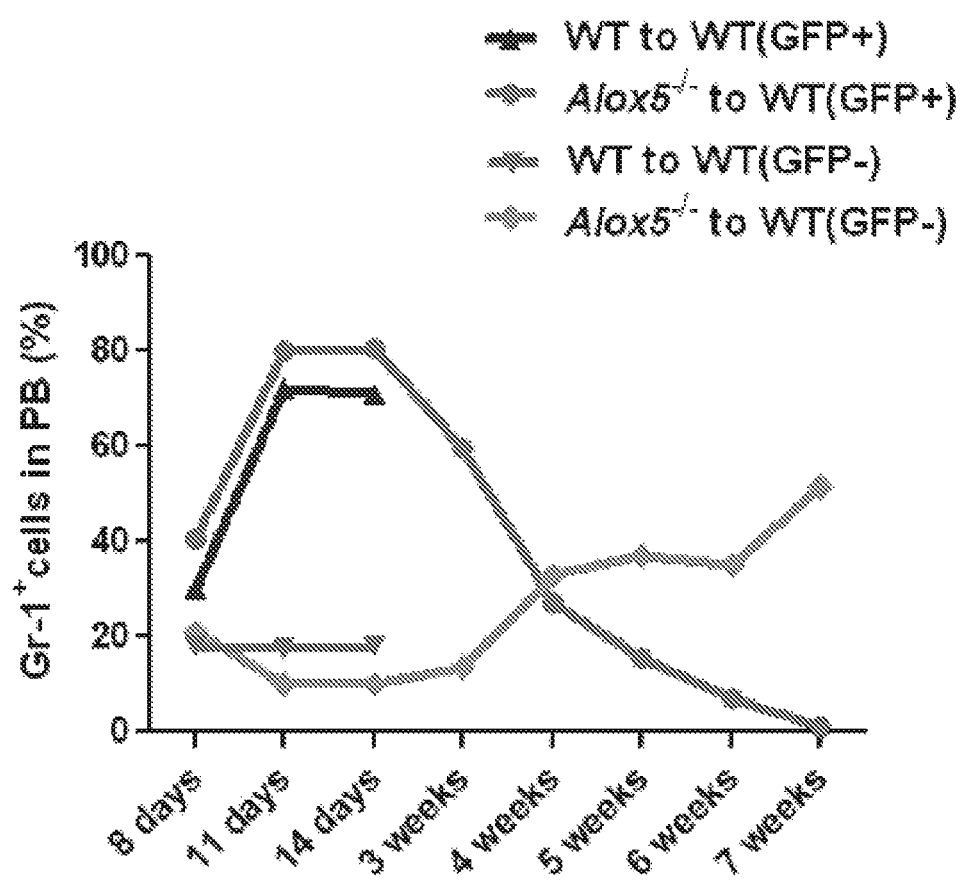
FIG. 6 is a graph showing that Alox5 deficiency mainly affects growth of BCR-ABL-expressing (GFP$^+$) but not non-BCR-ABL-expressing (GFP$^-$) donor bone marrow cells.

In recipients of BCR-ABL-transduced bone marrow cells from Alox5$^{-/-}$ donor mice, GFP$^+$Gr-1$^+$ cells in PB gradually decreased with time, whereas the GFP$^-$Gr-1$^+$ cells that did not express BCR-ABL gradually increased, showing that Alox5 deficiency significantly inhibited engraftment of BCR-ABL-expressing but not normal BM cells in the same animals. Mean percentage for each group (n=5) is shown in FIG. 6, Thus, Alox5 is essential for induction of CML by BCR-ABL.

Example 3

Alox5 Rescues Defective CML

BCR-ABL and Alox5 are co-expressed in Alox5$^{-/-}$ and wild type bone marrow cells, respectively, in this example by retroviral transduction, followed by transplantation of the transduced cells into recipient mice.

Figure 7A:
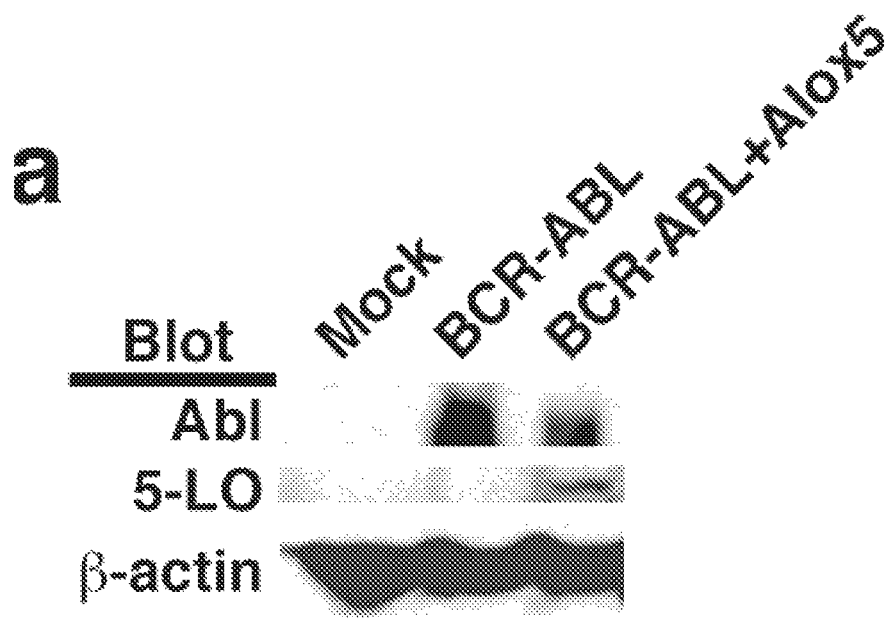
FIG. 7a is an image of a Western blot of negative control (mock), BCR-ABL-IRES-GFP-pMSCV-transfected (BCR-ABL) 293T cells and rescue construct (BCR-ABL+Alox5) transfected 293T cells using antibodies against ABL and ALOX5.
Figure 7B:
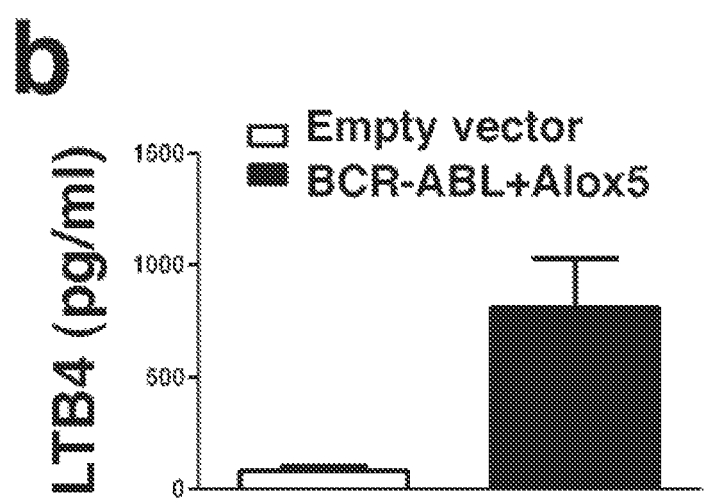
FIG. 7b is a graph showing LTB4 production in mice with a significant increase in mice expressing BCR-ABL and Alox5.
Figure 7C:
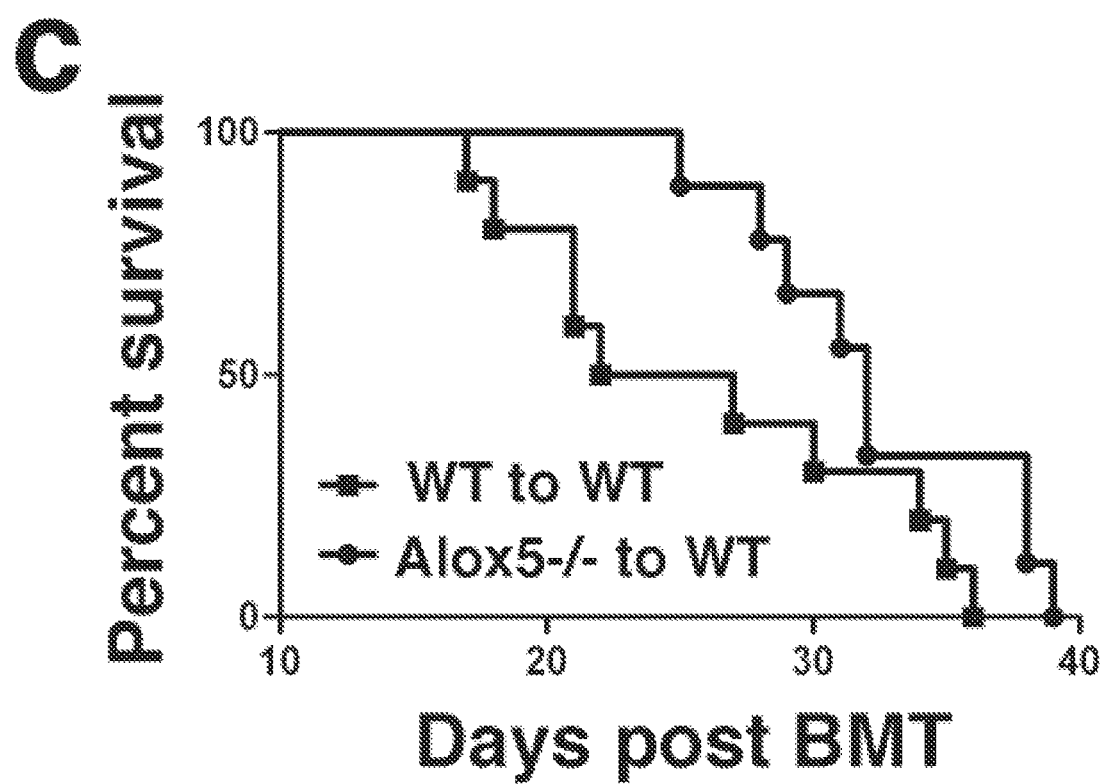
FIG. 7c is a graph showing Kaplan-Meier survival curves for recipients of BCR-ABL-IRES-Alox5-pMSCV-transduced bone marrow cells from wild type (n=10) or Alox5$^{-/-}$ (n=9) donor mice and indicating that all recipient mice die by 40 days.

293T cells are transfected with mock, BCR-ABL-IRES-GFP-pMSCV or BCR-ABL-IRES-Alox5-pMSCV. BCR-ABL and 5-LO expression are detected by Western blotting using antibodies against Abl and 5-LO. The BCR-ABL-IRES-Alox5-pMSCV construct expresses both, BCR-ABL and ALOX5 in 293T cells as shown in FIG. 7a. Bone marrow cells from B6 mice are transduced with retrovirus containing IRES-GFP-pMSCV (empty vector) or BCR-ABL-IRES-Alox5-pMSCV, and then transferred into B6 recipient mice to induce CML. The plasma level of LTB4 in recipients of BCR-ABL-IRES-Alox5-pMSCV-transduced bone marrow cells is significantly higher than that in recipients of bone marrow cells transduced with empty vector-containing retrovirus (p<0.01), confirming that the BCR-ABL-IRES-Alox5-pMSCV construct induced LTB4 production in mice as shown in FIG. 7b. In contrast to the lack of CML induction by BCR-ABL in the absence of Alox5, ectopically expressed Alox5 in Alox5$^{-/-}$ bone marrow cells rescue the defective CML phenotype, and all mice receiving the BCR-ABL-IRES-Alox5-pMSCV transduced Alox5$^{-/-}$ bone marrow cells die within 40 days, as shown in FIG. 7c. Control mice that receive BCR-ABL transduced Alox5$^{-/-}$ bone marrow cells all survive.

FACS analysis, and peripheral blood smears show the development of typical CML after the expression of the rescue gene Alox5, consistent with the severe infiltration of myeloid leukemia cells in the lung and spleen as detected histologically (hematoxylin/eosin stained sections). The mice receiving the BCR-ABL-IRES-Alox5-pMSCV transduced wild type bone marrow cells die faster than those receiving the BCR-ABL-IRES-Alox5-pMSCV transduced Alox5$^{-/-}$ bone marrow cells, as shown in FIG. 7c, correlating with more myeloid cells in peripheral blood, and more severe infiltration of myeloid leukemia cells in the lung and spleen. Thus, Alox5 plays a critical role in CML development.

Example 4

Alox5 Deficiency Impairs the Function of LSCs

Figure 8:
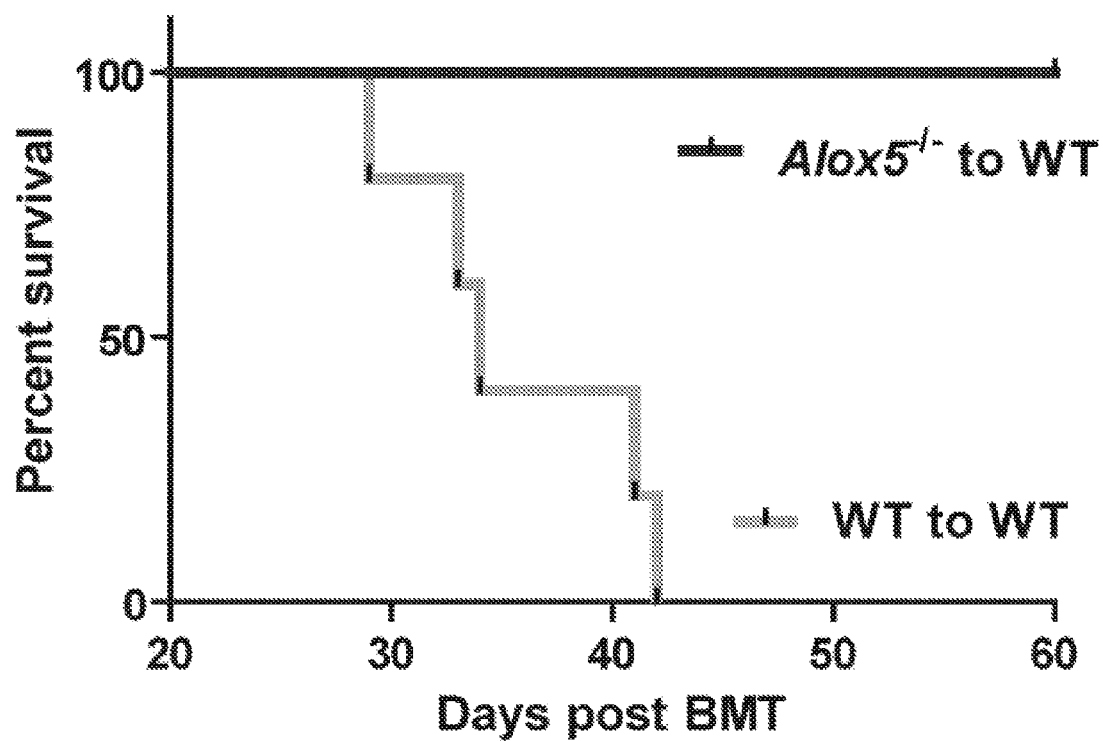
FIG. 8 is a graph showing Kaplan-Meier survival curves and indicating that loss of Alox5 causes failure of BCR-ABL-expressing BM cells to induce CML in secondary recipient mice.

A biological assay for LSCs examines their ability to transfer disease to secondary recipient mice. In this assay, 2×10$^6$ bone marrow cells are transferred from primary recipients of BCR-ABL-transduced wild type (n=5) or Alox5$^{-/-}$ (n=6) donor bone marrow cells to secondary recipient mice. BCR-ABL-expressing wild type bone marrow cells transfers lethal CML, whereas BCR-ABL-expressing Alox5$^{-/-}$ bone marrow cells fail to induce CML in secondary recipient mice as shown in the Kaplan-Meier survival curves in FIG. 8. Thus, Alox5 deficiency causes the impairment of the function of LSCs.

Figure 9:
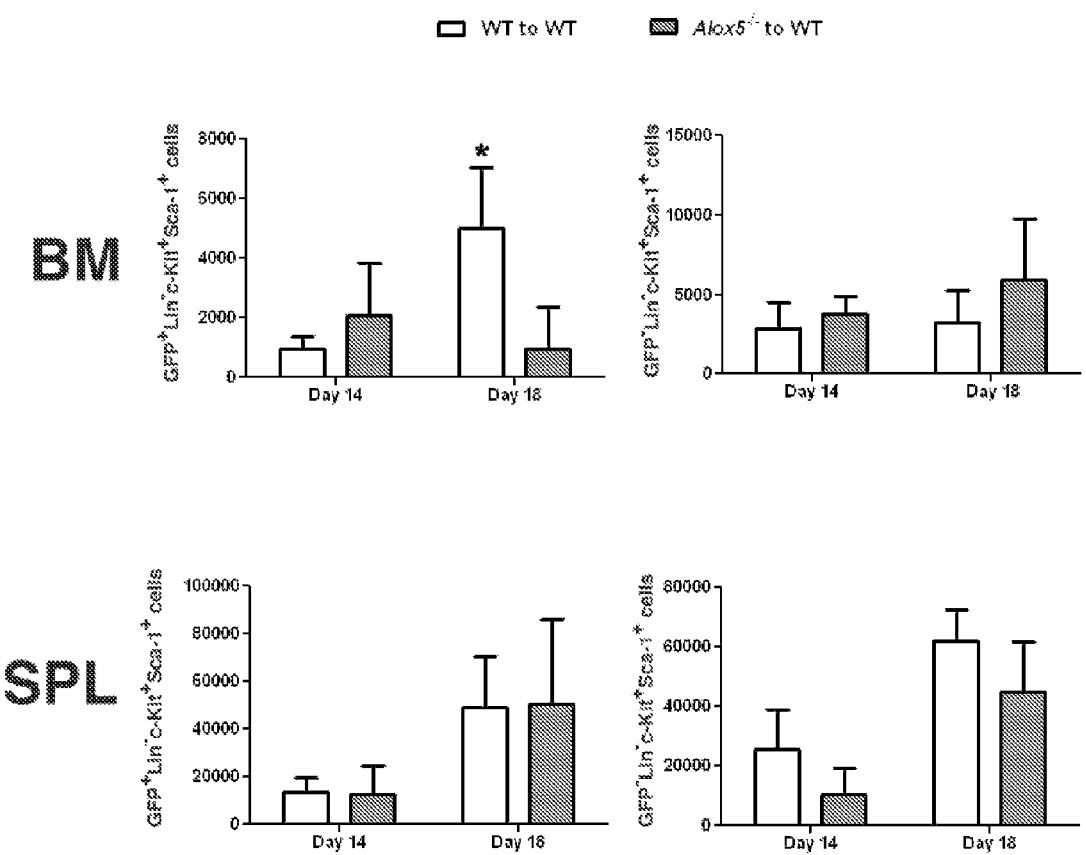
FIG. 9 is a set of graphs showing that loss of Alox5 causes significant reduction of LSCs (Lin$^-$, C-kit$^+$, Sca1$^+$ cells) in bone marrow (BM) at day 18 after induction of CML.

Quantification of LSCs (GFP$^+$Lin$^-$c-Kit$^+$Sca-1$^+$) and normal hematopoietic stem cells (HSCs) (GFP$^-$Lin$^-$c-Kit$^+$Sca-1$^+$) in bone marrow and the spleens of CML mice at day 14 and day 18 after induction of CML by BCR-ABL is performed by FACS analysis using 4 mice in each group at each time point. Total number of Lin$^-$c-Kit$^+$Sca-1$^+$ cells for each mouse is calculated as percentage of Lin$^-$c-Kit$^+$Sca-1$^+$ cells× total cell count for the cells from femurs and tibias. At day 14, Alox5 deficiency did not cause a reduction of LSCs in bone marrow (BM) and spleen (SPL), but did so in bone marrow but not in spleen at day 18, as compared to LSCs in wild type CML mice (p<0.05) as shown in FIG. 9. In the spleen, the number of Alox5$^{-/-}$ LSCs is similar to that of wild type LSCs indicating that the reduction of LSCs in bone marrow is not due to the migration of bone marrow LSCs to the spleens but due to an intrinsic defect caused by Alox5 deficiency in LSCs. Alox5 deficiency does not cause a significant reduction of normal HSCs (GFP$^-$) in bone marrow and the spleens of the same animals, indicating that Alox5 is functionally required by LSCs but not by normal HSCs.

No homing defect of HSCs lacking Alox5 is observed which could cause the impaired CML development when the cells are transduced by BCR-ABL. Furthermore, Alox5 deficiency does not appear to cause a homing defect on LSCs, as the total number of Alox5$^{-/-}$ LSCs is not lower than that of wild type LSCs at day 14 after induction of CML, shown in FIG. 9.

LSCs are sorted by FACS from bone marrow of CML induced by transplanting BCR-ABL-transduced wild type (CD45.1) or Alox5$^{-/-}$ (CD45.2) donor bone marrow cells. Wild type and Alox5$^{-/-}$ LSCs are 1:1 mixed, followed by transplantation into lethally irradiated recipient mice. At day 14 or 25 after transplantation, more than 70% or 90% of GFP$^+$Gr-1$^+$ cells in peripheral blood of the mice are wild type (CD45.1+) leukemia cells, and all these mice developed CML and died within 45 days of bone marrow transplantation.

Figure 10A:
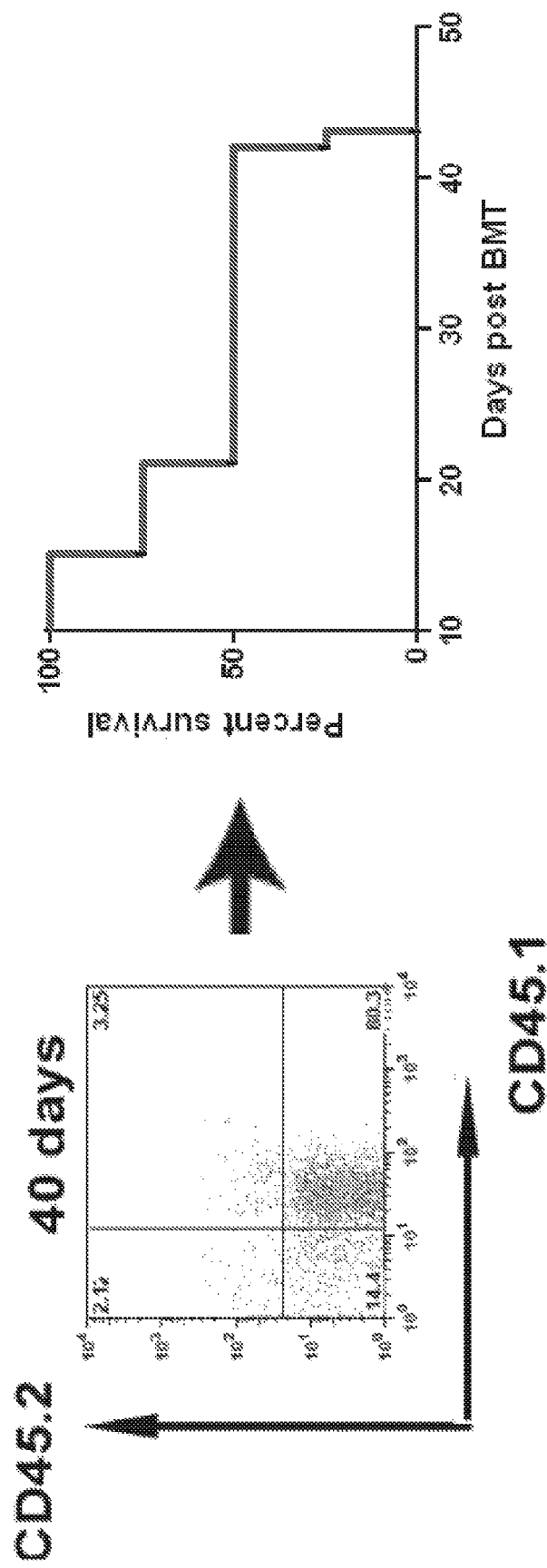
FIG. 10A is a set of graphs showing that 1:1 mixed wild type (CD45.1+) and Alox5-/- (CD45.2+) bone marrow cells transplanted into lethally irradiated recipient mice result in more than 80% of cells in PB are wild type (CD45.1+) leukemia cells 40 days after bone marrow transfer (BMT) and that all mice die of CML as shown in the Kaplan-Meier survival graph.

Total wild type and Alox5$^{-/-}$ bone marrow cells are also 1:1 mixed (5×10$^5$ cells each), followed by transplantation into lethally irradiated recipient mice. At day 40 after BMT, more than 80% of GFP$^+$Gr-1$^+$ cells in peripheral blood are wild type (CD45.1+) leukemia cells as detected by FACS analysis (FIG. 10A), and all these mice died of CML within 45 days, as shown in the Kaplan-Meier curve in FIG. 10A.

Figure 10B:
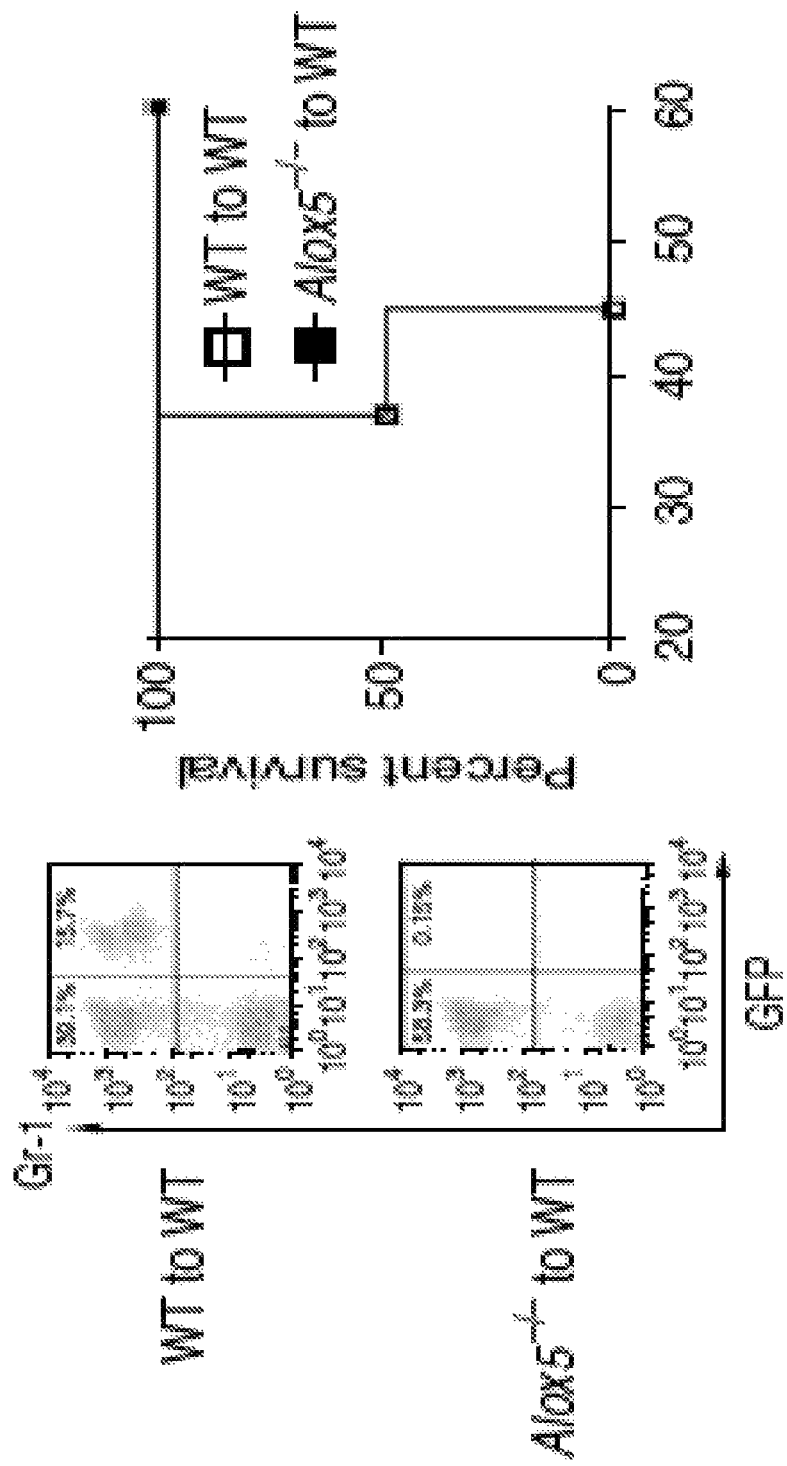
FIG. 10B shows FACS data and a Kaplan-Meier survival graph indicating that mice receiving the Alox5-deficient GFP$^+$Lin$^-$c-kit$^+$Sca-1$^+$ cells survived whereas the mice receiving the wild-type GFP$^+$Lin$^-$c-kit$^+$Sca-1$^+$ cells died of CML.
Figure 10C:
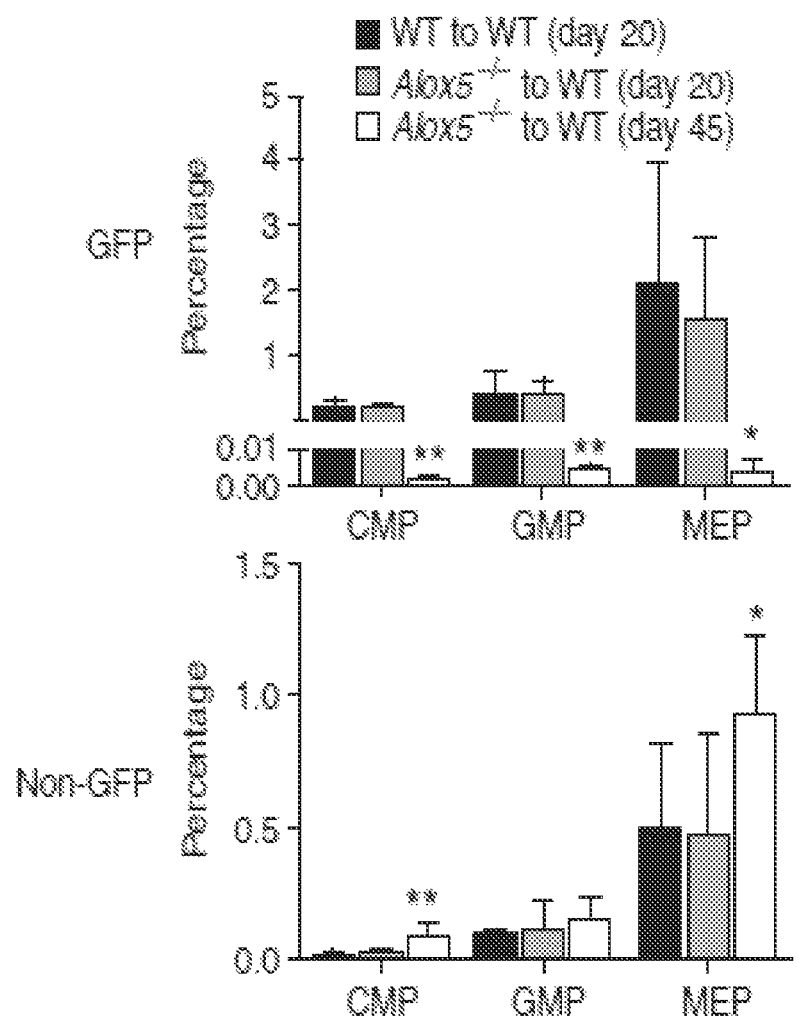
FIG. 10C shows graphs of results of FACS analysis 20 days and 45 days after CML induction indicating the percentages of BCR-ABL-expressing (GFP$^+$) and non-BCR-ABL-expressing (NON-GFP) CMP (common myeloid progenitor), GMP (granulocyte-macrophage progenitor) and MEP (megakaryocyte-erythroid progenitor) cells in BM of recipients of BCR-ABL-transduced wild-type or Alox5$^{-/-}$ donor BM cells (n=4), mean value (±s.d.) for each group is shown, *P<0.05, **P<0.01.

Wild type and Alox5$^{-/-}$ LSCs, BCR-ABL-transduced wild type or Alox5$^{-/-}$ bone marrow cells are sorted by FACS for Lin$^-$c-Kit$^+$Sca-1$^+$ cells, and equal numbers of the sorted wild type and Alox5$^{-/-}$ cells (15,000 cells per recipient) are transplanted into each lethally irradiated recipient mouse. At day 14 after bone marrow transplantation, GFP$^+$Gr-1$^+$ cells are detected in peripheral blood of recipient mice receiving BCR-ABL-transduced wild type bone marrow cells but were barely detectable in peripheral blood of mice receiving BCR-ABL-transduced Alox5$^{-/-}$ bone marrow donor cells, determined by FACS analysis. By day 50 after transplantation, all mice receiving BCR-ABL-transduced sorted wild type bone marrow cells died of CML (n=2), whereas all mice receiving sorted Alox5$^{-/-}$ bone marrow cells survived (n=4) as shown in FIG. 10B. These results indicate that Alox5 deficiency causes impairment of the function of LSCs, consequently leading to reduced production of leukemia progenitor cells. This conclusion is consistent with the finding shown in FIG. 10C that at day 20 after induction of CML by BCR-ABL, similar numbers of GFP$^+$ CMP (common myeloid progenitor), GMP (granulocyte-macrophage progenitor), and MEP (megakaryocyte-erythroid progenitor) cells are detected in bone marrow of mice receiving BCR-ABL-transduced Alox5$^{-/-}$ donor bone marrow cells, as determined by FACS analysis. However, at day 45 these cells are much less in bone marrow of mice receiving BCR-ABL transduced Alox5$^{-/-}$ donor marrow cells. By contrast, Alox5$^{-/-}$ deficiency does not cause reduction of non-BCR-ABL-expressing myeloid progenitor cells in the same animals providing an indirect evidence that Alox5$^{-/-}$ deficiency only causes a functional defect in LSCs but not normal HSCs.

This conclusion is further confirmed by comparing the engraftment of wild type (CD45.1) and Alox5$^{-/-}$ (CD45.2) bone marrow cells by injection of the same number of each type of bone marrow cells into lethally irradiated recipient mice. At 30 days after BMT, the percentage of wild type or Alox5$^{-/-}$ bone marrow cells is similar. A control experiment shows that after lethal irradiation, 100% of cells in peripheral blood of recipient mice are donor-derived when assayed at day 30 after BMT, allowing the direct analysis of CD45.1 or CD45.2 cells to reflect the donor-derived wild type (CD45.1) and Alox5$^{-/-}$ (CD45.2) bone marrow cells in the same animal.

Example 5

Alox5 Deficiency Blocks Differentiation of Long-Term Leukemia Stem Cells

Cell populations affected by Alox5 deficiency are determined using FACS analysis. BCR-ABL-transduced Alox5$^{-/-}$ bone marrow cells are transplanted into recipient mice (n=4) to induce CML, and bone marrow cells from these mice are analyzed by FACS for percentages of total HSCs (Lin$^-$c-Kit$^+$Sca-1$^+$), LT-HSCs (Lin$^-$c-Kit$^+$Sca-1$^+$CD34$^-$), and ST-HSCs/MPP cells (Lin$^-$c-Kit$^+$Sca-1$^+$CD34$^+$).

At day 20 after induction of CML, the percentage or total number of bone marrow LT-LSCs (GFP$^+$Lin$^-$c-Kit$^+$Sca-1$^+$CD34$^-$) is about half of those of ST-LSCs/MPP cells (GFP$^+$Lin$^-$c-Kit$^+$Sca-1$^+$CD34$^+$), as determined by FACS analysis.

At day 90, the percentage or total number of LT-LSCs is about 8-fold higher than that of ST-LSCs/MPP cells, as determined by FACS analysis.

Figure 11:
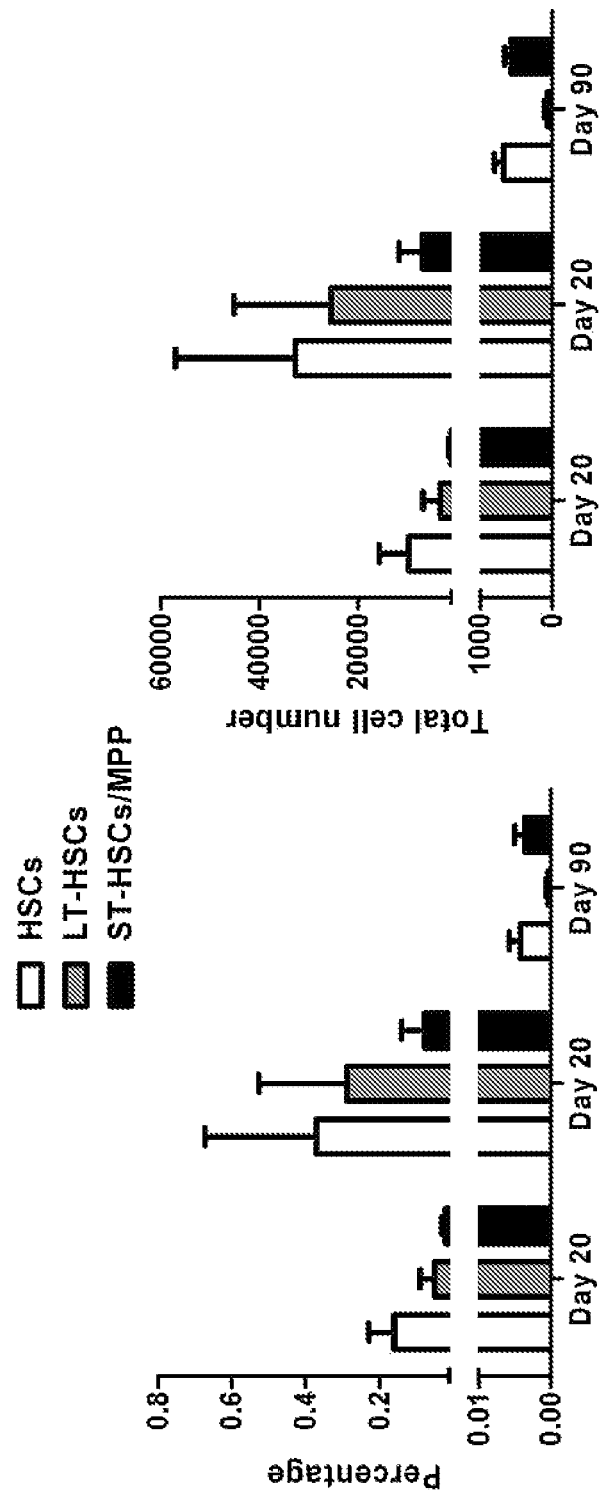
FIG. 11 is a set of graphs showing percentages and total numbers of HSCs (hematopoietic stem cells), LT (long-term)-HSCs (GFP$^-$Lin$^-$c-Kit$^+$Sca-1$^+$CD34$^-$) and ST (short-term)-HSCs/MPP (multipotent progenitor) (GFP$^-$Lin$^-$c-Kit$^+$Sca-1$^+$CD34$^+$) cells at day 20 and 90 after induction of CML where bone marrow cells are isolated from recipients of BCR-ABL transduced bone marrow cells from wild type or Alox5-/- donor mice, and GFP-cell population (representing normal hematopoietic cells in CML mice) are analyzed by FACS analysis.

These results indicate that Alox5 deficiency blocks differentiation of LT-LSCs, preventing these cells from developing CML. In these mice, the percentage of GFP-LT-HSCs (GFP$^-$Lin$^-$c-Kit$^+$Sca-1$^+$CD34$^-$) is lower than that of GFP-ST-HSCs/MPP cells, determined by FACS analysis at day 20 and 90 after CML induction as shown in FIG. 11, demonstrating that Alox5 deficiency does not lead to differentiation blockade of normal LT-HSCs. Although the differentiation of LT-LSCs is blocked in the absence of Alox5 to cause a relative higher percentage of LT-LSCs compared to ST-LSCs/MPP (GFP$^-$Lin$^-$c-Kit$^+$Sca-1$^+$CD34$^+$) cells, the total number of LT- LSCs declined with time, indicating that Alox5 deficiency causes a gradual depletion of LSCs.

Figure 12:
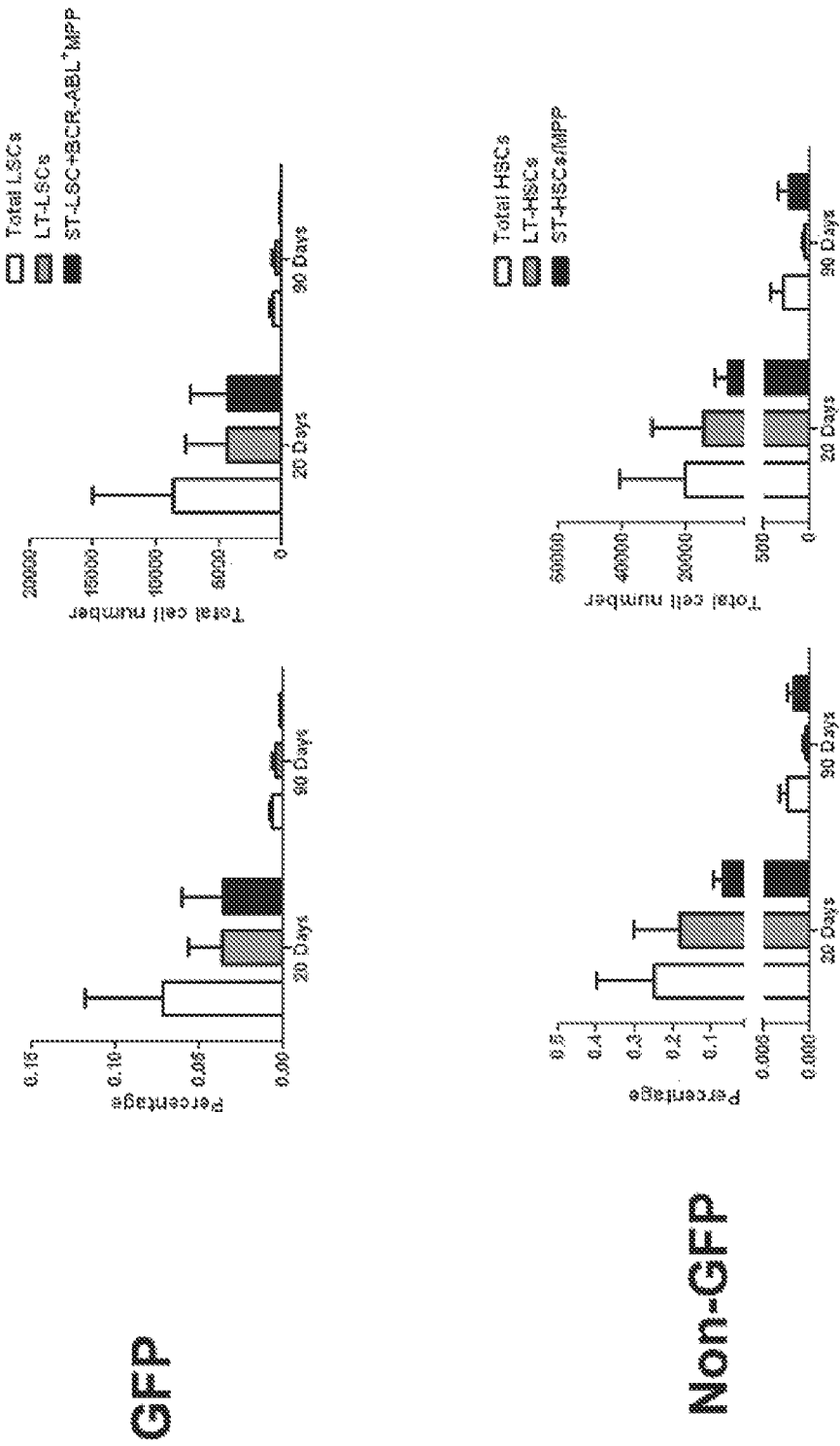
FIG. 12 is a set of graphs showing percentages and numbers of total LSCs, LT-LSCs and ST-LSC+BCR-ABL+MPP cells at day 20 and 90 after induction of CML and treatment with zileuton.
Figure 13:
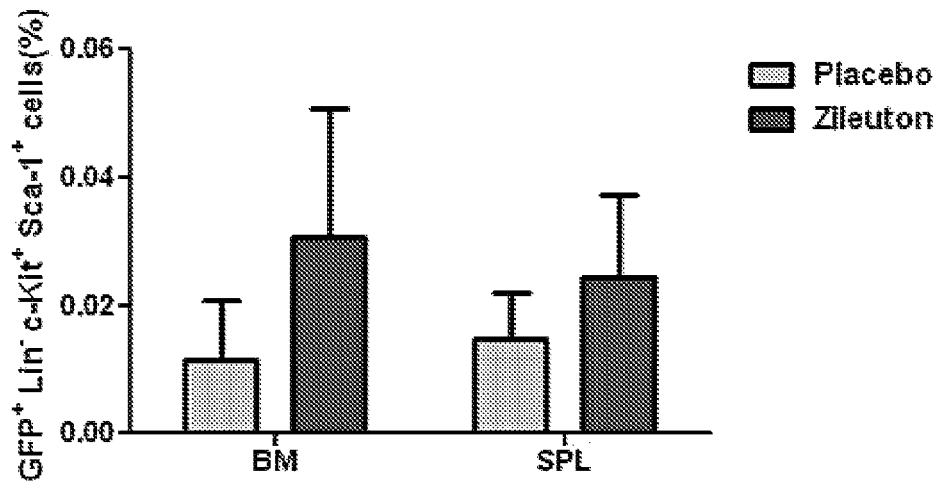
FIG. 13 is a graph showing percentages of normal HSC (GFP$^+$Lin$^-$c-Kit$^+$Sca-1$^+$) cells in bone marrow (BM) and spleen (SPL) of placebo (grey box)- and zileuton (black box)-treated mice.

Recipients of BCR-ABL-transduced wild type bone marrow cells are treated with zileuton (300 mg/kg of body weight, twice a day) beginning at 8 days after BMT. Zileuton is dissolved in water and administered orally in a volume of less than 0.3 ml by gavage. At days 20 and 90 post BMT (induction of CML), FACS analysis is performed. The ratio of percentage of LT-LSCs to percentage of ST-LSCs/MPP cells increased with treatment as shown in FIG. 12, indicating that a blockade of differentiation of LT-LSCs. Zileuton treatment did not lead to blocked differentiation of GFP⁻ LT-HSCs in the same animals indicating that inhibition of ALOX5 does not suppress normal HSCs. No suppression of normal HSCs is found in placebo- or zileuton-treated mice receiving wild type donor bone marrow cells transduced with MSCV-IRES-GFP retrovirus. At day 14 after BMT, the numbers of GFP⁺Lin⁻c-Kit⁺Sca-1⁺ cells in bone marrow of placebo- and zileuton-treated mice indicate that zileuton treatment does not result in a reduction of GFP⁺Lin⁻c-Kit⁺Sca-1⁺ cells in bone marrow (BM) or the spleens (SPL) of the mice as shown in FIG. 13.

The blockade of LT-LSC differentiation is correlated with biological and molecular changes in LSCs. Cell cycle analysis of LSCs in bone marrow of CML mice showed that there is a higher percentage of LT-LSCs in the S+G2M phase of the cell cycle in mice receiving BCR-ABL-transduced Alox5$^{-/-}$ bone marrow cells than in mice receiving BCR-ABL-transduced wild type bone marrow cells, and the percentages of LT-LSCs and ST-LSCs/MPPs in the S+G2M phase of the cell cycle are similar. The bone marrow is isolated 14 days after BMT from wild type or Alox5$^{-/-}$ donor mice. The cells are stained with Hoechst Blue, and DNA content, analyzed by the percentages of three LSC populations (total LSCs, LT-LSCs, and ST-LSCs+MPPs) in the S+G2M phase of the cell cycle, is determined by FACS. The findings indicate that the differentiation blockade causes a compensatory response of Alox5-deficient LSCs to the shortage of downstream cell lineages. The higher percentage of LT-LSCs in the S+G2M phase of the cell cycle in the absence of Alox5 may also be explained by asymmetric cell division of LT-LSCs.

Figure 14A:
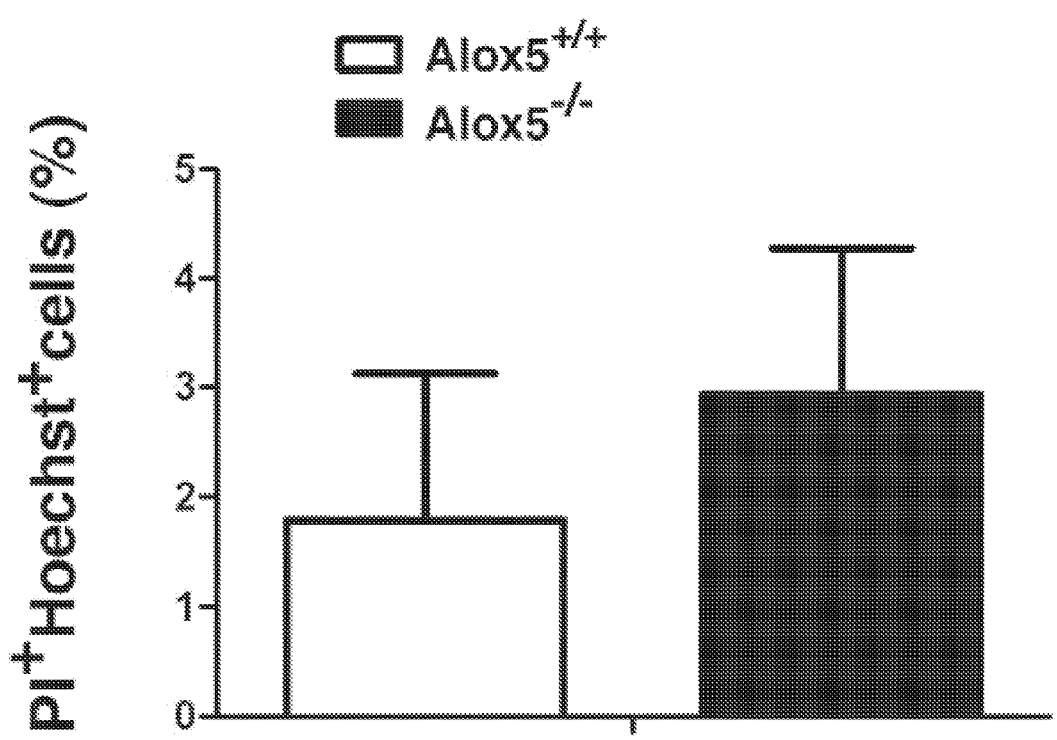
FIG. 14A is a graph showing percentages of propidium iodide (PI) and Hoechst Blue positive bone marrow cells isolated 14 days after BMT from wild type (Alox5$^{+/+}$) or Alox5$^{-/-}$ donor mice.
Figure 14B:
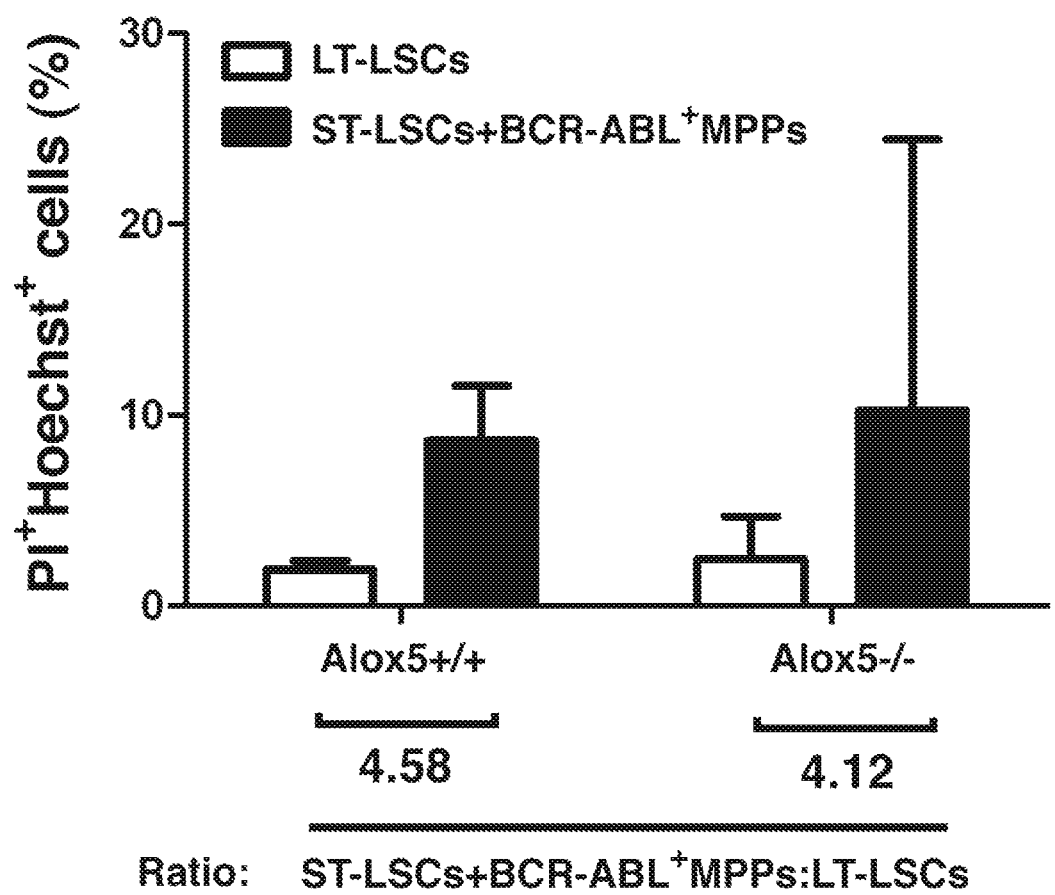
FIG. 14B is a graph showing percentages of propidium iodide (PI) and Hoechst Blue positive bone marrow cells isolated 14 days after BMT isolated 14 days after BMT from wild type (Alox5$^{+/+}$) or Alox5$^{-/-}$ donor mice, where the PI+Hoechst+ cells are further analyzed by FACS for the presence of LT-LSCs (GFP$^+$Lin$^-$c-Kit$^+$Sca-1$^+$CD34$^-$) and ST-LSCs/BCR-ABL-expressing MPP (Lin$^-$c-Kit$^+$Sca-1$^+$CD34$^+$) cells and where the ratios between ST-LSCs/BCR-ABL-expressing MPP cells and LT-LSCs in the presence and absence of Alox5 are compared.

Alox5 deficiency causes apoptosis of LSCs (P>0.05), as determined by propidium iodide staining and FACS sorting and shown in FIG. 14A and the apoptotic ratio between Alox5$^{-/-}$ ST-LSCs/MPPs and LT-LSCs is similar to the ratio between Alox5$^{+/+}$ST-LSCs/MPPs and LT-LSCs, shown in FIG. 14B. Together, these results indicate that the proportional increase in LT-LSCs in the absence of Alox5 is not caused by asymmetric division or apoptosis of ST-LSCs/MPPs and LT-LSCs.

The expression levels of three regulatory genes of hematopoiesis, β-catenin, GATA-1 and FOG-1 are determined by Real Time RT-PCR. β-actin expression is used for normalization. Total RNA is isolated from bone marrow GFP⁺Lin⁻c-Kit⁺Sca-1⁺ cells (BMC) of recipients of GFP vector- or BCR-ABL-transduced bone marrow cells from wild type (WT) or Alox5$^{-/-}$ donor mice. cDNA is synthesized using the Ovation-Pico cDNA synthesis method.

Primers Used for the RT-PCR are:

```
β-catenin: forward primer:
                                SEQ ID No. 3
5'-AACAGGGTGCTATTCCACGACTA-3'

β-catenin: reverse primer
                                SEQ ID No. 4
5'-TGTGAACGTCCCGAGCAA-3'.

GATA-1 forward primer
                                SEQ ID No. 5
5'-ACTGTGGAGCAACGGCTACT-3'.

GATA-1 reverse primer
                                SEQ ID No. 6
5'-TCCGCCAGAGTGTTGTAGTG-3'.

FOG-1 forward primer
                                SEQ ID No. 7
5'-CATAGAGGAGCCCCCAAGTC-3'.

FOG-1 reverse primer
                                SEQ ID No. 8
5'-GGCTGCCTCTTCTTCCTTTT-3'.
```

The Power SYBR Green PCR master mix was from Applied Biosystems. The numbers of copies of β-catenin, GATA-1 and FOG-1 mRNA relative to 1,000 copies of β-actin mRNA reflect the abundance of mRNA copies detected.

Figure 15:
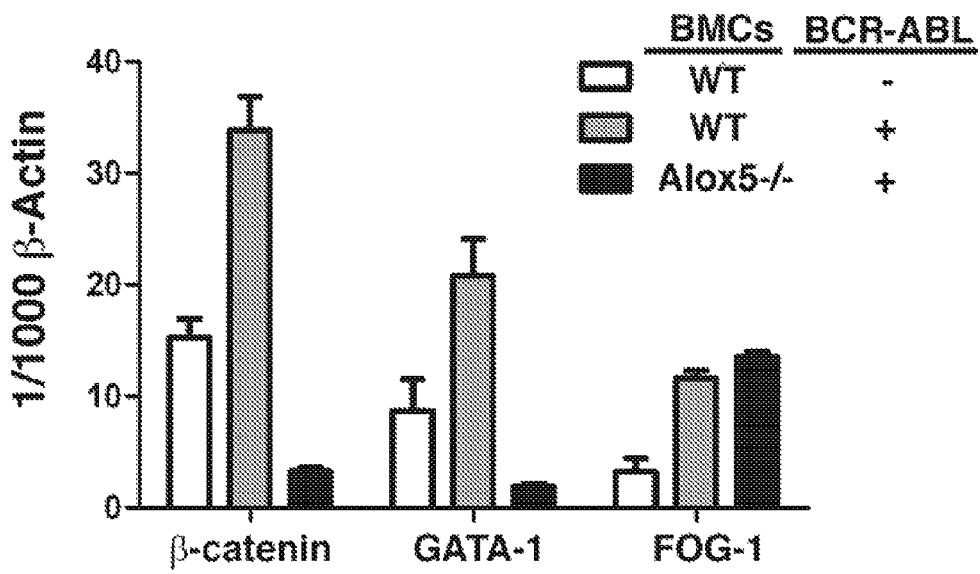
FIG. 15 is a graph showing an RT-PCR analysis of β-catenin, GATA-1 and FOG (triplicate) from bone marrow GFP$^+$Lin$^-$c-Kit$^+$Sca-1$^+$cells (BMC) of recipients of GFP vector- or BCR-ABL-transduced bone marrow cells from wild type (WT) or Alox5$^{-/-}$ donor mice where the expression level is normalized to β-actin.

The analysis is done in triplicate. The expression levels indicate that the defective function of LSCs in the absence of Alox5 correlates with the reduction of β-catenin and GATA-1 but not FOG-1, shown in FIG. 15.

DNA microarray analysis identifies genes differentially expressed in LSCs in the absence of Alox5 with 26 being upregulated (+) and 24 downregulated (−) when compared to Alox5 expressing LSCs, as shown in Table I. These genes are potential targets for a therapy approach to treat leukemia.

TABLE I

Differently regulated genes in LSCs lacking Alox5:

| Gene name | Fold change |
| --- | --- |
| Ctse | 10.84409864 |
| Ccdc112 | 10.83634483 |
| Alg11 | 10.767569 |
| Igh | 10.09521896 |
| Chd7 | 9.634118363 |
| Sycp3 | 9.556718503 |
| Kctd4 | 9.101964467 |
| Gca | 8.845678965 |
| Rag1 | 8.254885715 |
| Car6 | 7.684582563 |
| Nxn | 7.543923266 |
| Tspan5 | 7.52896093 |
| Cspp1 | 7.209182093 |
| Rsad2 | 6.931275182 |
| Gsta4 | 6.782521644 |
| Pou2af1 | 6.714906879 |
| Cr1 | 6.651690789 |
| Cldn13 | 6.607268805 |
| Tcp1 | 6.534293996 |
| Adamts3 | 6.515815905 |
| Wdr32 | 6.469928572 |
| Cd59a | 6.452315418 |
| Hist1h4h | 6.446004648 |
| Zscan29 | 6.343767426 |
| Gstt3 | 6.3222711 |
| Wdr47 | 6.308811055 |
| Atp6v0d2 | −11.32634 |
| Rnf170 | −10.5889 |
| Mmp12 | −9.375065 |
| Rpl23a | −8.9810054 |
| Ear2 | −8.3521562 |
| Pcyt1a | −8.2605178 |
| Lst1 | −7.8245812 |
| Myo9a | −7.8123875 |
| Bcl2l14 | −7.73559 |
| Il18 | −7.5060715 |
| Hdc | −6.889881 |
| Serpinа1b | −6.7851782 |
| Arhgap17 | −6.6973953 |
| Ifit3 | −5.9523489 |

TABLE I-continued

Differently regulated genes in LSCs lacking Alox5:

| Gene name | Fold change |
| --- | --- |
| Rbm41 | −5.8332685 |
| Gna14 | −5.7824768 |
| Mertk | −5.678084 |
| Msr1 | −5.6766115 |
| Depdc7 | −5.5954724 |
| RP23-136K12.4 | −5.4804824 |
| Zc3h12c | −5.2626629 |
| Lsm14b | −5.2458504 |

TABLE I-continued

Differently regulated genes in LSCs lacking Alox5:

| Gene name | Fold change |
| --- | --- |
| Cysltr2 | −5.1915405 |
| Maf | −5.1888613 |

Example 6

Inhibition of 5-LO Prolongs Survival of CML Mice

Figure 16:
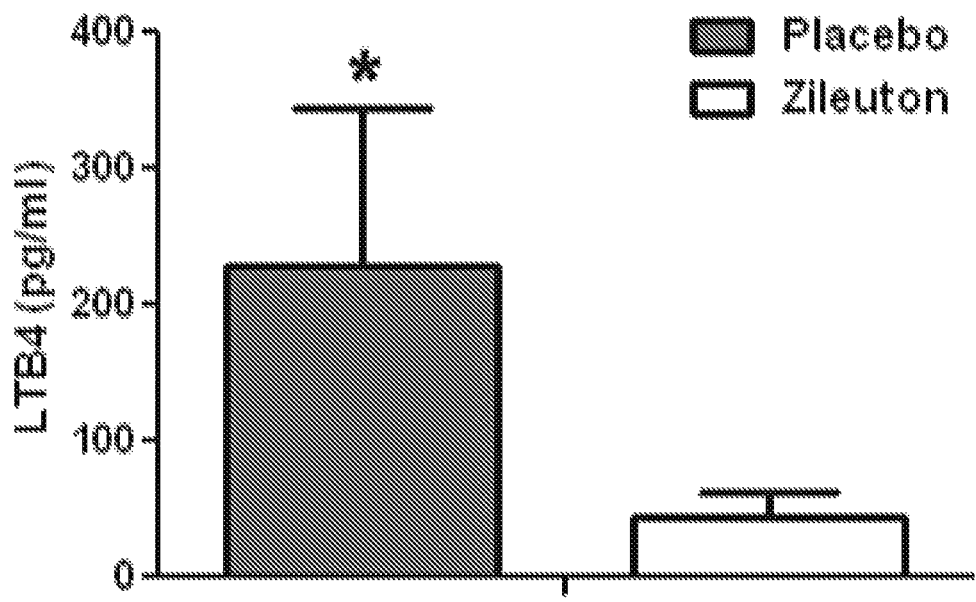
FIG. 16 is a graph showing that zileuton treatment results in a reduction of the plasma LTB4 level in CML mice.
Figure 17:
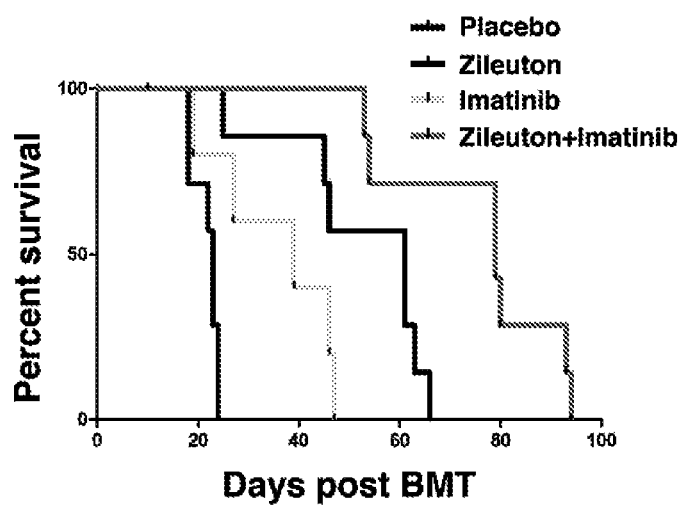
FIG. 17 is a graph showing Kaplan-Meier survival curves for CML mice treated with a placebo, zileuton alone, imatinib alone, or both zileuton and imatinib in combination.

Mice with BCR-ABL-induced CML are treated with a placebo, the ALOX5 inhibitor zileuton, imatinib alone, or the two agents in combination. Zileuton and imatinib are dissolved in water. The drugs are given orally in a volume of less than 0.3 ml by gavage (300 mg/kg, twice a day for zileuton, and 100 mg/kg, twice a day for imatinib) beginning at 8 days after bone marrow transplantation, and continuing until the morbidity or death of the leukemia mice. Water is used as placebo. All placebo-treated mice develop and die of CML within 4 weeks after induction of CML. Zileuton inhibits Alox5 function in CML mice, as plasma level of LTB4 is decreased compared to placebo-treated CML mice, shown in FIG. 16. As expected, imatinib treatment is effective in treating CML, but unexpectedly, zileuton treatment is even more effective, shown in FIG. 17. Treatment of CML mice with both zileuton and imatinib surprisingly has a better therapeutic effect than treatment with either zileuton or imatinib alone in prolonging survival of the mice as shown in Kaplan-Meier survival curves in FIG. 17.

Prolonged survival of zileuton-treated CML mice correlates with less severe leukemia cell infiltration to the lungs and the spleens. In peripheral blood of CML mice treated with zileuton and imatinib, GFP$^+$Gr-1$^+$ leukemia cells gradually decrease with treatment, and drop from over 50% to less than 2%, as analyzed at day 60 after induction of CML. Although these mice eventually die, FACS analysis barely detects any GFP$^+$Gr-1$^+$ myeloid leukemic cells in peripheral blood, indicating that myeloid leukemia is eliminated, FIG. 17B. Instead, these mice developed ALL, as shown by the presence of GFP$^+$B220$^+$ leukemic cells in peripheral blood.

Prolonged survival of zileuton-treated CML mice correlates with less severe leukemia cell infiltration to the lungs and the spleens. In peripheral blood of CML mice treated with zileuton and imatinib, GFP$^+$Gr-1$^+$ leukemia cells gradually decrease with treatment, and drop from over 50% to less than 2%, as analyzed at day 60 after induction of CML. Although these mice eventually die, FACS analysis barely detects any GFP$^+$Gr-1$^+$ myeloid leukemia cells in peripheral blood, indicating that myeloid leukemia is eliminated, (see Table II). Instead, these mice developed ALL, as shown by the presence of GFP$^+$B220$^+$ leukemic cells in peripheral blood.

TABLE II

Percentage of GFP$^+$Gr-1$^+$ myeloid leukemia cells in the peripheral blood of CML mice at various time points after treatment.

| Treatment | Day 11 | Day 14 | Day 21 | Day 28 | Day 35 | Day 42 | Day 60 |
| --- | --- | --- | --- | --- | --- | --- | --- |
| Placebo | 52.6% | 50.1% | | | | | |
| Imatinib | 48.6% | 63.9% | 61.9% | 44.9% | | | |
| Zileuton | 48.3% | 49.9% | 62.9% | 61.4% | 39.7% | 29.4% | 5.1% |
| Imatinib + Zileuton | 58.9% | 53.7% | 59.8% | 41.8% | 35.4% | 6.5% | 1.5% |

Figure 18:
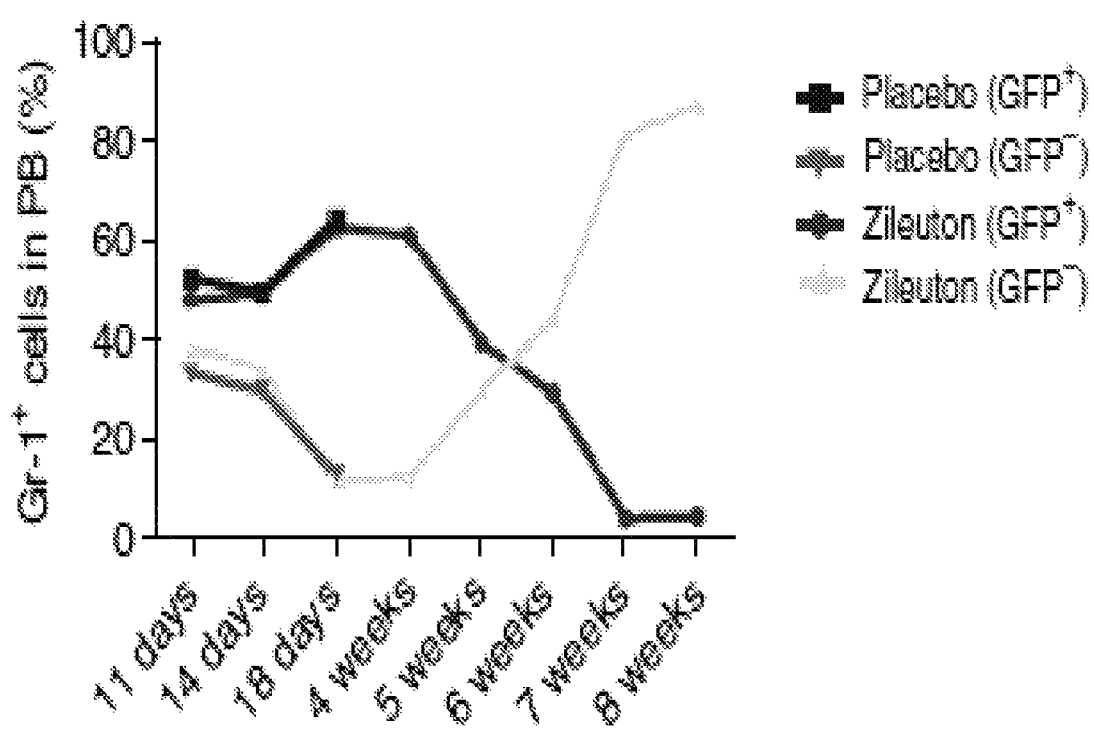
FIG. 18 is a graph showing the percentage of normal myeloid cells (GFP$^-$Gr-1$^+$) and myeloid leukemic cells (GFP$^+$Gr-1$^+$) in CML mice treated with zileuton or placebo from 11 days to 8 weeks and showing that in CML mice treated with zileuton, GFP$^+$Gr-1$^+$ cells in peripheral blood (PB) gradually decrease with time, whereas the GFP$^-$Gr-1$^+$ cells that did not express BCR-ABL gradually increase, indicating that inhibition of Alox5 with zileuton significantly inhibits engraftment of BCR-ABL-expressing but not normal bone marrow (BM) cells in the same animals.

Zileuton treatment does not have an inhibitory effect on normal myeloid cells (GFP$^-$Gr-1$^+$) in peripheral blood of the same animals, as the number of these non-leukemia cells increases during the treatment, but only affects the GFP$^+$Gr-1$^+$ myeloid leukemia cells as shown in Table II and FIG. 18.

In bone marrow of zileuton-treated CML mice, GFP$^+$Gr-1$^+$ myeloid leukemia cells also drop to low levels during the treatment as determined by FACS analysis.

Figure 19:
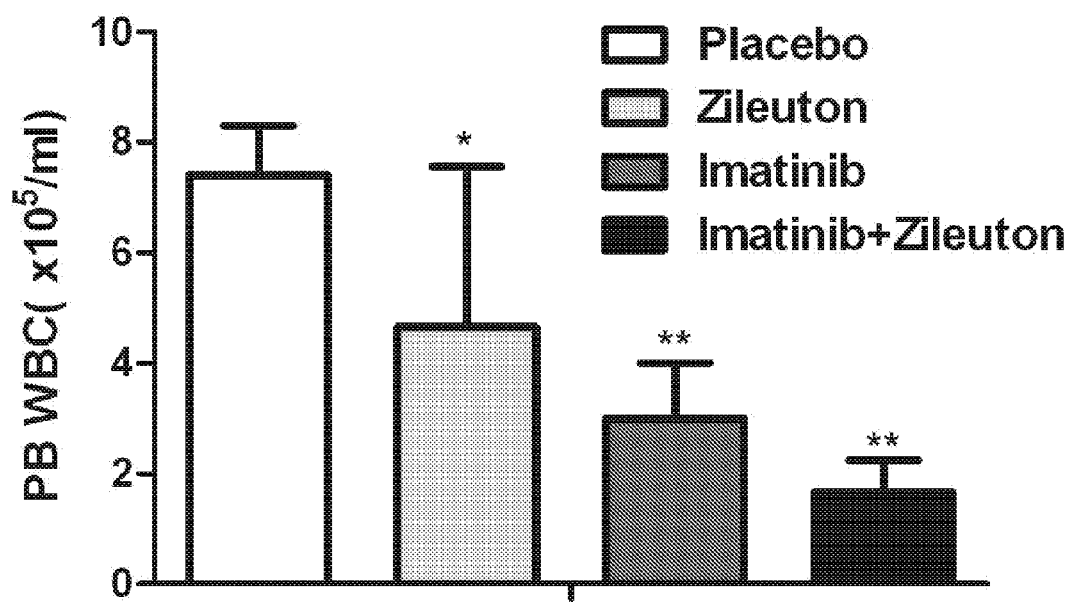
FIG. 19 is a graph showing a comparison of peripheral white blood cell (WBC) counts from CML mice treated with a placebo, zileuton alone, imatinib alone, or both zileuton and imatinib in combination.

Zileuton treatment causes a reduction of white blood cell counts less dramatically than does imatinib treatment, shown in FIG. 19, presumably because zileuton targeted CML-SCs and imatinib inhibits more differentiated leukemic cells. The white blood cells are collected from the CML induced mice 14 days after bone marrow transplantation.

Figure 20:
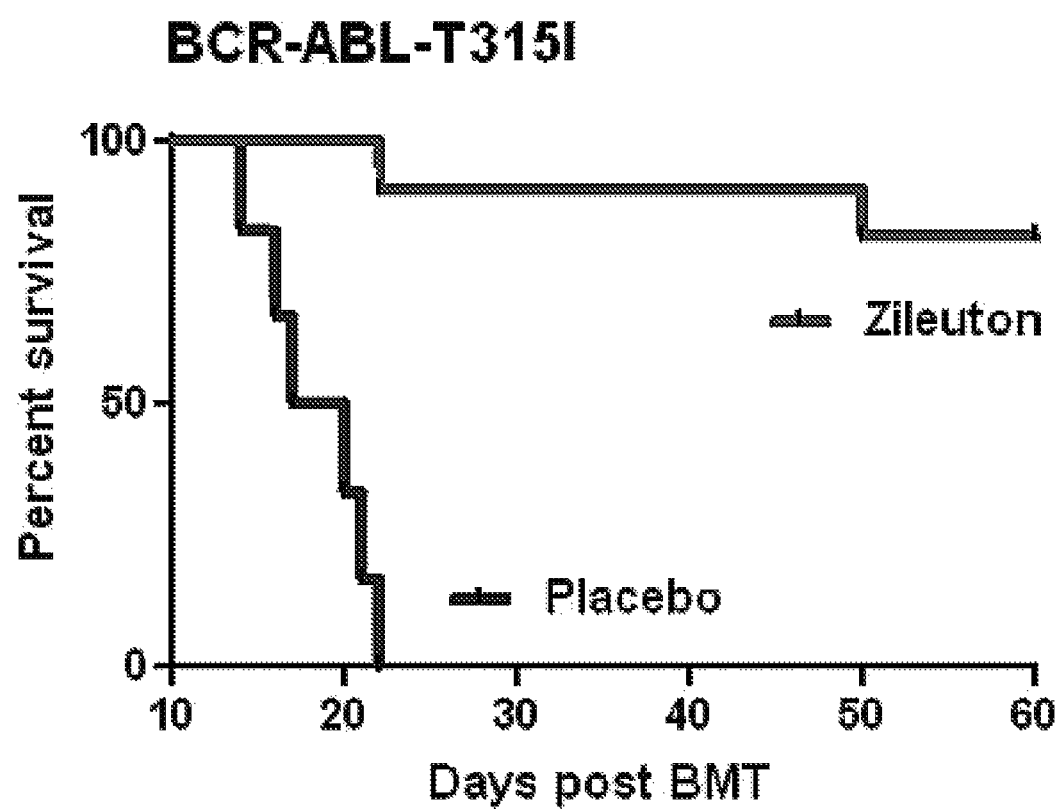
FIG. 20 is a graph showing Kaplan-Meier survival curves for CML mice with the T315I mutation treated with a placebo (n=6) or zileuton (n=11)

Zileuton treatment also prolongs survival of mice with CML induced by BCR-ABL-T315I as shown in FIG. 20.

No increase of plasma LTC4 levels is observed in mice receiving BCR-ABL-expressing wild type bone marrow cells (BCR-ABL+Alox5$^{+/+}$) as compared to mice receiving BCR-ABL-expressing Alox5-deficient bone marrow cells (BCR-ABL+Alox5$^{-/-}$). The mean level of LTC4 is 128.63 pg/ml for the BCR-ABL+Alox5$^{+/+}$ group and 154.84 pg/ml for the BCR-ABL+Alox5$^{-/-}$ group, respectively.

Example 7

Alox5 Deficiency does not Significantly Affect Normal HSCs

Figure 21:
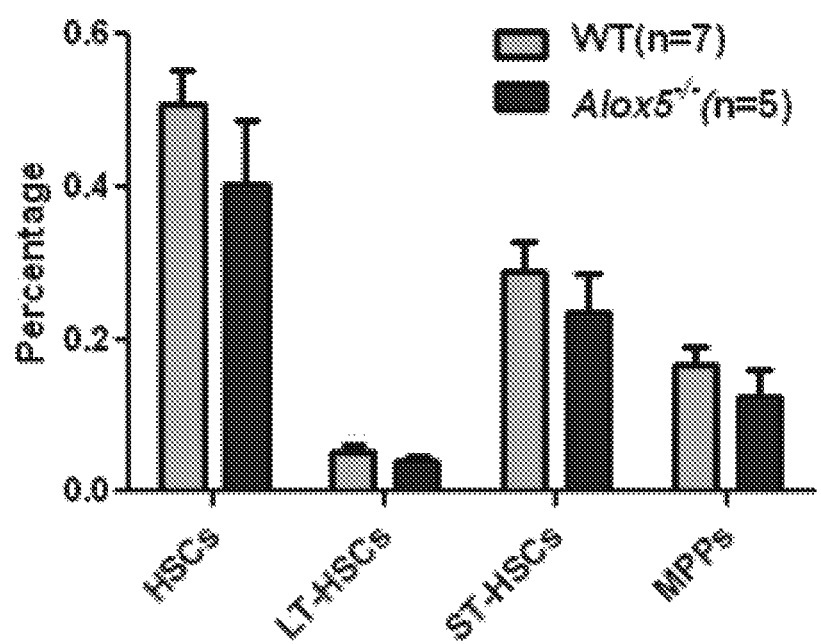
FIG. 21 is a set of graphs showing percentages of bone marrow cells from wild type and Alox5−/− mice analyzed by FACS for the percentages of total HSCs (Lin$^-$c-Kit$^+$Sca-1$^+$), LT-HSCs (Lin$^-$c-Kit$^+$Sca-1$^+$CD34$^-$), ST-HSCs (Lin$^-$c-Kit$^+$Sca-1$^+$CD34$^+$Flt3$^-$), and MPPs (Lin$^-$c-Kit$^+$Sca-1$^+$CD34$^+$Flt3$^+$)
Figure 22:
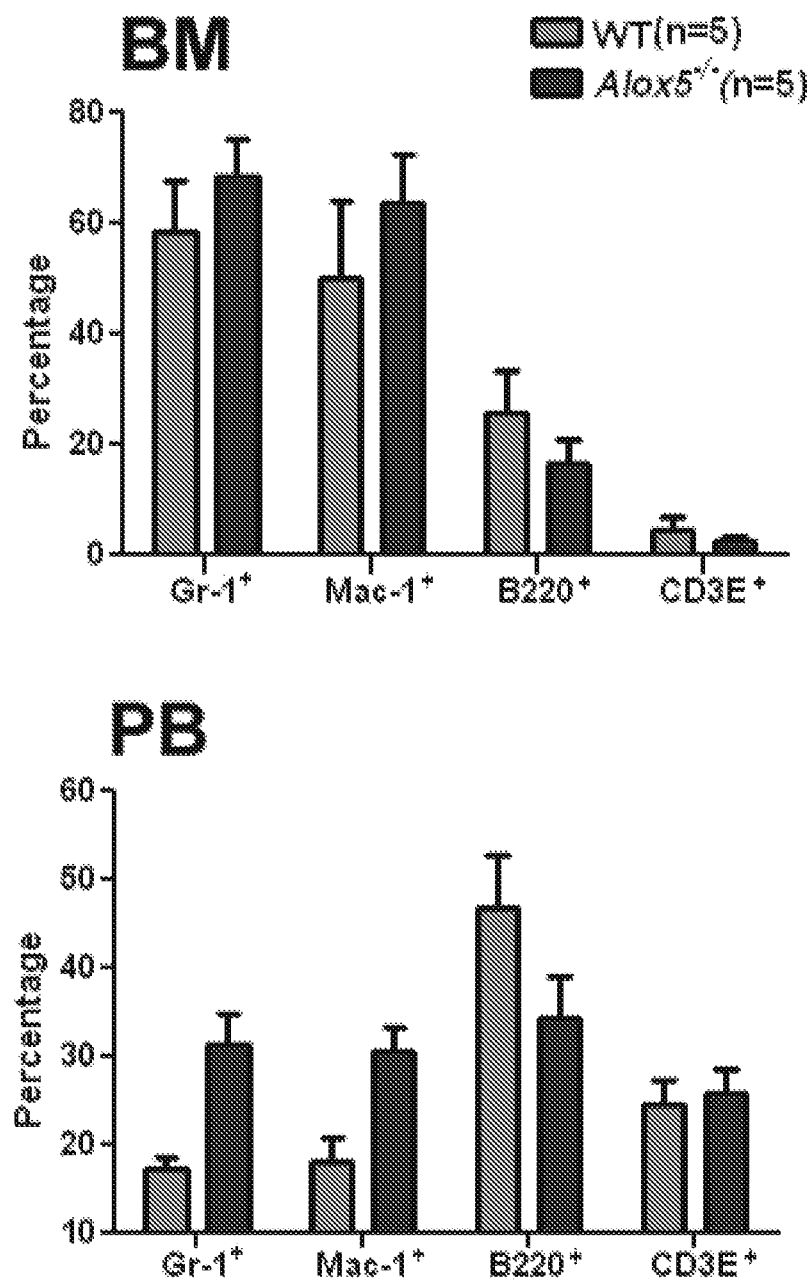
FIG. 22 is a set of graphs showing percentages of cells from bone marrow (BM) and peripheral blood (PB) of wild type and Alox5$^{-/-}$ mice analyzed by FACS for the percentages of Gr-1$^+$, Mac-1$^+$, B220$^+$, and CD3E$^+$ cells.

Hematopoietic cell lineages in bone marrow and peripheral blood of Alox5$^{-/-}$ mice are compared with those of wild type B6 mice. The percentages of HSCs (Lin$^-$c-Kit$^+$Sca-1$^+$), LT-HSCs (Lin$^-$c-Kit$^+$Sca-1$^+$CD34$^-$), ST-HSCs (Lin$^-$c-Kit$^+$Sca-1$^+$CD34$^+$Flt3$^-$) and MPPs (Lin$^-$c-Kit$^+$Sca-1$^+$CD34$^+$Flt3$^+$) in bone marrow of Alox5$^{-/-}$ mice are slightly lower than those of wild type mice as shown in FIG. 21, and the percentages of Gr-1$^+$, Mac-1$^+$, B220$^+$, or CD3E$^+$ cell populations in bone marrow of these mice are similar to those of wild type mice as shown in FIG. 22. In peripheral blood, the numbers of Gr-1$^+$ and Mac-1$^+$ cells in Alox5$^{-/-}$ mice are even higher than those in wild type mice, shown in FIG. 22. Thus, Alox5 deficiency does not lead to significant decrease in the numbers of hematopoietic cell lineages.

Figure 23A:
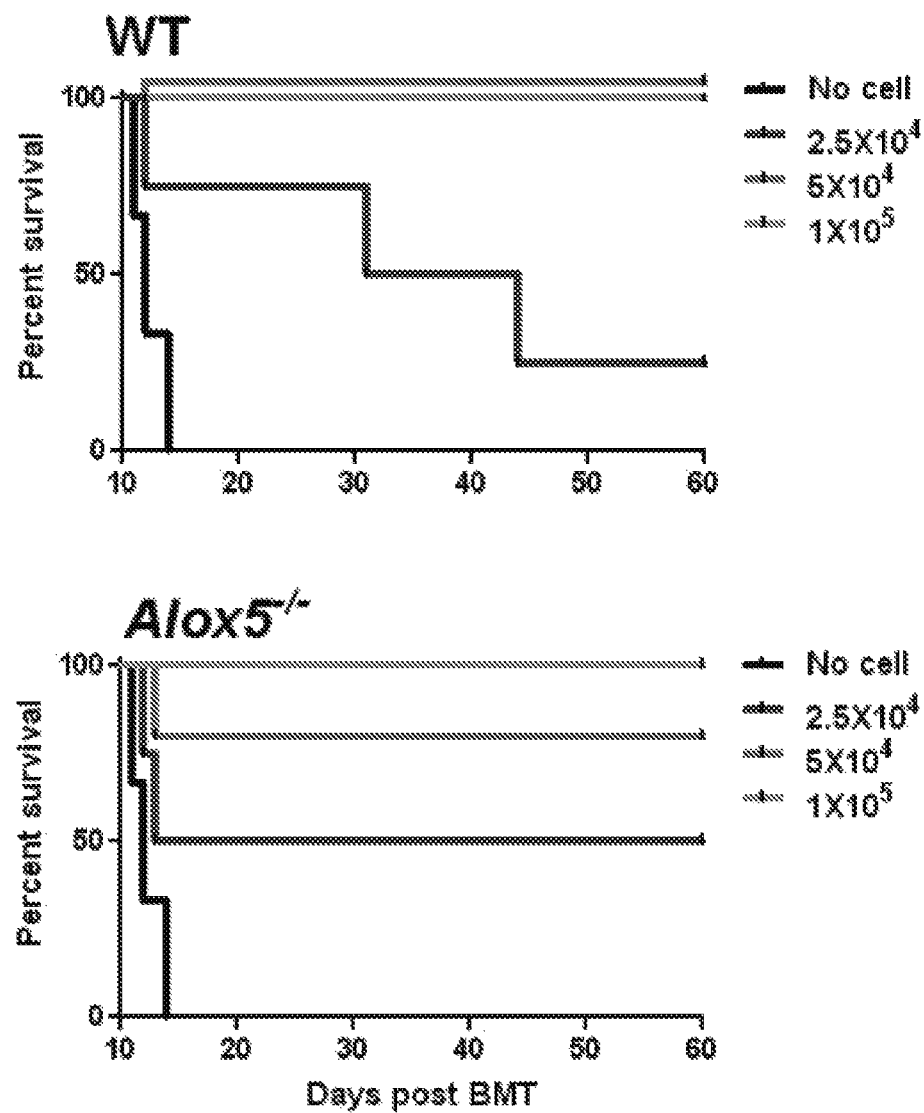
FIG. 23A is a set of graphs showing Kaplan-Meier survival curves of lethally irradiated recipient mice injected with 0 (no cell), 1×10$^5$, 5×10$^4$, and 2.5×10$^4$ of wild type (WT) or Alox5$^{-/-}$ BM cells.

The functional capacities of HSCs in Alox5$^{-/-}$ and wild type mice are compared using an engraftment assay, in which several doses of Alox5$^{-/-}$ or wild type bone marrow cells are transplanted into lethally irradiated wild type B6 mice. The engraftment ability of Alox5$^{-/-}$ bone marrow cells is slightly lower than that of wild type bone marrow cells, as 5×10$^4$ wild type bone marrow cells completely protected lethally irradiated recipient mice, whereas the same number of Alox5$^{-/-}$ bone marrow cells partially rescued the irradiated mice, shown in FIG. 23A.

Figure 23B:
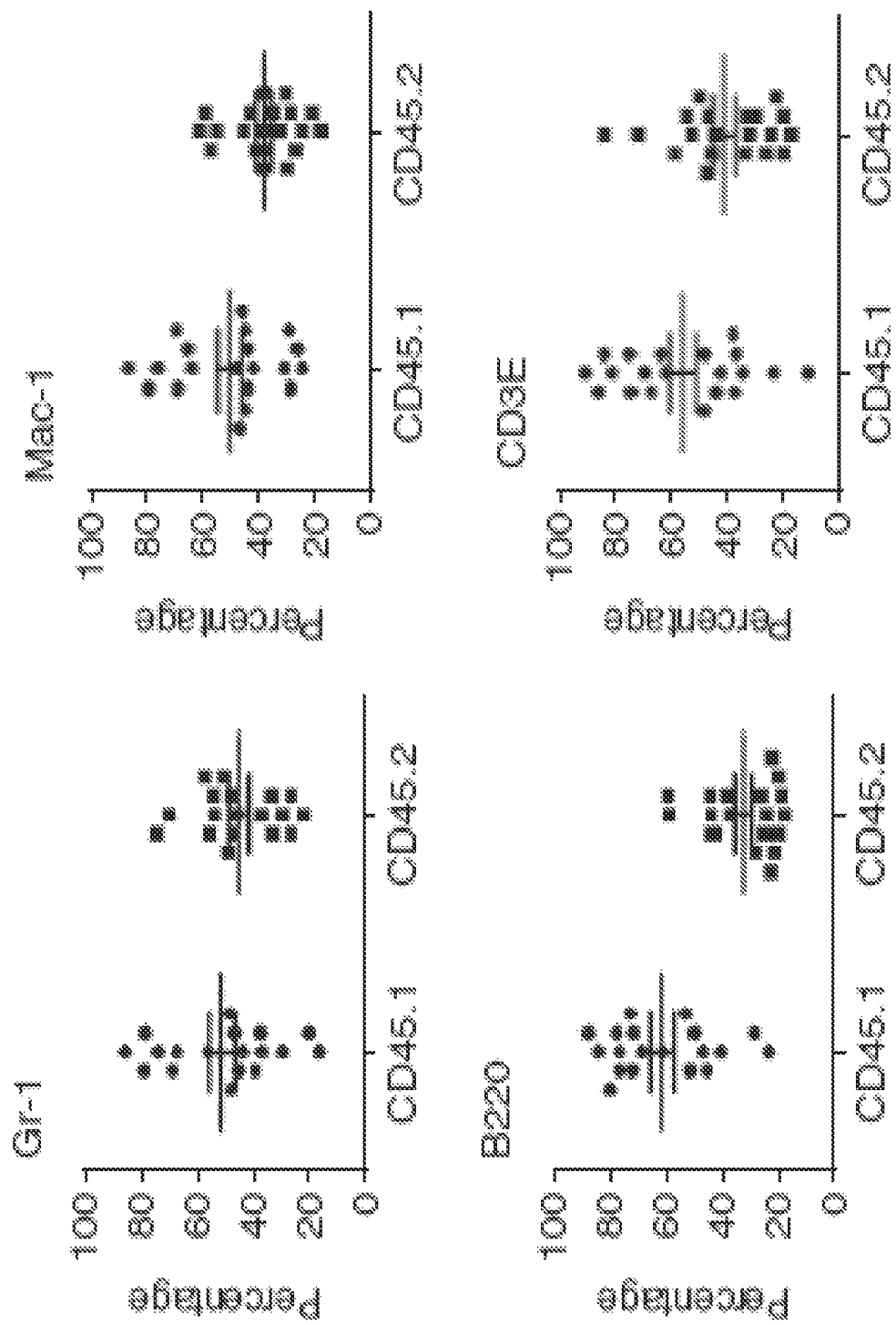
FIG. 23B shows results of FACS analysis illustrating the percentages of wild-type and Alox5$^{-/-}$Gr-1$^+$, Mac-1$^+$, B220$^+$ and CD3E$^+$ cells in peripheral blood of recipient mice.

A competitive reconstitution analysis is performed, in which Alox5$^{-/-}$ (CD45.2) and wild-type (CD45.1) bone marrow cells are mixed 1:1 and then transferred into recipient mice. FACS analysis 12 weeks after transplantation, shows that the percentages of CD45.2 Gr-1$^+$ and Mac-1+ cells are slightly lower than those of CD45.1 Gr-1$^+$ and Mac-1$^+$ cells in peripheral blood, indicating that Alox5$^{-/-}$ HSCs have slightly lower stem cell function as compared to wild type HSCs. However, the effect of Alox5 deficiency on normal HSCs is much less than that on LSCs, as the competitive engraftment capability of the sorted Alox5$^{-/-}$ LSCs is about 30-fold lower than that of wild-type LSCs as assayed at day 25 after CML induction, see FIG. 10B, comparing to the one fold difference between Alox5$^{-/-}$ and normal HSCs, FIG. 23B. This is further supported by the observation that Alox5$^{-/-}$ LSCs fail to induce CML see FIG. 10B.

Figure 24:
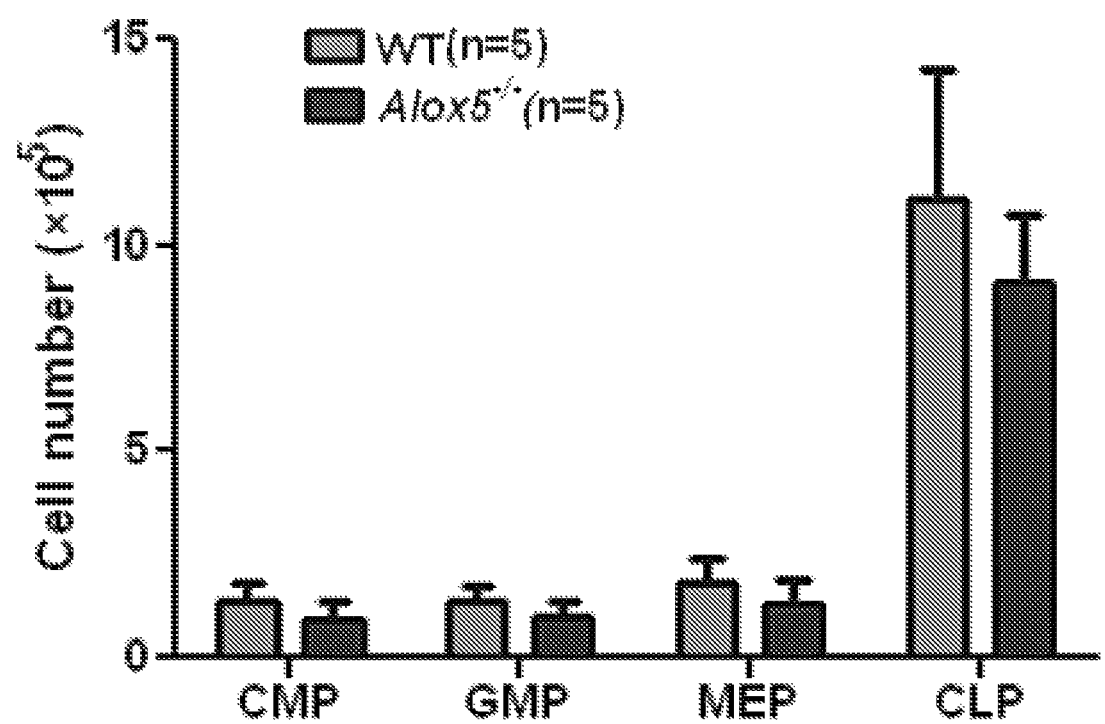
FIG. 24 is a graph showing BM cells of wild type (WT, grey box) and Alox5$^{-/-}$ (black box) mice were analyzed by FACS for the numbers of CMPs, GMPs, MEP, and CLPs (common lymphoid progenitor)

The numbers of bone marrow CMP, GMP, MEP, and CLP is compared between wild type and Alox5$^{-/-}$ mice, and no significant differences are found, as shown in FIG. 24, indicating that there are no significant functional defects in these progenitor cells.

Examination of cell cycle and gene expression of β-catenin, GATA-1 and FOG-1 (for RT-PCR see description in Example 6) in Alox5$^{-/-}$ HSCs shows that there are slightly higher percentages of both LT-HSCs and ST-HSCs/MPPs in the S+G2M phase of the cell cycle in Alox5$^{-/-}$ bone marrow cells than in wild type bone marrow cells, in contrast to the only increase in LT-LSCs in S+G2M phase of the cell cycle in BCR-ABL-expressing Alox5$^{-/-}$ bone marrow cells. This further indicates that there is no differentiation blockade in Alox5$^{-/-}$ HSCs and that Alox5 deficiency has distinct biological effect on normal HSCs and LSCs.

Figure 25:
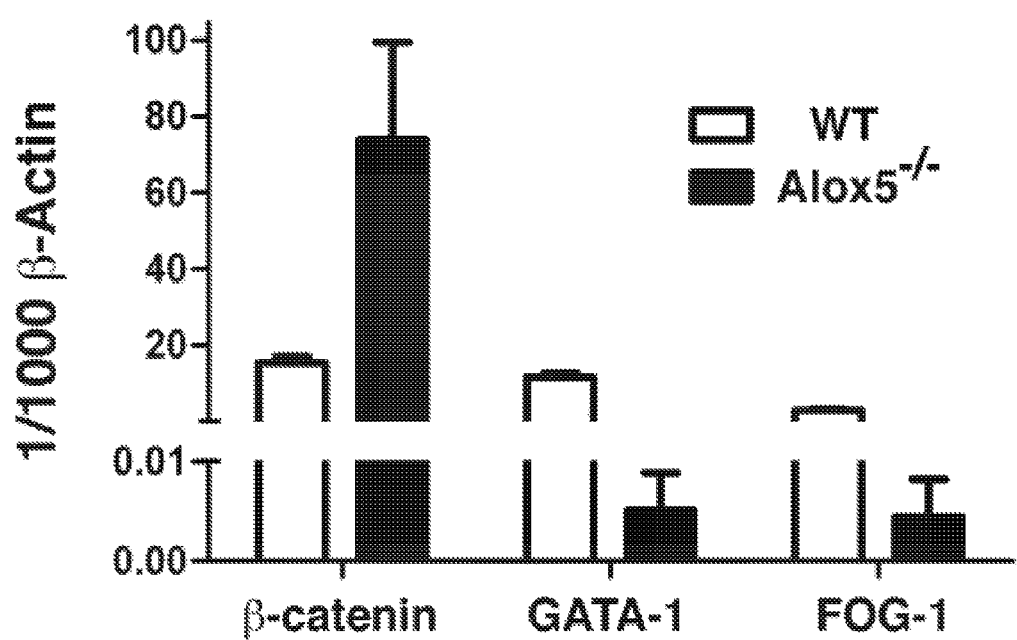
FIG. 25 is a graph showing RT-PCR expression of β-catenin, GATA-1 and FOG from FACS sorted bone marrow HSCs of wild type (WT) and Alox5$^{-/-}$ mice.

The expression levels of three regulatory genes of hematopoiesis, β-catenin, GATA-1 and FOG-1 are determined by Real Time RT-PCR. β-actin expression is used for normalization. Total RNA is isolated from bone marrow HSC (Lin$^-$c-Kit$^+$Sca-1$^+$) cells of wild type (WT) and Alox5$^{-/-}$ mice. cDNA is synthesized using the Ovation-Pico cDNA synthesis method. The analysis is done in triplicate. Decreased expression of GATA-1 and FOG-1, and increased β-catenin expression is found Alox5$^{-/-}$ HSCs compared to that in wild type HSCs, shown in FIG. 25. Different expression patterns of β-catenin, GATA-1 and FOG-1 in Alox5$^{-/-}$ HSCs, FIG. 25, and LSCs, indicate that these three genes function differently in these two types of stem cells.

Example 8

Effect of Curcumin on Leukemia Cells and LSCs

Figure 26:
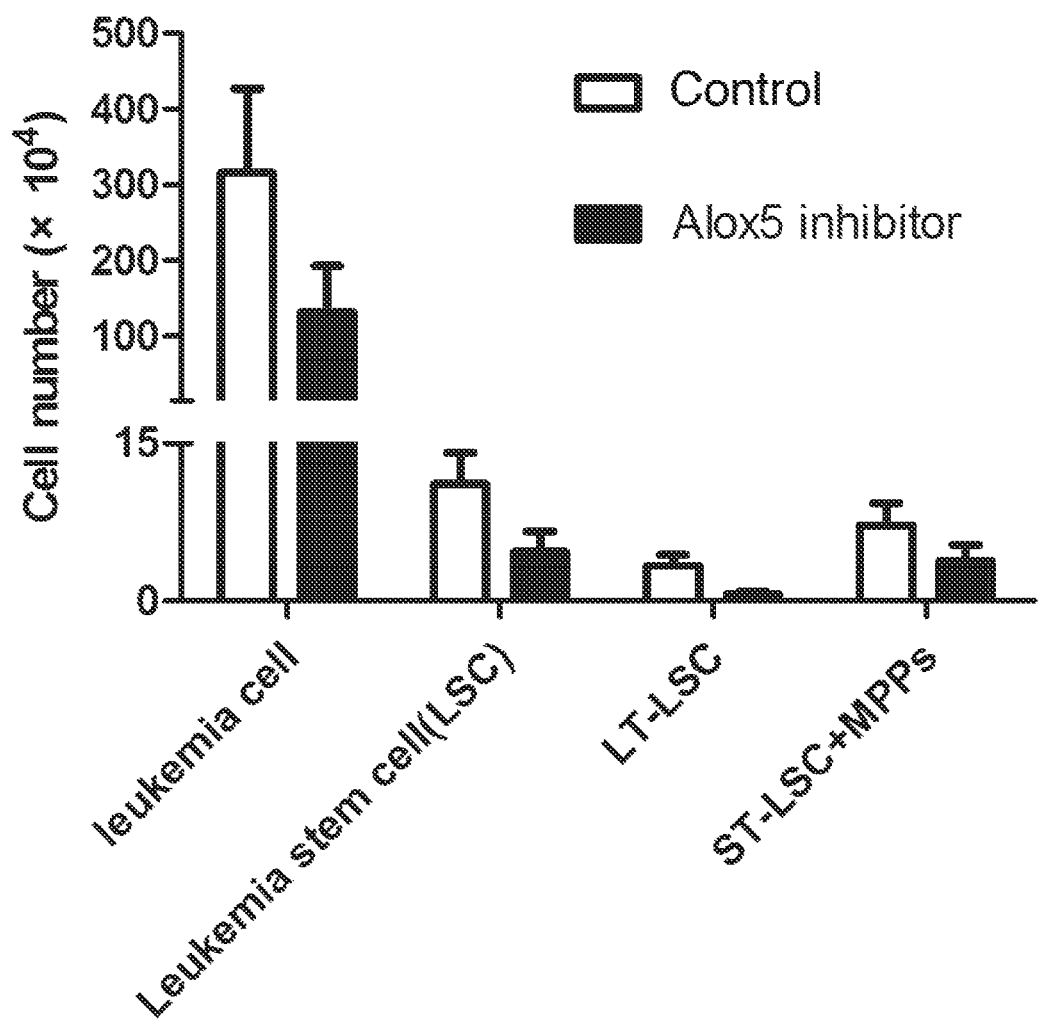
FIG. 26 is a graph showing the effect of the 5-LO inhibitor curcumin on LSC, LT-LSC and ST-LSC+MPPs.

Bone marrow cells are isolated from 6- to 10-week-old C57BL/6 (B6) mice induced with BCR-ABL, for example using the retroviral vector MSCV-IRES-eGFP carrying the p210 BCR-ABL cDNA to produce CML mice. Total bone marrow cells were cultured in vitro in the presence of StemSpan serum-free medium (StemCell Technologies, Vancouver, BC) supplemented with 10 μg/mL heparin (Sigma, St Louis, Mo.), 10 ng/mL mouse SCF, 20 ng/mL mouse TPO, 20 ng/mL mouse IGF-2 (all from R&D Systems, Minneapolis, Minn.), and 10 ng/mL human FGF-1 (Invitrogen, Carlsbad, Calif.). Half of the medium was replaced after 3 days with fresh medium. (Peng et al Blood, 15 Jul. 2007, Vol. 110, No. 2, pp. 678-685; Zhang and Lodish Blood, 1 Jun. 2005, Vol. 105, No. 11, pp. 4314-4320; de Haan et al. Dev Cell 2003; 4:241-251). The cells were cultured for 6 days in the presence or absence of the Alox5 inhibitor, curcumin at (1,7-Bis(4-hydroxy-3-methoxyphenyl)-1,6-heptadiene-3,5-dione; Calbiochem cat. no. 239802) a concentration of 20 μM in vitro (5×10$^6$ cells/6 cm tissue culture plate) at 37° C. in a 5% $CO_2$ tissue culture incubator. Then cells were washed with PBS, stained with B220-PE for B cells, Gr-1-APC for neutrophils, Mac-1-PE for macrophage, CD3E-APC for T cells, and Sca-1-PE-cy7/c-Kit-APC-cy7/CD34-APC/CD135 (Flt3)-PE for hematopoietic stem cells, and sorted by FACS analysis. Total live cell numbers were measured for leukemia cells, leukemia stem cells, long-term LSC (LT-LSC) and short-term LSCs with multipotent progenitor cells (ST-LSC+MPP). The FACS markers used for leukemia cells are GFP+Gr-1+, for LSCs are GFP$^+$Lin$^-$c-Kit$^+$Sca-1$^+$, for LT-LSC are GFP$^+$Lin$^-$c-Kit$^+$Sca-1$^+$CD34$^-$, for ST-LSC+MPP are GFP$^+$Lin$^-$c-Kit$^+$Sca-1$^+$CD34$^+$ In FIG. 26 the effect of curcumin (Alox5 inhibitor) is shown in on wild type cells treated with buffer (control) and treated with curcumin (Alox5 inhibitor). Compared are leukemia cells, LSCs, long-term LSC (LT-LSC) and short-term LSC (ST-LSC) with multipotent progenitor cells (ST-LSC+MPP). In all cases the cell number is reduced when curcumin is present in the culture. This shows that curcumin can inhibit leukemia stem cells.

Example 9

Effect of Curcumin on K562 Cells

Figure 27:
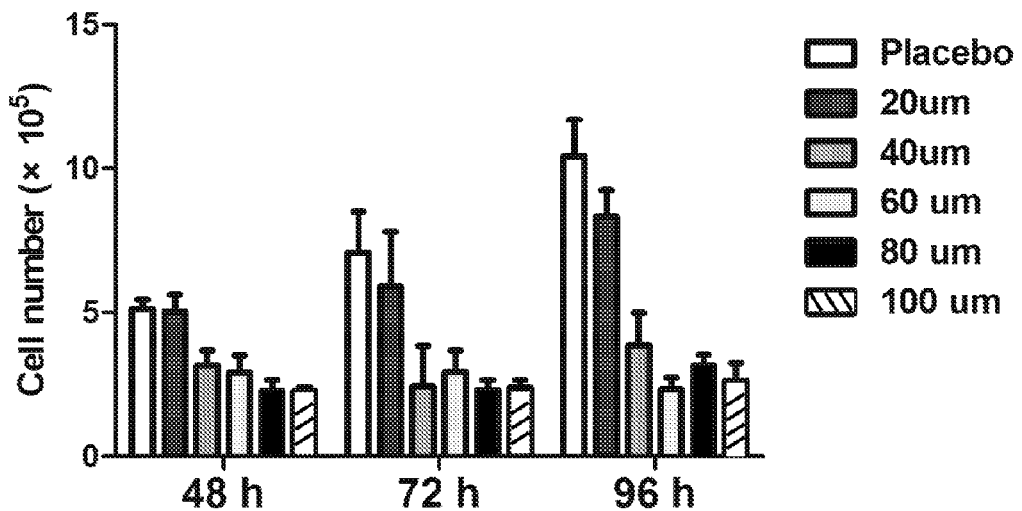
FIG. 27 is a graph showing the effect of the 5-LO inhibitor curcumin on the proliferation of K562 cells.

Human K562 myeloid leukemia cells (ATCC, CCL-243) are cultured in RPMI 1640 medium containing 10% FCS at 37° C. in a 5% $CO_2$ tissue culture incubator. 5×10$^5$ cells/well were plated into 24-well tissue culture grade plates. The cells are treated with curcumin at 5 different concentrations (20 μM; 40 μM; 60 μM; 80 μM; 100 μM) for 48, 72 and 96 hours. The cells are stained with trypan blue and counted. The total cell number of live cells is shown in the graph in FIG. 27. Curcumin reduces the number of live cells in all groups when cultured for 72 or 96 hours. At 48 hours curcumin shows an effect when administered at 40 μM or higher. This shows that curcumin inhibits myeloid leukemia cells.

Example 10

Assay for Determination of Effect of Zileuton on Cell Proliferation in K562 Cells K562 is a human Bcr-Abl positive CML cell line, which was isolated from a CML patient in blast crisis (Koeffler, H. P., and Golde, D. W. 1980. Human myeloid leukemia cell lines: a review. Blood 56, 344-350). This cell line is commonly used for screening compounds to detect anti-proliferative activities of leukemia cells and for the pharmacology and toxicology studies required for IND (Investigational New Drug) application. K562 is one of several myeloid leukemia cell lines well-known as a model system of myeloid leukemia (see, e.g. Rucker, F. G. et al., Molecular profiling reveals myeloid leukemia cell lines to be faithful model systems characterized by distinct genomic aberrations. Leukemia, 2006, 20:994-1001).

Figure 28:
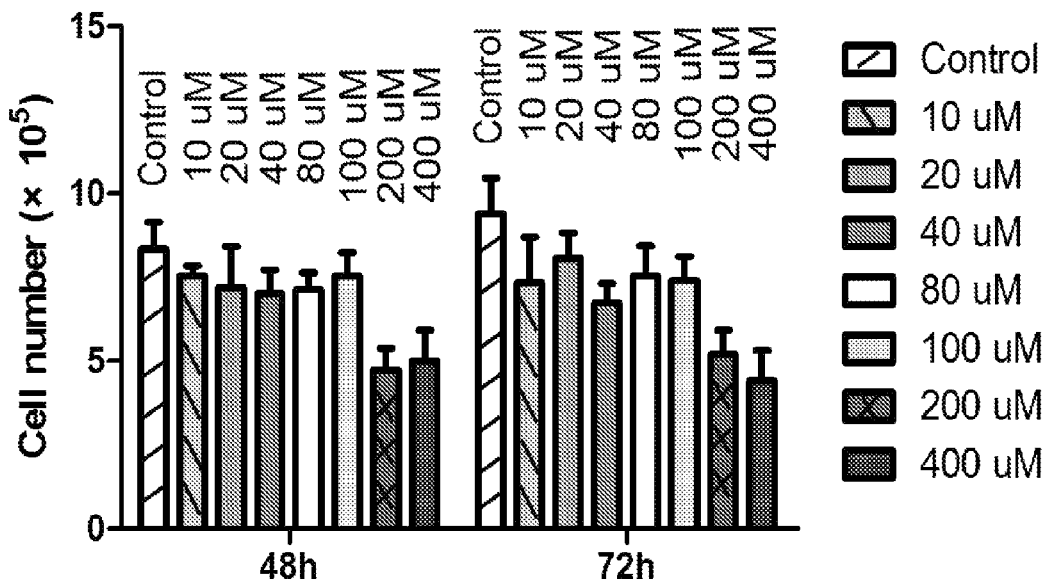
FIG. 28 is a graph showing the effect of zileuton on the proliferation of K562 cells.

K562 myeloid leukemia cells (ATCC, CCL-243) are cultured in RPMI 1640 medium containing 10% FCS (fetal calf serum) at 37° C. in a 5% $CO_2$ tissue culture incubator. $5 \times 10^5$ cells/well were plated into 24-well tissue culture grade plates. The cells are treated with zileuton at 7 different concentrations (10 µM; 20 µM; 40 µM; 80 µM; 100 µM; 200 µM; 400 µM) for 48, and 72 hours. The cells are stained with trypan blue and counted. The total cell number of live cells following these treatments is shown in the graph in FIG. 28. Zileuton reduces the number of live cells in the 200 µM and 400 µM groups when cultured for 48. At 72 hours zileuton shows an effect at all concentrations, but the strongest effect when administered at 200 µM or 400 µM. This shows that zileuton inhibits myeloid leukemia cells.

Example 11

Assay for Determination of Effect of Zileuton on Human CML CD34+CD38– Cells

Figure 29:
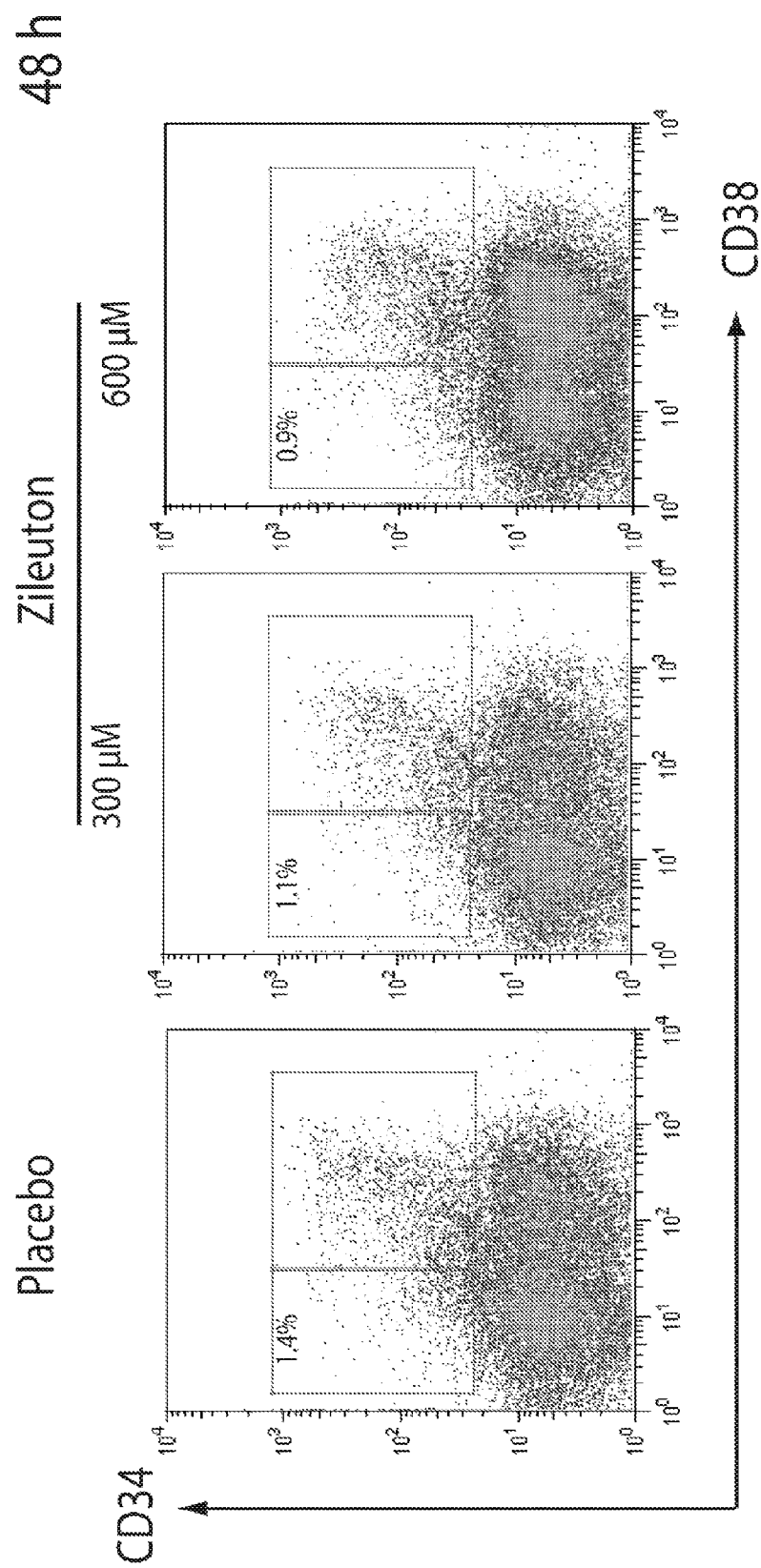
FIG. 29 is a FACS histogram for CML-SCs (CD34$^+$CD38$^-$) from bone marrow cells isolated from a CML patient and cultured for 48 hours in the presence of placebo (control), 300 μM or 600 μM zileuton to detect CML-SCs (CD34$^+$CD38$^-$).

Bone marrow was isolated from a CML patient. The cells were cultured in serum-free media (SFM: Iscove modified Dulbecco medium (Sigma-Aldrich) supplemented with a serum substitute bovine serum albumin/insulin/transferrin, BIT9500 from StemCell Technologies), five growth factors (5GF: cocktail of 20 ng/mL recombinant human IL-3 (rhIL-3), 20 ng/mL rhIL-6, 100 ng/mL rhFlt3-ligand, 100 ng/mL rh stem cell factor, available from StemCell Technologies)) and zileuton at two doses, 300 µM or 600 µM, for 48 hours. The cells were analyzed by FACS and the percentages of leukemia stem cells (CD34+CD38–) were determined using anti CD34 and anti CD38 antibodies. In FIG. 29 the FACS results show that after 48 h treatment the leukemia stem cell population is reduced from 1.4% in untreated, to 1.1% in 300 µM zileuton treatment group and to 0.9% in the 600 µM zileuton treatment group.

Example 12

Assay for Determination of Effect of Tepoxalin on Cell Proliferation K562 Cells

K562 myeloid leukemia cells (ATCC, CCL-243) are cultured in RPMI 1640 medium containing 10% FCS (fetal calf serum) at 37° C. in a 5% $CO_2$ tissue culture incubator. $5 \times 10^5$ cells/well are plated into 24-well tissue culture grade plates. The cells are treated with tepoxalin at 7 different concentrations (10 µM; 20 µM; 40 µM; 80 µM; 100 µM; 200 µM; 400 µM) for 48 and 72 hours. Then, the cells are stained with trypan blue and counted. A decrease in the number of live cells in tepoxalin treatment groups compared to the number of live cells in untreated cells is indicative of an inhibitory effect on tepoxalin on myeloid leukemia cells.

Example 13

Assay for Determination of Effect of Darbufelone on Cell Proliferation K562 Cells K562 myeloid leukemia cells (ATCC, CCL-243) are cultured in RPMI 1640 medium containing 10% FCS (fetal calf serum) at 37° C. in a 5% $CO_2$ tissue culture incubator. $5 \times 10^5$ cells/well are plated into 24-well tissue culture grade plates. The cells are treated with darbufelone mesilate at 7 different concentrations (10 µM; 20 µM; 40 µM; 80 µM; 100 µM; 200 µM; 400 µM) for 48 and 72 hours. Then, the cells are stained with trypan blue and counted. The number of live cells is plotted on graph. A decrease in the number of live cells in darbufelone mesilate treatment groups compared to the number of live cells in untreated cells is indicative of an inhibitory effect on darbufelone mesilate on myeloid leukemia cells.

To determine the 50% inhibition of the growth ($IC_{50}$) an MTT assay can be performed. K562 cell proliferation is measured either by counting viable cells by using the 3-(4,5-dimethylthiazol-2-yl)-2,5-diphenyltetrazolium bromide (MTT) (Sigma-Aldrich, St. Louis, Mo.) colorimetric dye-reduction method. K562 cells are plated $5 \times 10^3$ cells/well are plated into 96-well plates and cultured in the presence of darbufelone mesilate at different concentrations (10 µM; 20 µM; 40 µM; 80 µM; 100 µM; 200 µM; 400 µM) or untreated. Conditioned media is removed after 72 hours and cells in the 96-well plates are incubated with 0.5 mg/ml MTT for 90 min. After centrifugation, the medium is aspirated, and cells are solubilized in 200 µl of dimethyl sulfoxide. The optical density of each sample at 550 nm is measured using a microplate reader. The optical density of the media is proportional to the number of viable cells. The level of inhibition is measured as a percentage of control growth (no drug in the sample).

Example 14

Assay for Determination of Effect of Licofelone on Cell Proliferation K562 Cells K562 myeloid leukemia cells (ATCC, CCL-243) are cultured in RPMI 1640 medium containing 10% FCS (fetal calf serum) at 37° C. in a 5% $CO_2$ tissue culture incubator. $5 \times 10^5$ cells/well are plated into 24-well tissue culture grade plates. The cells are treated with licofelone at 7 different concentrations (10 µM; 20 µM; 40 µM; 80 µM; 100 µM; 200 µM; 400 µM) for 48 and 72 hours. Then, the cells are stained with trypan blue and counted. A decrease in the number of live cells in licofelone treatment groups compared to the number of live cells in untreated cells is indicative of an inhibitory effect on licofelone on myeloid leukemia cells.

To determine the 50% inhibition of the growth ($IC_{50}$) a MTT assay can be performed. K562 cell proliferation is measured either by counting viable cells by using the 3-(4,5-dimethylthiazol-2-yl)-2,5-diphenyltetrazolium bromide (MTT) (Sigma-Aldrich, St. Louis, Mo.) colorimetric dye-reduction method. K562 cells are plated $5 \times 10^3$ cells/well are plated into 96-well plates and cultured in the presence of licofelone at different concentrations (10 µM; 20 µM; 40 µM; 80 µM; 100 µM; 200 µM; 400 µM) or untreated. Conditioned media is removed after 72 hours and cells in the 96-well plates are incubated with 0.5 mg/ml MTT for 90 min. After centrifugation, the medium is aspirated, and cells are solubilized in 200 µl of dimethyl sulfoxide. The optical density of each sample at 550 nm is measured using a microplate reader. The optical density of the media is proportional to the number of viable cells. The level of inhibition is measured as a percentage of control growth (no drug in the sample).

Example 15

Assay for Determination of Effect of Minocycline on Cell Proliferation K562 Cells K562 myeloid leukemia cells (ATCC, CCL-243) are cultured in RPMI 1640 medium containing 10% FCS (fetal calf serum) at 37° C. in a 5% $CO_2$ tissue culture incubator. $5 \times 10^5$ cells/well are plated into 24-well tissue culture grade plates. The cells are treated with Minocycline at 7 different concentrations (10 µM; 20 µM; 40 µM; 80 µM; 100 µM; 200 µM; 400 µM) for 48 and 72 hours. Minocycline is a semisynthetic tetracycline that also inhibits 5-lipoxygenase. Then, the cells are stained with trypan blue and counted. A decrease in the number of live cells in minocycline treatment groups compared to the number of live cells in untreated cells is indicative of an inhibitory effect on minocycline on myeloid leukemia cells.

To determine the 50% inhibition of the growth ($IC_{50}$) a MTT assay can be performed. K562 cell proliferation is measured either by counting viable cells by using the 3-(4,5-dimethylthiazol-2-yl)-2,5-diphenyltetrazolium bromide (MTT) (Sigma-Aldrich, St. Louis, Mo.) colorimetric dye-reduction method. K562 cells are plated $5 \times 10^3$ cells/well are plated into 96-well plates and cultured in the presence of minocycline at different concentrations (10 µM; 20 µM; 40 µM; 80 µM; 100 µM; 200 µM; 400 µM) or untreated. Conditioned media is removed after 72 hours and cells in the 96-well plates are incubated with 0.5 mg/ml MTT for 90 min. After centrifugation, the medium is aspirated, and cells are solubilized in 200 µl of dimethyl sulfoxide. The optical density of each sample at 550 nm is measured using a microplate reader. The optical density of the media is proportional to the number of viable cells. The level of inhibition is measured as a percentage of control growth (no drug in the sample).

Example 16

Assay for Determination of Effect of AM679 on Cell Proliferation K562 Cells

K562 myeloid leukemia cells (ATCC, CCL-243) are cultured in RPMI 1640 medium containing 10% FCS (fetal calf serum) at 37° C. in a 5% $CO_2$ tissue culture incubator. $5 \times 10^5$ cells/well are plated into 24-well tissue culture grade plates. The cells are treated with an inhibitor of 5-lipoxygenase-activating protein: 3-{5-((S)-1-Acetyl-2,3-dihydro-1H-indol-2-ylmethoxy)-3-tert-butylsulfanyl-1-[4-(5-methoxy-pyrimidin-2-yl)-benzyl]-1H-indol-2-yl}-2,2-dimethyl-propionic acid, known as AM679, at 7 different concentrations (10 µM; 20 µM; 40 µM; 80 µM; 100 µM; 200 µM; 400 µM) for 48 and 72 hours. Then, the cells are stained with trypan blue and counted. A decrease in the number of live cells in AM679 treatment groups compared to the number of live cells in untreated cells is indicative of an inhibitory effect on AM679 on myeloid leukemia cells.

To determine the 50% inhibition of the growth ($IC_{50}$) a MTT assay can be performed. K562 cell proliferation is measured either by counting viable cells by using the 3-(4,5-dimethylthiazol-2-yl)-2,5-diphenyltetrazolium bromide (MTT) (Sigma-Aldrich, St. Louis, Mo.) colorimetric dye-reduction method. K562 cells are plated $5 \times 10^3$ cells/well are plated into 96-well plates and cultured in the presence of AM679 at different concentrations (10 µM; 20 µM; 40 µM; 80 µM; 100 µM; 200 µM; 400 µM) or untreated. Conditioned media is removed after 72 hours and cells in the 96-well plates are incubated with 0.5 mg/ml MTT for 90 min. After centrifugation, the medium is aspirated, and cells are solubilized in 200 µl of dimethyl sulfoxide. The optical density of each sample at 550 nm is measured using a microplate reader. The optical density of the media is proportional to the number of viable cells. The level of inhibition is measured as a percentage of control growth (no drug in the sample).

Example 17

Assay for Determination of Effect of DHDMBF on Cell Proliferation K562 Cells

K562 myeloid leukemia cells (ATCC, CCL-243) are cultured in RPMI 1640 medium containing 10% FCS (fetal calf serum) at 37° C. in a 5% $CO_2$ tissue culture incubator. $5 \times 10^5$ cells/well are plated into 24-well tissue culture grade plates. The cells are treated with DHDMBF at 7 different concentrations (10 µM; 20 µM; 40 µM; 80 µM; 100 µM; 200 µM; 400 µM) for 48 and 72 hours. Then, the cells are stained with trypan blue and counted. A decrease in the number of live cells in DHDMBF treatment groups compared to the number of live cells in untreated cells is indicative of an inhibitory effect on DHDMBF on myeloid leukemia cells.

To determine the 50% inhibition of the growth ($IC_{50}$) a MTT assay can be performed. K562 cell proliferation is measured either by counting viable cells by using the 3-(4,5-dimethylthiazol-2-yl)-2,5-diphenyltetrazolium bromide (MTT) (Sigma-Aldrich, St. Louis, Mo.) colorimetric dye-reduction method. K562 cells are plated $5 \times 10^3$ cells/well are plated into 96-well plates and cultured in the presences of DHDMBF at different concentrations (10 µM; 20 µM; 40 µM; 80 µM; 100 µM; 200 µM; 400 µM) or untreated. Conditioned media is removed after 72 hours and cells in the 96-well plates are incubated with 0.5 mg/ml MTT for 90 min. After centrifugation, the medium is aspirated, and cells are solubilized in 200 µl of dimethyl sulfoxide. The optical density of each sample at 550 nm is measured using a microplate reader. The optical density of the media is proportional to the number of viable cells. The level of inhibition is measured as a percentage of control growth (no drug in the sample).

Example 18

Assay for Determination of Effect of CI986 on Cell Proliferation K562 Cells

K562 myeloid leukemia cells (ATCC, CCL-243) are cultured in RPMI 1640 medium containing 10% FCS (fetal calf serum) at 37° C. in a 5% $CO_2$ tissue culture incubator. $5 \times 10^5$ cells/well are plated into 24-well tissue culture grade plates. The cells are treated with GSK-CI986 at 7 different concentrations (10 µM; 20 µM; 40 µM; 80 µM; 100 µM; 200 µM; 400 µM) for 48 and 72 hours. Then, the cells are stained with trypan blue and counted. A decrease in the number of live cells in CI986 treatment groups compared to the number of live cells in untreated cells is indicative of an inhibitory effect on CI986 on myeloid leukemia cells.

To determine the 50% inhibition of the growth ($IC_{50}$) a MTT assay can be performed. K562 cell proliferation is measured either by counting viable cells by using the 3-(4,5-dimethylthiazol-2-yl)-2,5-diphenyltetrazolium bromide (MTT) (Sigma-Aldrich, St. Louis, Mo.) colorimetric dye-reduction method. K562 cells are plated $5 \times 10^3$ cells/well are plated into 96-well plates and cultured in the presences of CI986 at different concentrations (10 µM; 20 µM; 40 µM; 80 µM; 100 µM; 200 µM; 400 µM) or untreated. Conditioned media is removed after 72 hours and cells in the 96-well plates are incubated with 0.5 mg/ml MTT for 90 min. After centrifugation, the medium is aspirated, and cells are solubilized in 200 µl of dimethyl sulfoxide. The optical density of each sample at 550 nm is measured using a microplate reader. The optical density of the media is proportional to the number of viable cells. The level of inhibition is measured as a percentage of control growth (no drug in the sample).

Example 19

Assay for Determination of Effect of Atreleuton on Cell Proliferation K562 Cells K562 myeloid leukemia cells (ATCC, CCL-243) are cultured in RPMI 1640 medium containing 10% FCS (fetal calf serum) at 37° C. in a 5% $CO_2$ tissue culture incubator. $5\times10^5$ cells/well are plated into 24-well tissue culture grade plates. The cells are treated with atreleuton (VIA-2291, ABT-761) at 7 different concentrations (10 µM; 20 µM; 40 µM; 80 µM; 100 µM; 200 µM; 400 µM) for 48 and 72 hours. Then, the cells are stained with trypan blue and counted. A decrease in the number of live cells in atreleuton treatment groups compared to the number of live cells in untreated cells is indicative of an inhibitory effect on atreleuton on myeloid leukemia cells.

To determine the 50% inhibition of the growth ($IC_{50}$) a MTT assay can be performed. K562 cell proliferation is measured either by counting viable cells by using the 3-(4,5-dimethylthiazol-2-yl)-2,5-diphenyltetrazolium bromide (MTT) (Sigma-Aldrich, St. Louis, Mo.) colorimetric dye-reduction method. K562 cells are plated $5\times10^3$ cells/well are plated into 96-well plates and cultured in the presences of atreleuton at different concentrations (10 µM; 20 µM; 40 µM; 80 µM; 100 µM; 200 µM; 400 µM) or untreated. Conditioned media is removed after 72 hours and cells in the 96-well plates are incubated with 0.5 mg/ml MTT for 90 min. After centrifugation, the medium is aspirated, and cells are solubilized in 200 µl of dimethyl sulfoxide. The optical density of each sample at 550 nm is measured using a microplate reader. The optical density of the media is proportional to the number of viable cells. The level of inhibition is measured as a percentage of control growth (no drug in the sample).

Example 20

Patients with symptoms of Chronic Myelogenous Leukemia (CML) are selected and tested for the presence of the Philadelphia chromosome (cytogenetic testing) or BCR-ABL positive (FISH or PCR testing) or for Tel-PDGFR-beta translocation (cytogenetic testing, FISH or PCR). The identified patients are treated with the 5-lipoxygenase (5-LO) inhibitor zileuton at a daily dose of 600 mg, 600 mg twice a day (BID) or 600 mg four times a day (QID). The dose may be changed to a higher dose if only partial or minor response is observed after 3 months or after 6 months.

Responses to the treatment are evaluated initially after two weeks and then at 12 week intervals. The hematologic, cytogenetic and molecular responses are measured. A complete hematologic response to the treatment is accomplished when white blood cell (WBC), platelet, and red blood cell (RBC) counts have returned to a normal range. For example, the platelet count should be below $450\times10^9$/L, the white blood cell count below $10\times10^9$/L. The differential should show no immature granulocyte (monocytes, polymorphonuclear cells (PMC), myeloblasts (MB)) and less than 5% basophils. Further, the spleen of the patient should not be palpable.

Achieving a cytogenetic response has been established as a surrogate marker for an improved probability of survival in CML. A complete cytogenetic response (CCyR) is the detection of 0% Philadelphia chromosome in 20 metaphases analyzed (G banding); a partial response (PCyR) is the detection of 1% to 35% Philadelphia chromosomes; a minor response (MCyR) is the detection of 36% to 65%; and minimal response is the detection of 66% to 95% Philadelphia chromosomes in 20 metaphases. Instead of G banding, interphase fluorescence in situ hybridization (FISH) analysis can be performed on either blood or bone marrow samples.

The molecular response is measured using blood and isolating RNA for quantitative RT-PCR analysis. No BCR-ABL transcripts are detectable in the case of a complete response. Detection of 0.10 or lower compared to the control gene ratio is considered a major molecular response.

Example 21

Patients with symptoms of CML are selected and tested for the presence of the Philadelphia chromosome (cytogenetic testing) or BCR-ABL positive (FISH or PCR testing) or for Tel-PDGFR-beta translocation (cytogenetic testing, FISH or PCR). The identified patients are treated with the 5-lipoxygenase (5-LO) inhibitor zileuton and imatinib. Imatinib is initially administered at a dose 400 mg daily. Zileuton is initially administered at a daily dose of 600 mg, 600 mg twice a day (BID) or 600 mg four times a day (QID). The dose may be changed to a higher dose if only partial or minor response is observed after 3 months or after 6 months. For imatinib the dose may be increased to 600 mg daily or 400 mg twice a day depending on the initial diagnosis and hematologic response, cytogenetic and molecular response during the course of the treatment. The dose may be changed to a higher dose if only partial or minor response has been observed after 3 months or after 6 months.

Responses to the treatment are evaluated initially after two weeks and then at 12 week intervals. The hematologic, cytogenetic and molecular responses are measured and evaluated, for example, as described and using criteria in Example 20.

Example 22

Patients with symptoms of CML are selected and tested for the presence of the Philadelphia chromosome (cytogenetic testing) or BCR-ABL positive (FISH or PCR testing) or for Tel-PDGFR-beta translocation (cytogenetic testing, FISH or PCR). The identified patients are treated with the 5-lipoxygenase (5-LO) inhibitor zileuton and the heat shock protein 90 (HSp90) inhibitor IPI-504 (retaspimycin hydrochloride). IPI-504 is administered intravenously (IV) at a dose 400 mg/m² twice weekly or 3-weekly. Zileuton is initially administered at a daily dose of 600 mg, 600 mg twice a day (BID) or 600 mg four times a day (QID). The dose may be changed to a higher dose if only partial or minor response is observed after 3 months or after 6 months. For IPI-504 the dose may be increased to 550 mg/m² g biweekly or 3-weekly or reduced to 300 mg/m² biweekly or 3-weekly depending on the initial diagnosis and hematologic, cytogenetic and molecular response during the course of the treatment. The dose may be changed to a higher dose if only partial or minor response has been observed after 3 months or after 6 months.

Responses to the treatment are evaluated initially after two weeks and then at 12 week intervals. The hematologic, cytogenetic and molecular responses are measured and evaluated, for example, as described and using criteria in Example 20.

Example 23

Patients with symptoms of CML are selected and tested for the presence of the Philadelphia chromosome (cytogenetic testing) or BCR-ABL positive (FISH or PCR testing) or for Tel-PDGFR-beta translocation (cytogenetic testing, FISH or PCR). The identified patients are treated with the 5-lipoxygenase (5-LO) inhibitor zileuton and the heat shock protein 90 (HSp90) inhibitor tanespimycin (KOS-953). Tanespimycin is administered intravenously (IV) at a dose 340 mg/m$^2$ twice weekly or 3-weekly for 2 weeks in a 3 week cycle. Zileuton is initially administered at a daily dose of 600 mg, 600 mg twice a day (BID) or 600 mg four times a day (QID). The dose may be changed to a higher dose if only partial or minor response is observed after 3 months or after 6 months. For tanespimycin the dose may be increased to 600 mg/m$^2$ biweekly or 3-weekly or reduced to 300 mg/m$^2$ biweekly or 3-weekly depending on the initial diagnosis and hematologic, cytogenetic and molecular response during the course of the treatment. The dose may be changed to a higher dose if only partial or minor response has been observed after 3 months or after 6 months.

Responses to the treatment are evaluated initially after two weeks and then at 12 week intervals. The hematologic, cytogenetic and molecular responses are measured and evaluated, for example, as described and using criteria in Example 20.

Example 24

Patients with symptoms of CML are selected and tested for the presence of the Philadelphia chromosome (cytogenetic testing) or BCR-ABL positive (FISH or PCR testing) or for Tel-PDGFR-beta translocation (cytogenetic testing, FISH or PCR). The identified patients are treated with the 5-lipoxygenase (5-LO) inhibitor zileuton and the dual kinase inhibitor dasatinib (SPRYCEL™). Dasatinib is initially administered at a dose 100 mg daily or 50 mg twice a day. Zileuton is initially administered at a daily dose of 600 mg, 600 mg twice a day (BID) or 600 mg four times a day (QID). The dose may be changed to a higher dose if only partial or minor response is observed after 3 months or after 6 months. For dasatinib the dose may be increased to 140 mg daily or 70 mg twice a day depending or reduced to 50 mg daily on the initial diagnosis and hematologic response, cytogenetic and molecular response during the course of the treatment. The dose may be changed to a higher dose if only partial or minor response has been observed after 3 months or after 6 months.

Responses to the treatment are evaluated initially after two weeks and then at 12 week intervals. The hematologic, cytogenetic and molecular responses are measured and evaluated, for example, as described and using criteria in Example 20.

Example 25

Patients with symptoms of CML are selected and tested for the presence of the Philadelphia chromosome (cytogenetic testing) or BCR-ABL positive (FISH or PCR testing) or for Tel-PDGFR-beta translocation (cytogenetic testing, FISH or PCR). The identified patients are treated with the 5-lipoxygenase (5-LO) inhibitor zileuton and the heat shock protein 90 (Hsp90) inhibitor STA-9090. STA-9090 is administered intravenously (IV) at a dose 38 mg/m$^2$ once a week for three weeks, followed by one week of dose-free interval. Zileuton is initially administered at a daily dose of 600 mg, 600 mg twice a day (BID) or 600 mg four times a day (QID). The dose may be changed to a higher dose if only partial or minor response is observed after 3 months or after 6 months. For STA-9090 the dose may be increased up to 218 mg/m$^2$ a week or reduced to 10 mg/m$^2$, 14 mg/m$^2$ or 24 mg/m$^2$ a week depending on the initial diagnosis and hematologic, cytogenetic and molecular response during the course of the treatment. Instead of weekly dosing the dose may be halved and administered biweekly. The dose may be changed to a higher dose if only partial or minor response has been observed after 3 months or after 6 months.

Responses to the treatment are evaluated initially after two weeks and then at 12 week intervals. The hematologic, cytogenetic and molecular responses are measured and evaluated, for example, as described and using criteria in Example 20.

Example 26

Patients with symptoms of CML are selected and tested for the presence of the Philadelphia chromosome (cytogenetic testing) or BCR-ABL positive (FISH or PCR testing) or for Tel-PDGFR-beta translocation (cytogenetic testing, FISH or PCR). The identified patients are treated with the 5-lipoxygenase (5-LO) inhibitor VIA-2291 (Atreleuton) and the dual kinase inhibitor dasatinib (SPRYCEL™). Dasatinib is initially administered at a dose 100 mg daily or 50 mg twice a day. Zileuton is initially administered at a daily dose of 100 mg. The dose may be changed to a higher dose if only partial or minor response is observed after 3 months or after 6 months. For dasatinib the dose may be increased to 140 mg daily or 70 mg twice a day depending or reduced to 50 mg daily on the initial diagnosis and hematologic response, cytogenetic and molecular response during the course of the treatment. The dose may be changed to a higher dose if only partial or minor response has been observed after 3 months or after 6 months.

Responses to the treatment are evaluated initially after two weeks and then at 12 week intervals. The hematologic, cytogenetic and molecular responses are measured and evaluated, for example, as described and using criteria in Example 20.

Example 27

Patients with symptoms of CML are selected and tested for the presence of the Philadelphia chromosome (cytogenetic testing) or BCR-ABL positive (FISH or PCR testing) or for Tel-PDGFR-beta translocation (cytogenetic testing, FISH or PCR). The identified patients are treated with the 5-lipoxygenase (5-LO) inhibitor GSK2190915 and imatinib. Imatinib is initially administered at a dose 400 mg daily. GSK2190915 is initially administered at a daily dose of 150 mg, 150 mg twice a day (BID) or 150 mg four times a day (QID). The dose may be changed to a higher dose if only partial or minor response is observed after 3 months or after 6 months or to a lower dose such as 50 mg daily. For imatinib the dose may be increased to 600 mg daily or 400 mg twice a day depending on the initial diagnosis and hematologic response, cytogenetic and molecular response during the course of the treatment. The dose may be changed to a higher dose if only partial or minor response has been observed after 3 months or after 6 months.

Responses to the treatment are evaluated initially after two weeks and then at 12 week intervals. The hematologic, cytogenetic and molecular responses are measured and evaluated, for example, as described and using criteria in Example 20.

Example 28

Patients with symptoms for CML are selected and tested for the presence of the Philadelphia chromosome (cytogenetic testing) or BCR-ABL positive (FISH or PCR testing) or for Tel-PDGFR-beta translocation (cytogenetic testing, FISH or PCR). The identified patients are treated with the 5-lipoxygenase (5-LO) inhibitor GSK2190915 and the dual kinase inhibitor dasatinib (SPRYCEL™). Dasatinib is initially administered at a dose 100 mg daily or 50 mg twice a day. GSK2190915 is initially administered at a daily dose of 150 mg, 150 mg twice a day (BID) or 150 mg four times a day (QID). The dose may be changed to a lower dose such as 50 mg daily in the case of response or to a higher dose if only partial or minor response is observed after 3 months or after 6 months. For dasatinib the dose may be increased to 140 mg daily or 70 mg twice a day depending or reduced to 50 mg daily on the initial diagnosis and hematologic response, cytogenetic and molecular response during the course of the treatment. The dose may be changed to a higher dose if only partial or minor response has been observed after 3 months or after 6 months.

Responses to the treatment are evaluated initially after two weeks and then at 12 week intervals. The hematologic, cytogenetic and molecular responses are measured and evaluated, for example, as described and using criteria in Example 20.

Example 29

Patients with symptoms of CML are selected and tested for the presence of the Philadelphia chromosome (cytogenetic testing) or BCR-ABL positive (FISH or PCR testing) or for Tel-PDGFR-beta translocation (cytogenetic testing, FISH or PCR) treated with the 5-lipoxygenase (5-LO) inhibitor VIA-2291 (Atreleuton) at a daily dose of 100 mg for up to 24 months depending on the response of the patient. Alternatively the dose may be 100 mg twice a day (BID) or four times a day (QID). The dose may be changed to a higher dose when only partial or minor response has been observed after 3 months or after 6 months.

Responses to the treatment are evaluated initially after two weeks and then in 12 week intervals. The hematologic, cytogenetic and molecular responses are measured and evaluated, for example, as described and using criteria in Example 20.

Example 30

Patients with symptoms of CML are selected and tested for the presence of the Philadelphia chromosome (cytogenetic testing) or BCR-ABL positive (FISH or PCR testing) or for Tel-PDGFR-beta translocation (cytogenetic testing, FISH or PCR) treated with the 5-lipoxygenase (5-LO) inhibitor licofelone (ML3000) and the dual kinase inhibitor dasatinib (SPRYCEL™). Dasatinib is initially administered at a dose 100 mg daily or 50 mg twice a day. Licofelone is administered at a daily dose of 2.5 mg/kg for up to 24 months depending on the response of the patient. Alternatively the dose may be 2.5 mg/kg twice a day (BID) or four times a day (QID). Dasatinib is initially administered at a dose 100 mg daily or 50 mg twice a day. For dasatinib the dose may be increased to 140 mg daily or 70 mg twice a day depending or reduced to 50 mg daily on the initial diagnosis and hematologic response, cytogenetic and molecular response during the course of the treatment.

Responses to the treatment are evaluated initially after two weeks and then in 12 week intervals. The hematologic, cytogenetic and molecular responses are measured and evaluated, for example, as described and using criteria in Example 20. The dose for either or both drugs may be changed to a higher dose when only partial or minor response has been observed after 3 months or after 6 months.

Example 31

Patients with symptoms of CML are selected and tested for the presence of the Philadelphia chromosome (cytogenetic testing) or BCR-ABL positive (FISH or PCR testing) or for Tel-PDGFR-beta translocation (cytogenetic testing, FISH or PCR). The identified patients are treated with the 5-lipoxygenase (5-LO) inhibitor curcumin and imatinib. Imatinib is initially administered at a dose 400 mg daily. Curcumin is initially administered at a daily dose of 4 g, 4 g twice a day (BID) or 3 g four times a day (QID). The dose may be changed to a higher dose if only partial or minor response is observed after 3 months or after 6 months. For imatinib the dose may be increased to 600 mg daily or 400 mg twice a day depending on the initial diagnosis and hematologic response, cytogenetic and molecular response during the course of the treatment. The dose may be changed to a higher dose if only partial or minor response has been observed after 3 months or after 6 months.

Responses to the treatment are evaluated initially after two weeks and then at 12 week intervals. The hematologic, cytogenetic and molecular responses are measured and evaluated, for example, as described and using criteria in Example 20. The dose for either or both drugs may be changed to a higher dose when only partial or minor response has been observed after 3 months or after 6 months.

Example 32

Patients with symptoms of MPD are treated with the 5-lipoxygenase (5-LO) inhibitor GSK2190915 and imatinib. Imatinib is initially administered at a dose 400 mg daily. GSK2190915 is initially administered at a daily dose of 150 mg, 150 mg twice a day (BID) or 150 mg four times a day (QID). The dose may be changed to a higher dose if only partial or minor response is observed after 3 months or after 6 months or to a lower dose such as 50 mg daily. For imatinib the dose may be increased to 600 mg daily or 400 mg twice a day depending on the initial diagnosis and response during the course of the treatment. The dose may be changed to a higher dose if only partial or minor response has been observed after 3 months or after 6 months.

Responses to the treatment are evaluated initially after two weeks and then at 12 week intervals.

Example 33

Patients with symptoms of MPD are selected and treated with the 5-lipoxygenase (5-LO) inhibitor GSK2190915 and the dual kinase inhibitor dasatinib (SPRYCEL™). Dasatinib is initially administered at a dose 100 mg daily or 50 mg twice a day. GSK2190915 is initially administered at a daily dose of 150 mg, 150 mg twice a day (BID) or 150 mg four times a day (QID). The dose may be changed to a lower dose such as 50 mg daily in the case of response or to a higher dose if only partial or minor response is observed after 3 months or after 6 months. For dasatinib the dose may be increased to 140 mg daily or 70 mg twice a day depending or reduced to 50 mg daily on the initial diagnosis and response during the course of the treatment. The dose may be changed to a higher dose if only partial or minor response has been observed after 3 months or after 6 months.

Responses to the treatment are evaluated initially after two weeks and then at 12 week intervals.

Example 34

Patients with symptoms of MPD are selected and treated with the 5-lipoxygenase (5-LO) inhibitor VIA-2291 (Atreleuton) at a daily dose of 100 mg for up to 24 months depending on the response of the patient. Alternatively the dose may be 100 mg twice a day (BID) or four times a day (QID). The dose may be changed to a higher dose when only partial or minor response has been observed after 3 months or after 6 months.

Responses to the treatment are evaluated initially after two weeks and then in 12 week intervals.

Example 35

Patients with symptoms of MPD are selected and treated with the 5-lipoxygenase (5-LO) inhibitor licofelone (ML3000) and the dual kinase inhibitor dasatinib (SPRYCEL™) Dasatinib is initially administered at a dose 100 mg daily or 50 mg twice a day. Licofelone is administered at a daily dose of 2.5 mg/kg for up to 24 months depending on the response of the patient. Alternatively the dose may be 2.5 mg/kg twice a day (BID) or four times a day (QID). Dasatinib is initially administered at a dose 100 mg daily or 50 mg twice a day. For dasatinib the dose may be increased to 140 mg daily or 70 mg twice a day depending or reduced to 50 mg daily on the initial diagnosis and response during the course of the treatment.

Responses to the treatment are evaluated initially after two weeks and then in 12 week intervals. The dose for either or both drugs may be changed to a higher dose when only partial or minor response has been observed after 3 months or after 6 months.

Example 36

Patients with symptoms of MPD are selected and treated with the 5-lipoxygenase (5-LO) inhibitor zileuton and imatinib. Imatinib is initially administered at a dose 400 mg daily. Zileuton is initially administered at a daily dose of 600 mg, 600 mg twice a day (BID) or 600 mg four times a day (QID). The dose may be changed to a higher dose if only partial or minor response is observed after 3 months or after 6 months. For imatinib the dose may be increased to 600 mg daily or 400 mg twice a day depending on the initial diagnosis and response during the course of the treatment. The dose may be changed to a higher dose if only partial or minor response has been observed after 3 months or after 6 months. The dose may be lower after a high response or intolerance to the drug has been observed.

Responses to the treatment are evaluated initially after two weeks and then at 12 week intervals.

REFERENCES

Al-Hajj, M., Wicha, M. S., Benito-Hernandez, A., Morrison, S. J., and Clarke, M. F. (2003). Prospective identification of tumorigenic breast cancer cells. Proceedings of the National Academy of Sciences of the United States of America 100, 3983-3988.

Catalano, A., Rodilossi, S., Caprari, P., Coppola, V., and Procopio, A. (2005). 5-Lipoxygenase regulates senescence-like growth arrest by promoting ROS-dependent p53 activation. EMBO J 24, 170-179.

Chen, X. S., Sheller, J. R., Johnson, E. N., and Funk, C. D. (1994). Role of leukotrienes revealed by targeted disruption of the 5-lipoxygenase gene. Nature 372, 179-182.

Druker, B. J. (2008). Translation of the Philadelphia chromosome into therapy for CML. Blood 112, 4808-4817.

Edelman, M. J., Watson, D., Wang, X., Morrison, C., Kratzke, R. A., Jewell, S., Hodgson, L., Mauer, A. M., Gajra, A., Masters, G. A., et al. (2008). Eicosanoid modulation in advanced lung cancer: Cyclooxygenase-2 expression is a positive predictive factor for celecoxib+ chemotherapy—Cancer and leukemia group B trial 30203. Journal of Clinical Oncology 26, 848-855.

Faderl, S., Talpaz, M., Estrov, Z., and Kantarjian, H. M. (1999a). Chronic myelogenous leukemia: Biology and therapy. Annals of Internal Medicine 131, 207-219. Faderl, S., Talpaz, M., Estrov, Z., O'Brien, S., Kurzrock, R., and Kantarjian, H. M. (1999b). The biology of chronic myeloid leukemia. New England Journal of Medicine 341, 164-172.

Funk, C. D. (2006). Lipoxygenase pathways as mediators of early inflammatory events in atherosclerosis. Arteriosclerosis, Thrombosis, and Vascular Biology 26, 1204-1206.

Israel, E., Cohn, J., DubE, L., and Drazen, J. M. (1996). Effect of treatment with zileuton, a 5-lipoxygenase inhibitor, in patients with asthma: A randomized controlled trial. Journal of the American Medical Association 275, 931-936.

Jordan, C. T., Guzman, M. L., and Noble, M. (2006). Cancer stem cells. N Engl J Med 355, 1253-1261.

Kane, G. C., Pollice, M., Kim, C. J., Cohn, J., Dworski, R. T., Murray, J. J., Sheller, J. R., Fish, J. E., and Peters, S. P. (1996). A controlled trial of the effect of the 5-lipoxygenase inhibitor, zileuton, on lung inflammation produced by segmental antigen challenge in human beings. Journal of Allergy and Clinical Immunology 97, 646-654.

Lessard, J., and Sauvageau, G. (2003). Bmi-1 determines the proliferative capacity of normal and leukaemic stem cells. Nature 423, 255-260.

Liu, M. C., Dube, L. M., Lancaster, J., Swanson, L. J., Rosenstein, L., and McConnell, M. (1996). Acute and chronic effects of a 5-lipoxygenase inhibitor in asthma: A 6-month randomized multicenter trial. Journal of Allergy and Clinical Immunology 98, 859-871.

Lowe, S. W., and Shen, C. J. (2003). Tumor suppression by Ink4a-Arf: progress and puzzles. Curr Opin Genet Dev 13, 77-83.

Molofsky, A. V., He, S., Bydon, M., Morrison, S. J., and Pardal, R. (2005). Bmi-1 promotes neural stem cell self-renewal and neural development but not mouse growth and survival by repressing the p16Ink4a and p19Arf senescence pathways. Genes Dev 19, 1432-1437.

Molofsky, A. V., Pardal, R., and Morrison, S. J. (2004). Diverse mechanisms regulate stem cell self-renewal. Curr Opin Cell Biol 16, 700-707.

Pardal, R., Clarke, M. F., and Morrison, S. J. (2003). Applying the principles of stem-cell biology to cancer. Nat Rev Cancer 3, 895-902.

Park, I. K., Qian, D., Kiel, M., Becker, M. W., Pihalja, M., Weissman, I. L., Morrison, S. J., and Clarke, M. F. (2003). Bmi-1 is required for maintenance of adult self-renewing haematopoietic stem cells. Nature 423, 302-305.

Peng, C., Li, D., and Li, S. (2007). Heat shock protein 90: a potential therapeutic target in leukemic progenitor and stem cells harboring mutant BCR-ABL resistant to kinase inhibitors. Cell Cycle 6, 2227-2231.

Radmark, O., Werz, O., Steinhilber, D., and Samuelsson, B. (2007). 5-Lipoxygenase: regulation of expression and enzyme activity. Trends in Biochemical Sciences 32, 332-341.

Ren, R. (2005). Mechanisms of BCR-ABL in the pathogenesis of chronic myelogenous leukaemia. Nature Reviews Cancer 5, 172-183.

Reya, T., and Clevers, H. (2005). Wnt signalling in stem cells and cancer. Nature 434, 843-850.

Reya, T., Morrison, S. J., Clarke, M. F., and Weissman, I. L. (2001). Stem cells, cancer, and cancer stem cells. Nature 414, 105-111.

Riccioni, G., Capra, V., D'Orazio, N., Bucciarelli, T., and Bazzano, L. A. (2008). Leukotriene modifiers in the treatment of cardiovascular diseases. Journal of Leukocyte Biology 84, 1374-1378.

Rossi, D. J., Jamieson, C. H., and Weissman, I. L. (2008). Stems cells and the pathways to aging and cancer. Cell 132, 681-696.

Singh, S. K., Clarke, I. D., Terasaki, M., Bonn, V. E., Hawkins, C., Squire, J., and Dirks, P. B. (2003). Identification of a cancer stem cell in human brain tumors. Cancer Res 63, 5821-5828.

Soberman, R. J., and Christmas, P. (2003). The organization and consequences of eicosanoid signaling. J Clin Invest 111, 1107-1113.

Steele, V. E., Holmes, C. A., Hawk, E. T., Kopelovich, L., Lubet, R. A., Crowell, J. A., Sigman, C. C., and Kelloff, G. J. (2000). Potential use of lipoxygenase inhibitors for cancer chemoprevention. Expert Opinion on Investigational Drugs 9, 2121-2138.

Taipale, J., and Beachy, P. A. (2001). The Hedgehog and Wnt signalling pathways in cancer. Nature 411, 349-354.

Wang, J. C., and Dick, J. E. (2005). Cancer stem cells: lessons from leukemia. Trends Cell Biol 15, 494-501.

Williams, F. M. K., and Spector, T. D. (2009). A new 5-lipoxygenase inhibitor seems to be safe and effective for the treatment of osteoarthritis. Nature Clinical Practice Rheumatology.

Wymann, M. P., and Schneiter, R. (2008). Lipid signalling in disease. Nat Rev Mol Cell Biol 9, 162-176.

Yilmaz, O. H., Valdez, R., Theisen, B. K., Guo, W., Ferguson, D. O., Wu, H., and Morrison, S. J. (2006). Pten dependence distinguishes haematopoietic stem cells from leukaemia-initiating cells. Nature 441, 475-482.

Yokomizo, T., Izumi, T., and Shimizu, T. (2001). Leukotriene B4: metabolism and signal transduction. Arch Biochem Biophys 385, 231-241.

Zhao, C., Blum, J., Chen, A., Kwon, H. Y., Jung, S. H., Cook, J. M., Lagoo, A., and Reya, T. (2007). Loss of beta-catenin impairs the renewal of normal and CML stem cells in vivo. Cancer Cell 12, 528-541.

Zhao, L., Moos, M. P., Grabner, R., Pedrono, F., Fan, J., Kaiser, B., John, N., Schmidt, S., Spanbroek, R., Lotzer, K., et al. (2004). The 5-lipoxygenase pathway promotes pathogenesis of hyperlipidemia-dependent aortic aneurysm. Nat Med 10, 966-973.

Reya, T. et al. A role for Wnt signalling in self-renewal of haematopoietic stem cells. Nature 423, 409-414 (2003).

Bonnet, D. & Dick, J. E. Human acute myeloid leukemia is organized as a hierarchy that originates from a primitive hematopoietic cell. Nat. Med. 3, 730-737 (1997).

Lapidot, T. et al. A cell initiating human acute myeloid leukaemia after transplantation into SCID mice. Nature 367, 645-648 (1994).

Bowie, M. B. et al. Identification of a new intrinsically timed developmental checkpoint that reprograms key hematopoietic stem cell properties. Proc. Natl. Acad. Sci. USA 104, 5878-5882 (2007).

Dierks, C. et al. Expansion of Bcr-Abl-positive leukemic stem cells is dependent on Hedgehog pathway activation. Cancer Cell 14, 238-249 (2008).

Huntly, B. J. et al. MOZ-TIF2, but not BCR-ABL, confers properties of leukemic stem cells to committed murine hematopoietic progenitors. Cancer Cell 6, 587-596 (2004).

Neering, S. J. et al. Leukemia stem cells in a genetically defined murine model of blastcrisis CML. Blood 110, 2578-2585 (2007).

Hu, Y. et al. Targeting multiple kinase pathways in leukemic prognitors and stem cells is essential for improved treatment of Ph+leukemia in mice. Proc. Natl. Acad. Sci. USA 103, 16870-16875 (2006).

Graham, S. M. et al. Primitive, quiescent, Philadelphia-positive stem cells from patients with chronic myeloid leukemia are insensitive to STI571 in vitro. Blood 99, 319-325 (2002).

Marley, S. B., Deininger, M. W., Davidson, R. J., Goldman, J. M. & Gordon, M. Y. The tyrosine kinase inhibitor STI571, like interferon-alpha, preferentially reduces the capacity for amplification of granulocyte-macrophage progenitors from patients with chronic myeloid leukemia. Exp. Hematol. 28, 551-557 (2000).

Taylor, P. M. et al. Breast cancer cell-derived EMMPRIN stimulates fibroblast MMP2 release through a phospholipase A(2) and 5-lipoxygenase catalyzed pathway. Oncogene 21, 5765-5772 (2002).

Li, S., Ilaria, R. L. Jr, Million, R. P., Daley, G. Q. & Van Etten, R. A. The P190, P210, and p230 forms of the BCR/ABL oncogene induce a similar chronic myeloid leukemia-like syndrome in mice but have different lymphoid leukemogenic activity. J. Exp. Med. 189, 1399-1412 (1999).

Knapp, H. R. Reduced allergen-induced nasal congestion and leukotriene synthesis with an orally active 5-lipoxygenase inhibitor. N. Engl. J. Med. 323, 1745-1748 (1990).

Ferreira, R., Ohneda, K., Yamamoto, M. & Philipsen, S. GATA1 function, a paradigm for transcription factors in hematopoiesis. Mol. Cell. Biol. 25, 1215-1227 (2005).

Tsang, A. P. et al. FOG, a multitype zinc finger protein, acts as a cofactor for transcription factor GATA-1 in erythroid and megakaryocytic differentiation. Cell 90, 109-119 (1997).

Stenke, L., Lauren, L., Reizenstein, P. & Lindgren, J. A. Leukotriene production by fresh human bone marrow cells: evidence of altered lipoxygenase activity in chronic myelocytic leukemia. Exp. Hematol. 15, 203-207 (1987).

Tornhamre, S. et al. Inverse relationship between myeloid maturation and leukotriene C4 synthase expression in normal and leukemic myelopoiesis-consistent overexpression of the enzyme in myeloid cells from patients with chronic myeloid leukemia. Exp. Hematol. 31, 122-130 (2003).

Peng, C. et al. Inhibition of heat shock protein 90 prolongs survival of mice with BCRABL-T3151-induced leukemia and suppresses leukemic stem cells. Blood 110, 678-685 (2007).

Graham, S. M., Vass, J. K., Holyoake, T. L. & Graham, G. J. Transcriptional analysis of quiescent and proliferating CD34+ human hemopoietic cells from normal and chronic myeloid leukemia sources. Stem Cells 25, 3111-3120 (2007).

Radich, J. P. et al. Gene expression changes associated with progression and response in chronic myeloid leukemia. Proc. Natl. Acad. Sci. USA 103, 2794-2799 (2006).

Anderson, K. M. et al. Selective inhibitors of 5-lipoxygenase reduce CML blast cell proliferation and induce limited differentiation and apoptosis. Leuk. Res. 19, 789-801 (1995).

Hu, Y. et al. Requirement of Src kinases Lyn, Hck and Fgr for BCR-ABL1-induced B-lymphoblastic leukemia but not chronic myeloid leukemia. Nat. Genet. 36, 453-461 (2004).

Li, S., Couvillon, A. D., Brasher, B. B. & Van Etten, R. A. Tyrosine phosphorylation of Grb2 by Bcr/Abl and epidermal growth factor receptor: a novel regulatory mechanism for tyrosine kinase signaling. EMBO J. 20, 6793-6804 (2001).

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of treating a subject having chronic phase BCR-ABL-induced myeloid leukemia characterized by oncogene-mediated elevated arachidonate 5-lipoxygenase, comprising:
administering a therapeutically effective amount of an arachidonate 5-lipoxygenase inhibitor to the subject; and
administering a therapeutically effective dose of a BCR-ABL tyrosine kinase inhibitor to the subject,
wherein leukemia stem cells are inhibited.

2. The method of claim 1, wherein the arachidonate 5-lipoxygenase inhibitor is selected from the group consisting of: N-[1-(1-benzothien-2-yl)ethyl]-N-hydroxyurea (zileuton), atreleuton, BW-B 70C, darbufelone, licofelone, minocycline, tepoxalin, tebufelone, curcumin, DHDMBF, BF389, RJW63556, PGV20229, CI986, S2474, ZD2138, CJ-13,610, L-739,010, Wy-50295, TMK688, PEP03, GSK-2190915 and AZD-4407.

3. The method of claim 1, wherein the kinase inhibitor is selected from the group consisting of: imatinib, dasatinib, nilotinib, bosutinib, AZD0530, NPB-001-05, AT9283, BAY 43-9006, bafetinib, AP24534, lestaurtinib, tozasertib, danusertib, XL228, KW-2449, AT-9283, VE-465, DCC-2036, PKC412, PF-03814735 and vatalanib.

4. The method of claim 1, further comprising administering a therapeutically effective dose of a 5-lipoxygenase-activating protein inhibitor.

5. The method of claim 4, wherein the 5-lipoxygenase-activating protein inhibitor is selected from the group consisting of: 1-[(4-chlorophenyl)methyl]3-[(1,1-dimethylethyl)thio]-α, α-dimethyl-5-(1-methylethyl)-1H-indole-2-propanoic acid (MK886), MK-0591, BAY-X-1005 and AM679.

6. The method of claim 1, further comprising administering a therapeutically effective dose of a kinase inhibitor selected from the group consisting of: a dual specificity kinase inhibitor, a multi-specificity kinase inhibitor, a src kinase inhibitor and an aurora kinase inhibitor.

7. The method of claim 1, further comprising administering a therapeutically effective dose of an Hsp90 inhibitor.

8. The method of claim 1, further comprising administering a therapeutically effective dose of an anti-cancer agent selected from the group consisting of: a protein synthesis inhibitor, an anti-metabolite, an alkylating agent, a steroid, interferon alpha 2b; and a combination of any two or more thereof.

9. The method of claim 1, wherein the subject is resistant to anti-cancer effects of a therapeutic agent selected from the group consisting of: imatinib, dasatinib and nilotinib.

* * * * *